United States Patent
Sung et al.

(10) Patent No.: US 11,219,221 B2
(45) Date of Patent: Jan. 11, 2022

(54) COMPOSITION AND METHOD FOR CONFERRING AND/OR ENHANCING HERBICIDE TOLERANCE USING VARIANTS OF PROTOPORPHYRINOGEN IX OXIDASE FROM CYANOBACTERIA

(71) Applicant: FarmHannong Co., Ltd., Seoul (KR)

(72) Inventors: Soon-Kee Sung, Daejeon (KR); Joonseon Yoon, Daejeon (KR); Joonghyuk Park, Daejeon (KR); Young Ock Ahn, Daejeon (KR); Joo Yong Woo, Daejeon (KR); Myoung-Ki Hong, Daejeon (KR); Yunjung Han, Daejeon (KR)

(73) Assignee: FARMHANNONG CO., LTD., Seoul (KR)

( * ) Notice: Subject to any disclaimer, the term of this patent is extended or adjusted under 35 U.S.C. 154(b) by 0 days.

(21) Appl. No.: 16/772,895

(22) PCT Filed: Dec. 11, 2018

(86) PCT No.: PCT/KR2018/015655
§ 371 (c)(1),
(2) Date: Jun. 15, 2020

(87) PCT Pub. No.: WO2019/117579
PCT Pub. Date: Jun. 20, 2019

(65) Prior Publication Data
US 2021/0269821 A1    Sep. 2, 2021

(30) Foreign Application Priority Data
Dec. 15, 2017 (KR) .......................... 10-2017-0173633

(51) Int. Cl.
*C12N 15/82* (2006.01)
*A01N 63/50* (2020.01)
*C07K 14/195* (2006.01)

(52) U.S. Cl.
CPC .......... *A01N 63/50* (2020.01); *C07K 14/195* (2013.01); *C12N 15/8274* (2013.01); *C12Y 103/03004* (2013.01)

(58) Field of Classification Search
CPC .............................................. C12N 15/8274
See application file for complete search history.

(56) References Cited

U.S. PATENT DOCUMENTS

| | | | |
|---|---|---|---|
| 6,308,458 B1 | 10/2001 | Volrath et al. | |
| 6,808,904 B2 | 10/2004 | Ward et al. | |
| 7,563,950 B2 | 7/2009 | Matsushima et al. | |
| 2015/0252379 A1 | 9/2015 | Hutzler et al. | |
| 2016/0374339 A1* | 12/2016 | Aponte .............. | C12N 15/8274 504/134 |

FOREIGN PATENT DOCUMENTS

| | | |
|---|---|---|
| KR | 10-2007-0114338 | 12/2007 |
| KR | 10-2014-0033330 | 3/2014 |
| KR | 1020150023748 | 3/2015 |
| KR | 10-2016-0073340 | 6/2016 |
| WO | 2011-085221 | 7/2011 |
| WO | 2013-189984 | 12/2013 |
| WO | 2015-092706 | 6/2015 |
| WO | 2016-203377 | 12/2016 |

OTHER PUBLICATIONS

NCBI Reference Sequence: WP_017303635.1 (published Aug. 19, 2015); Presented in IDS submitted by Applicant. (Year: 2015).*
NCBI, Reference Sequence No. WP_017303635.1, protoporphyrinogen oxidase [Spirulina subsalsa], May 21, 2019.
Xianggan Li et al., "Development of protoporphyrinogen oxidase as an efficient selection marker for agrobacterium tumefaciens-mediated transformation of Maize", Plant Physiol. 133:736-747, Sep. 11, 2003.
Ujjana B. Nandihalli et al, "Relationships between molecular properties and biological activities of O-phenyl pyrrolidino- and piperidinocarbamate Herbicides", J. Agric. Food Chem., 40(10) 1993-2000, Oct. 1, 1992.
Naohide Watanabe et al., "Dual targeting of spinach protoporphyrinogen oxidase II to mitochondria and chloroplasts by alternative use of two in-frame initiation Codons", J. Biol. Chem. 276(23):20474-20481, Mar. 23, 2001.
Fang-Sik Che et al., Molecular characterization and subcellular localization of protoporphyrinogen oxidase in spinach chloroplasts. Plant Physiol. 124(1):59-70, Sep. 2000.
KIPO, PCT Search Report & Written Opinion of PCT/KR2018/015655 dated May 27, 2019.
NCBI Reference Sequence: WP_024124463.1, protoporphyrinogen oxidase [*Thermosynechococcus* sp. NK55a], Aug. 26, 2021.
GenBank Accession No. AHB88054.1, protoporphyrinogen oxidase HemY [*Thermosynechococcus* sp. NK55a], Aug. 26, 2021.

* cited by examiner

*Primary Examiner* — Weihua Fan

(74) *Attorney, Agent, or Firm* — Lex IP Meister, PLLC

(57) ABSTRACT

Provided is a technology for conferring enhanced tolerance and/or enhancing tolerance to a herbicide of a plant and/or algae by using amino acid variants of protoporphyrinogen IX oxidase derived from prokaryotes.

23 Claims, 36 Drawing Sheets
Specification includes a Sequence Listing.

[FIG. 1]
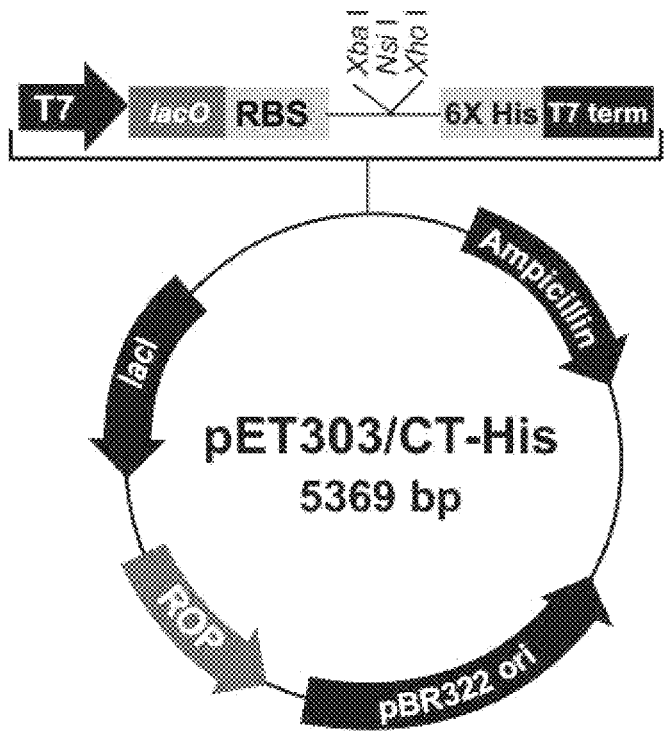
Comments for pET303 CT-His
5369 nucleotides
T7 promoter: bases 20-36
T7 promoter priming site: bases 20-39
lac operator (lacO): bases 39-63
Ribosome binding site (RBS): bases 95-100
6X His Tag: bases 119-136
T7 reverse priming site: bases 186-206
T7 transcription termination region: bases 147-277
F1 origin: bases 287-742
bla promoter: bases 775-879
Ampicillin (bla) resistance gene: bases 874-1734
pBR322 origin: bases 1945-2678 (c)
ROP ORF: bases 2920-3011 (c)
lacI ORF: bases 3914-5032 (c)

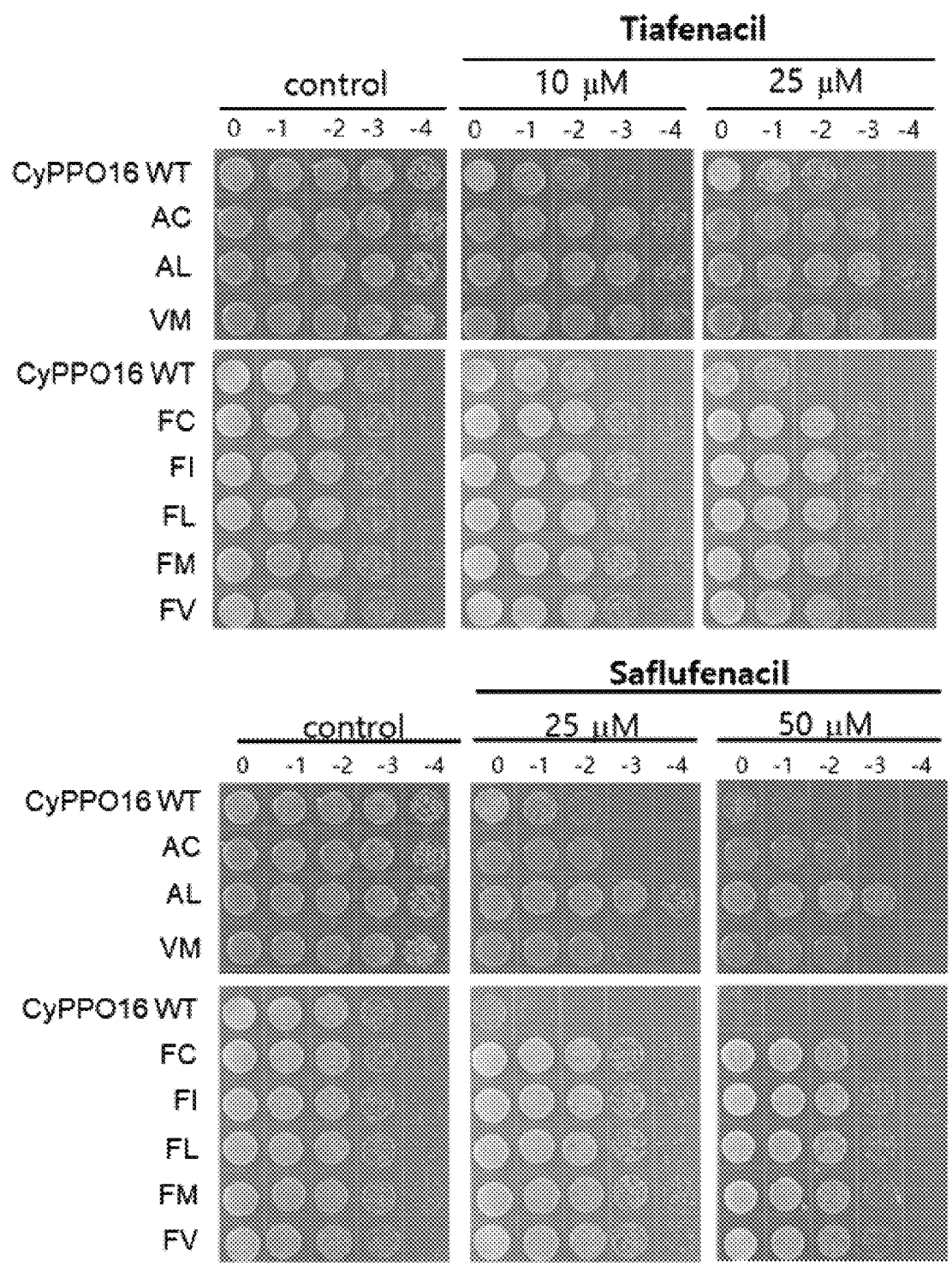
[FIG. 2]

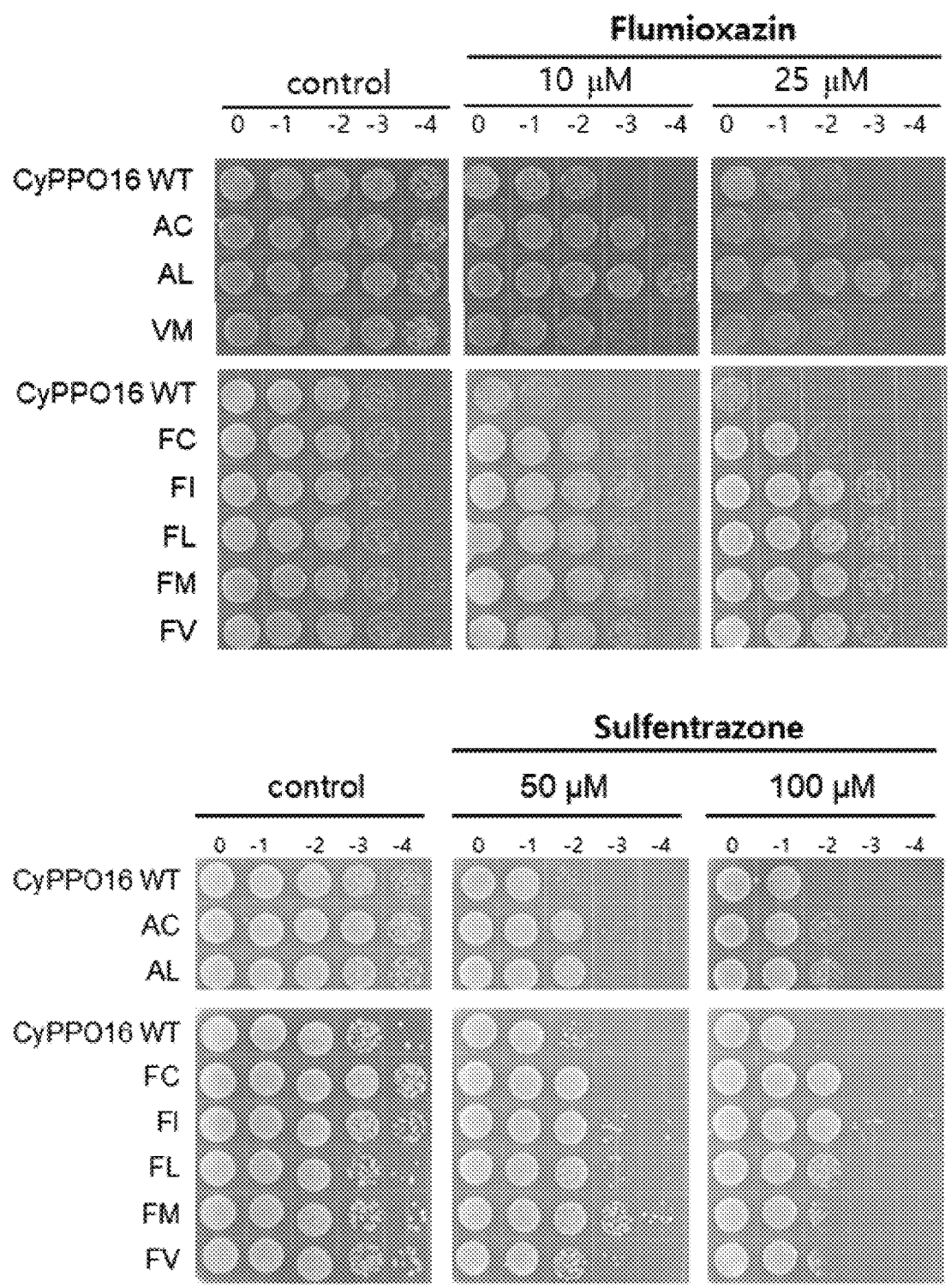
[FIG. 3]

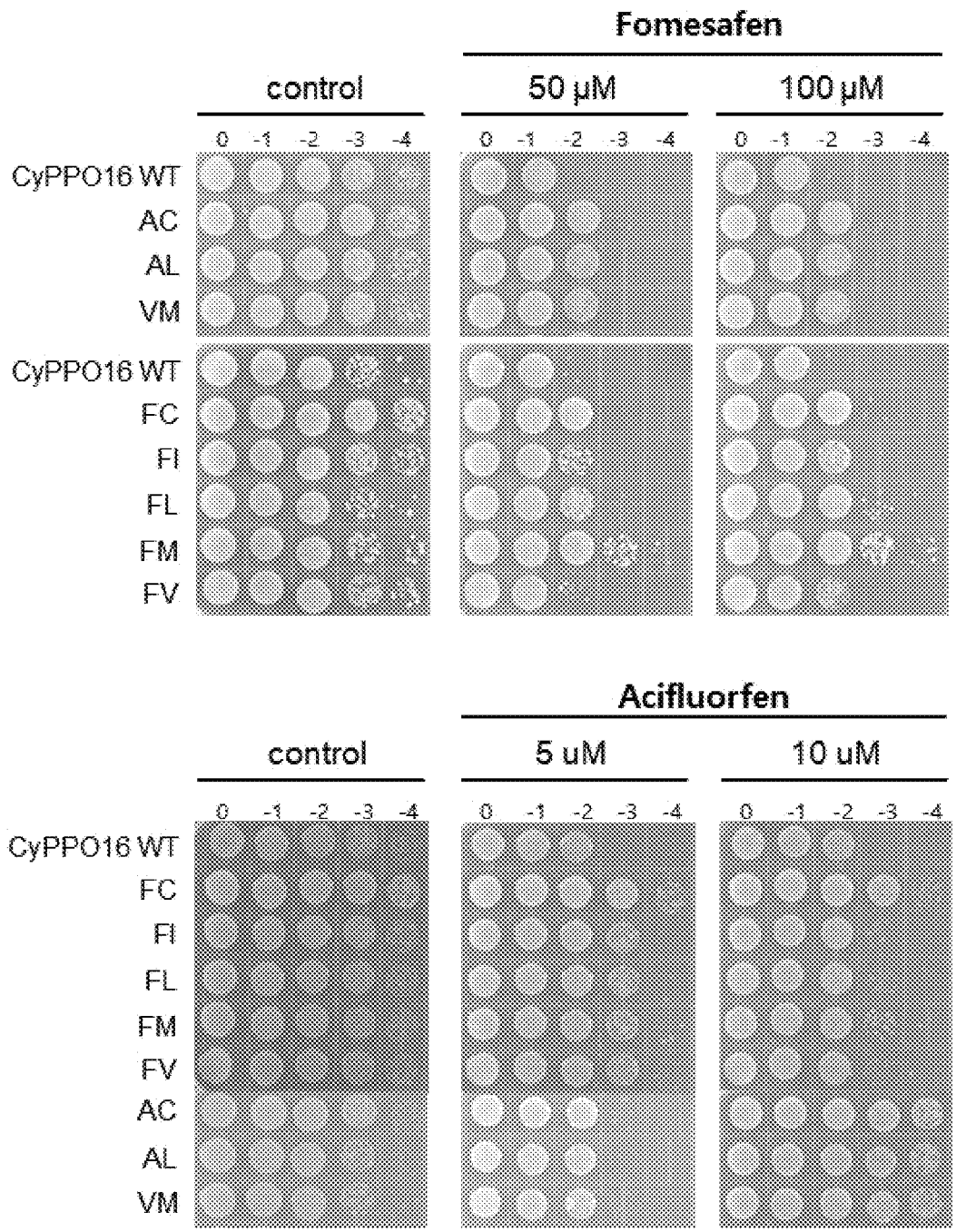
[FIG. 4]

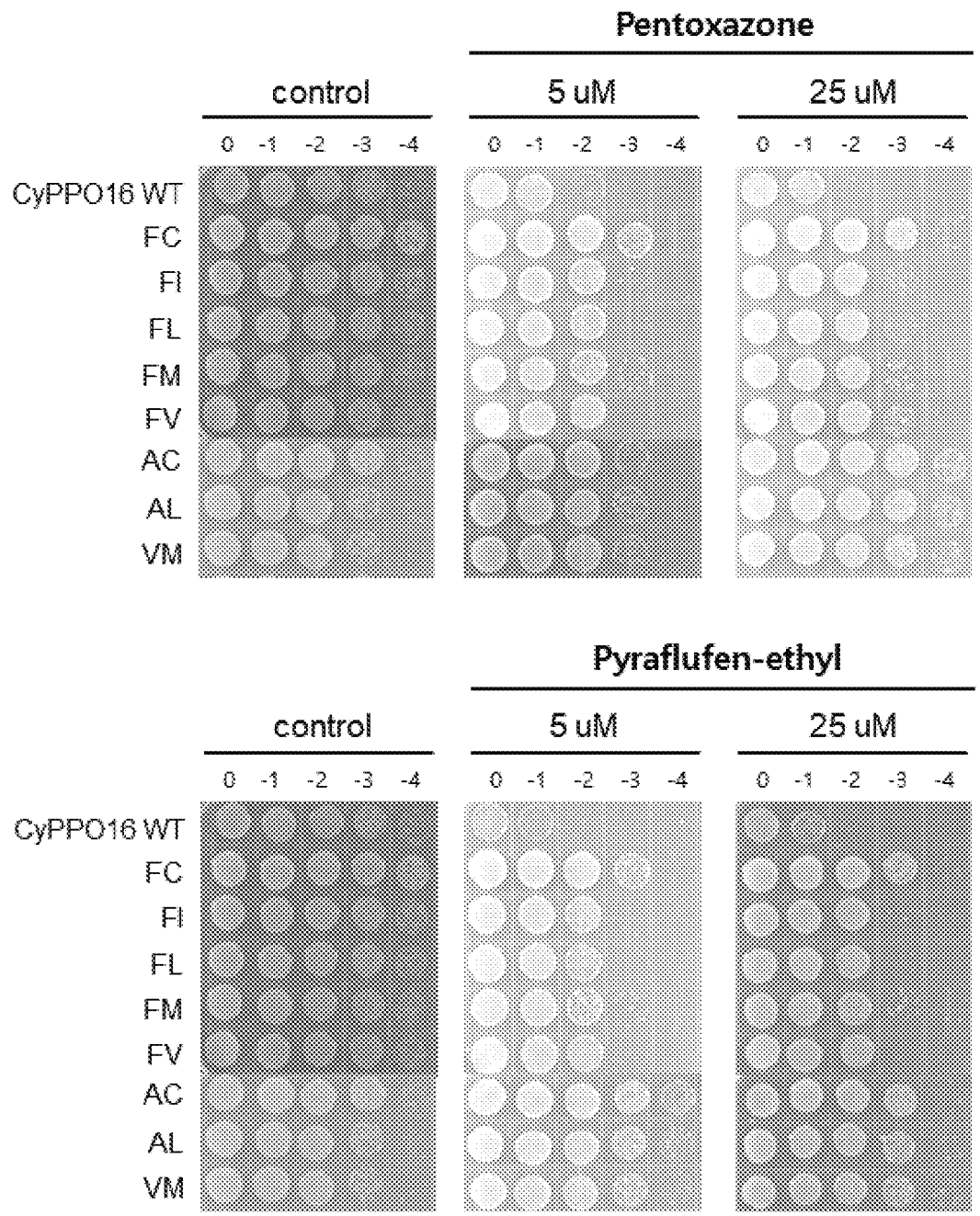
[FIG. 5]

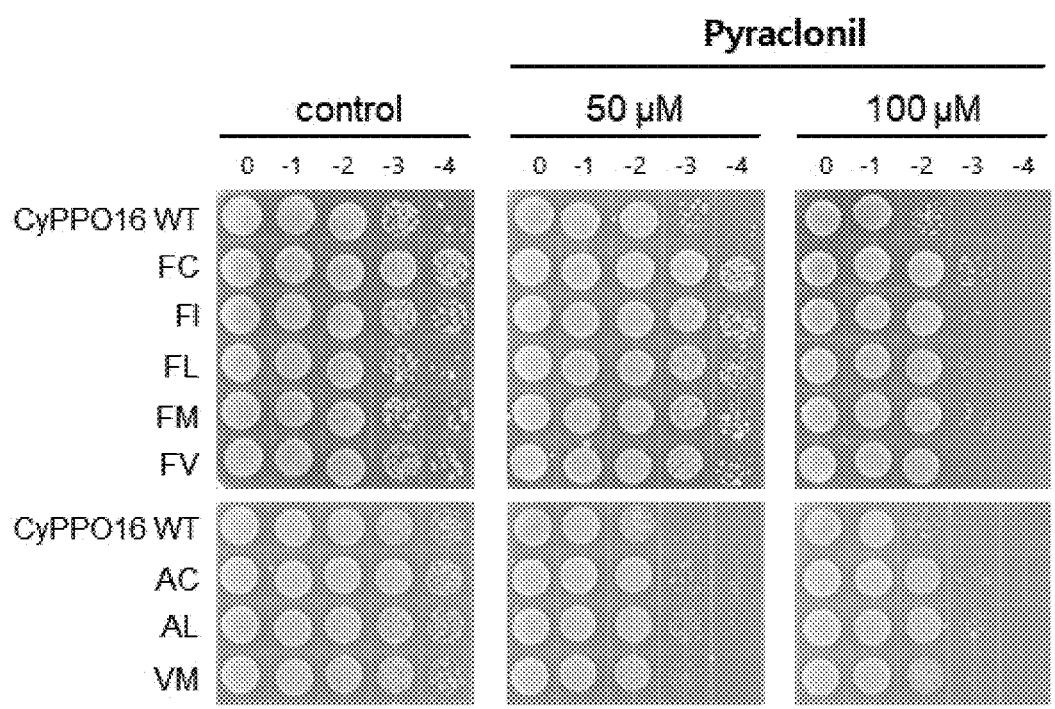
[FIG. 6]

[FIG. 7]
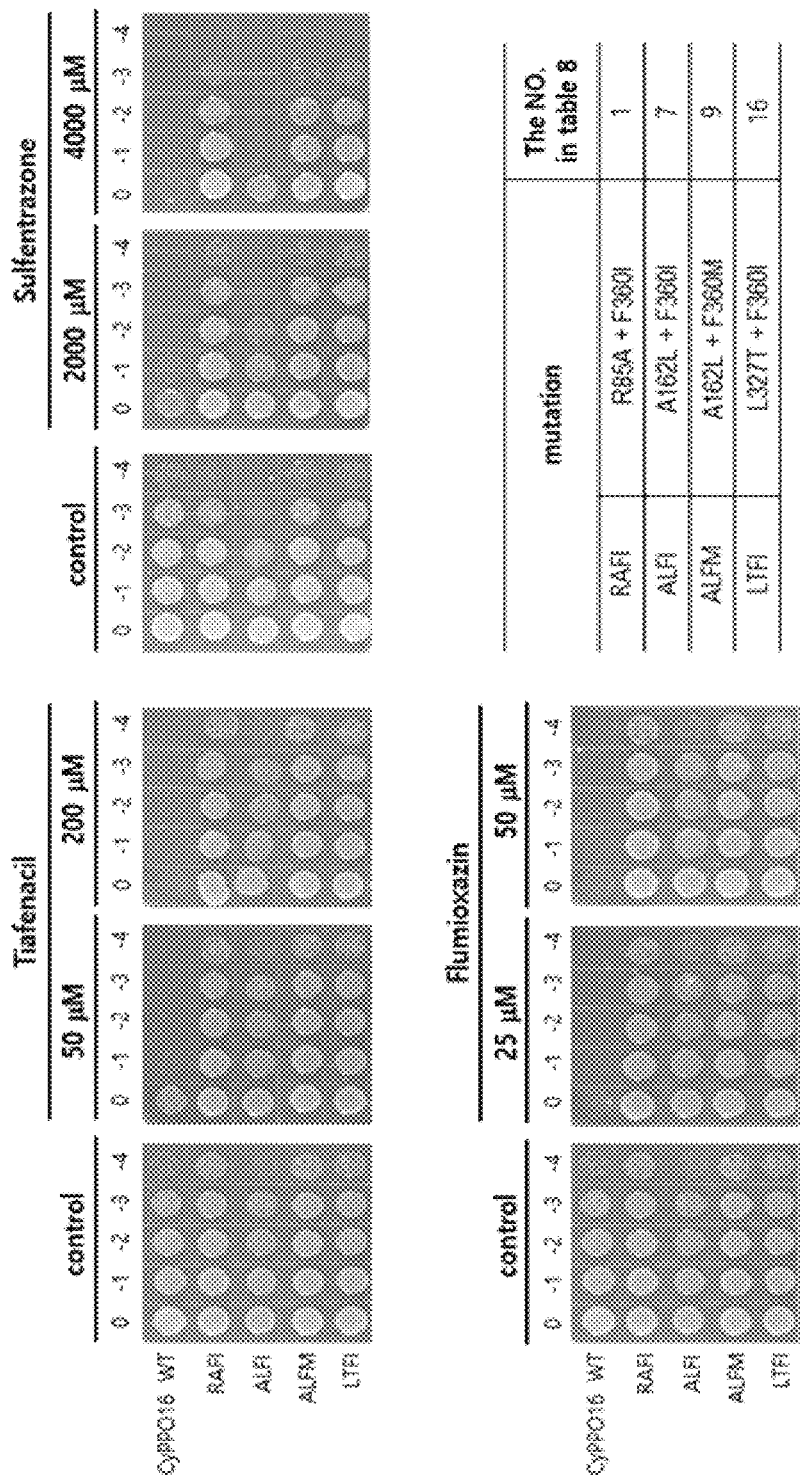

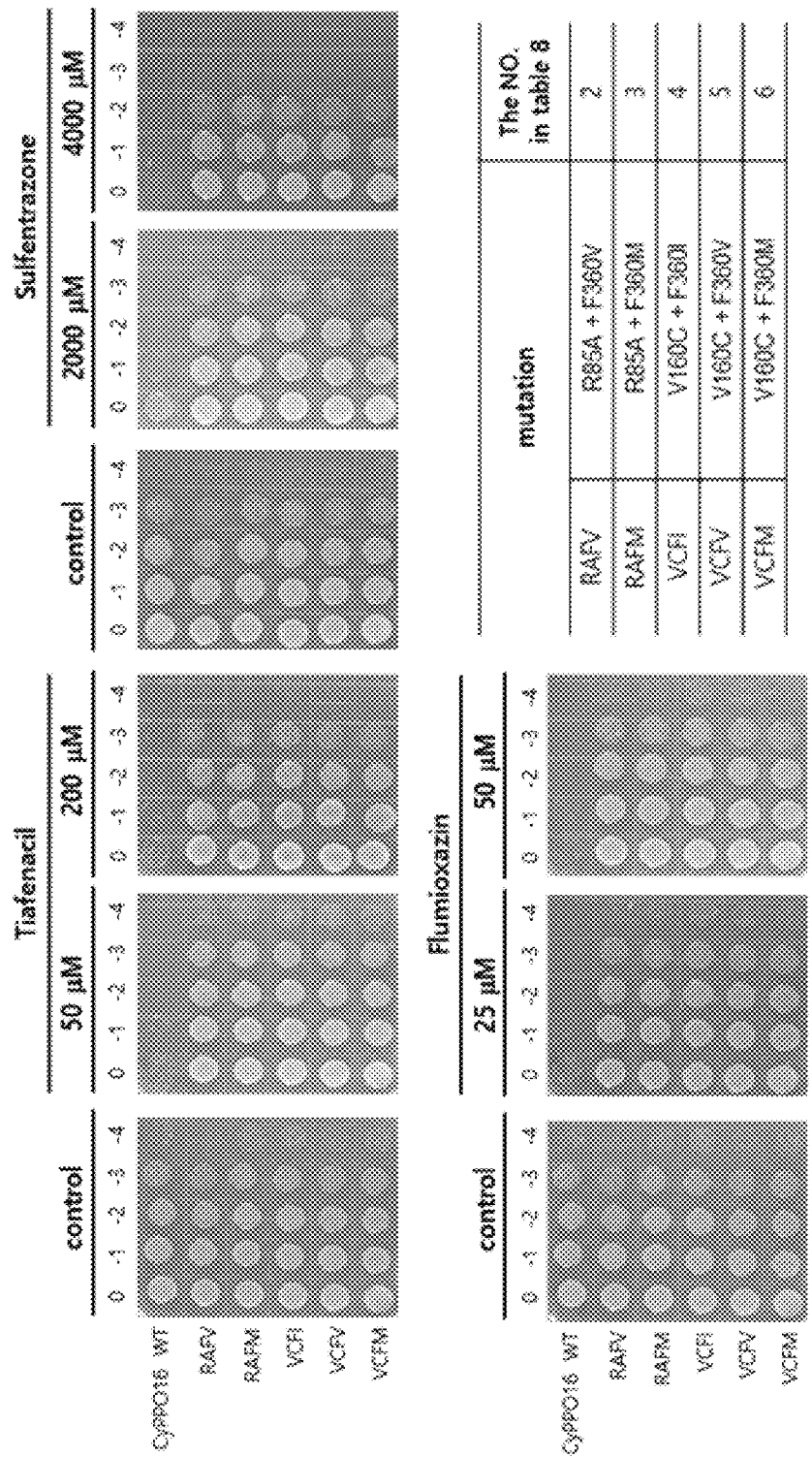
[FIG. 8]

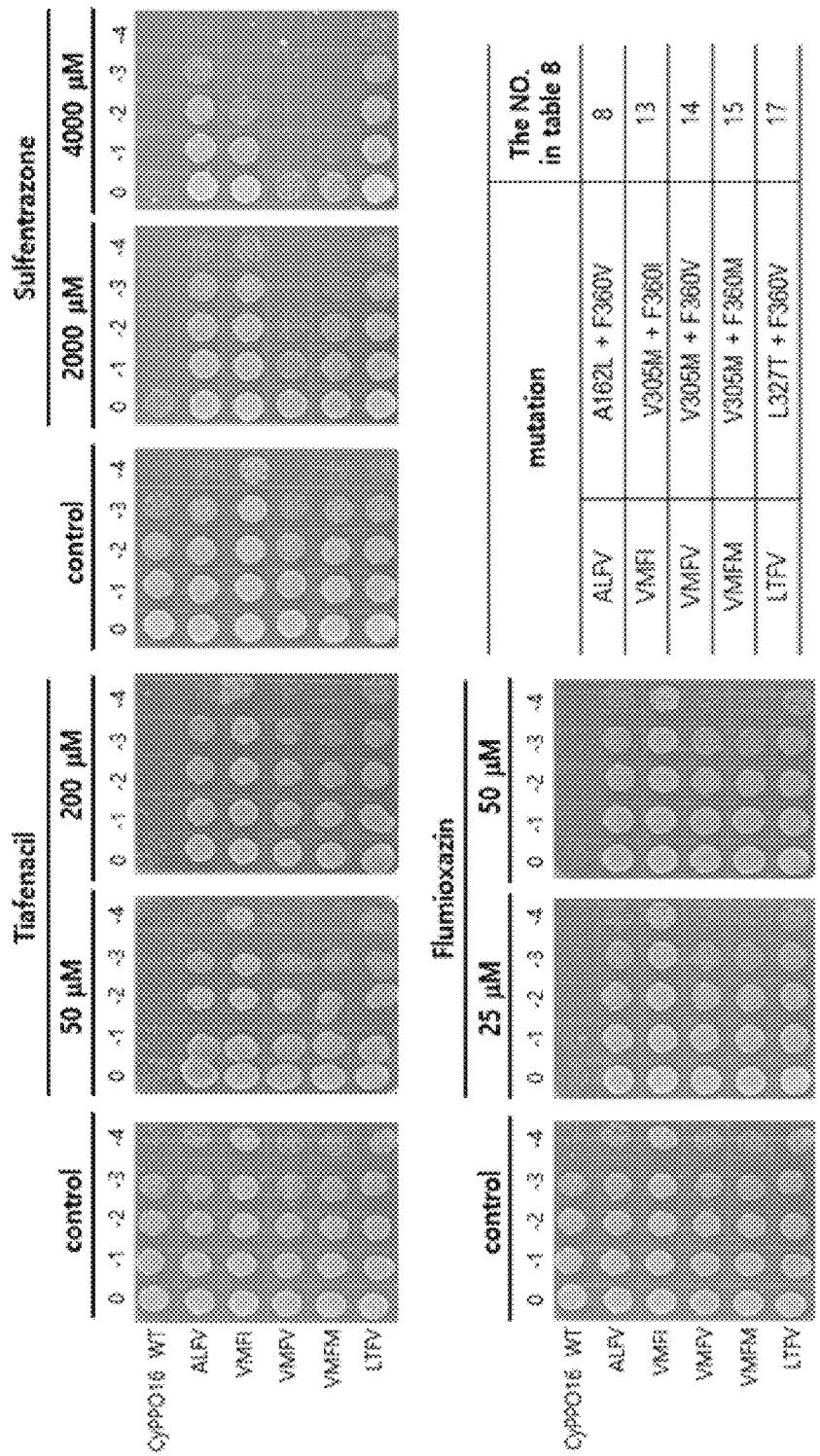
[FIG. 9]

[FIG. 10]
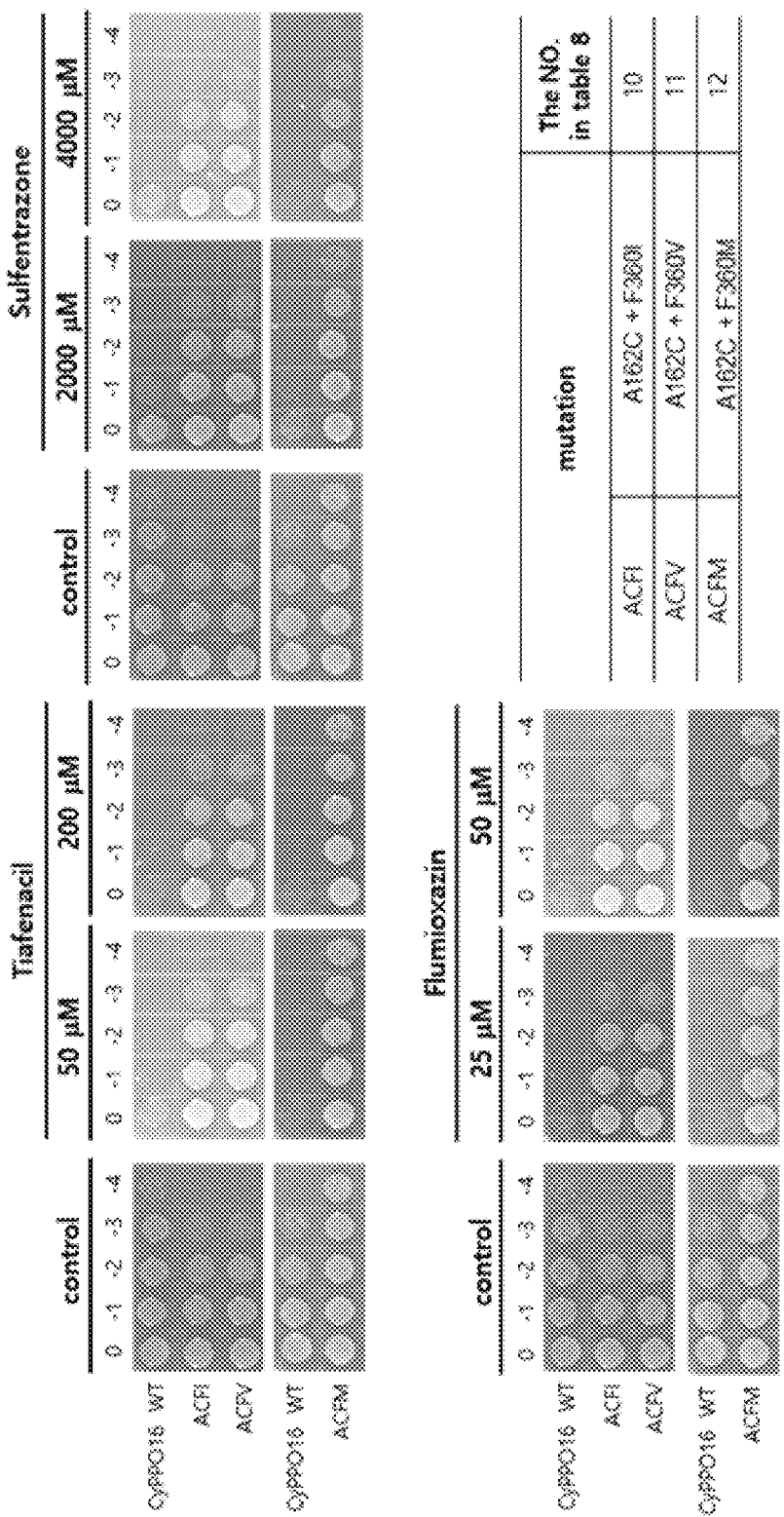

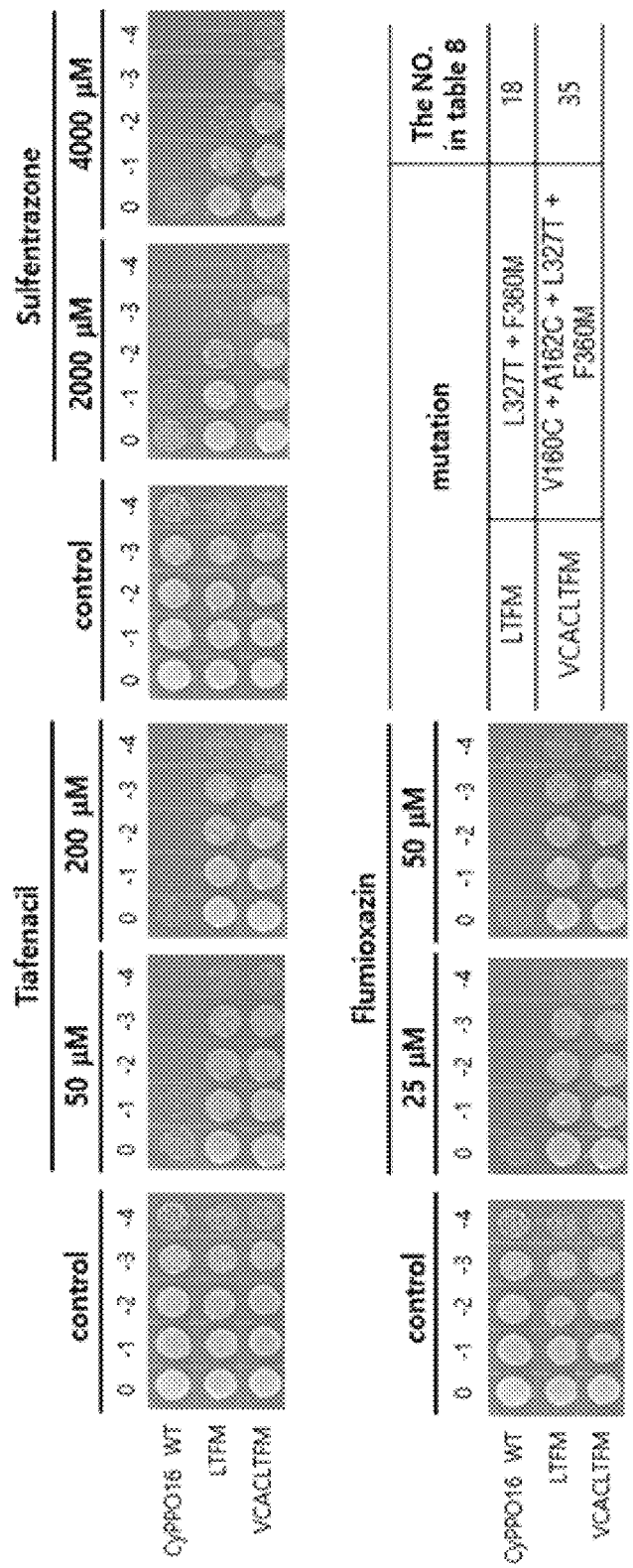
[FIG. 11]

[FIG. 12]
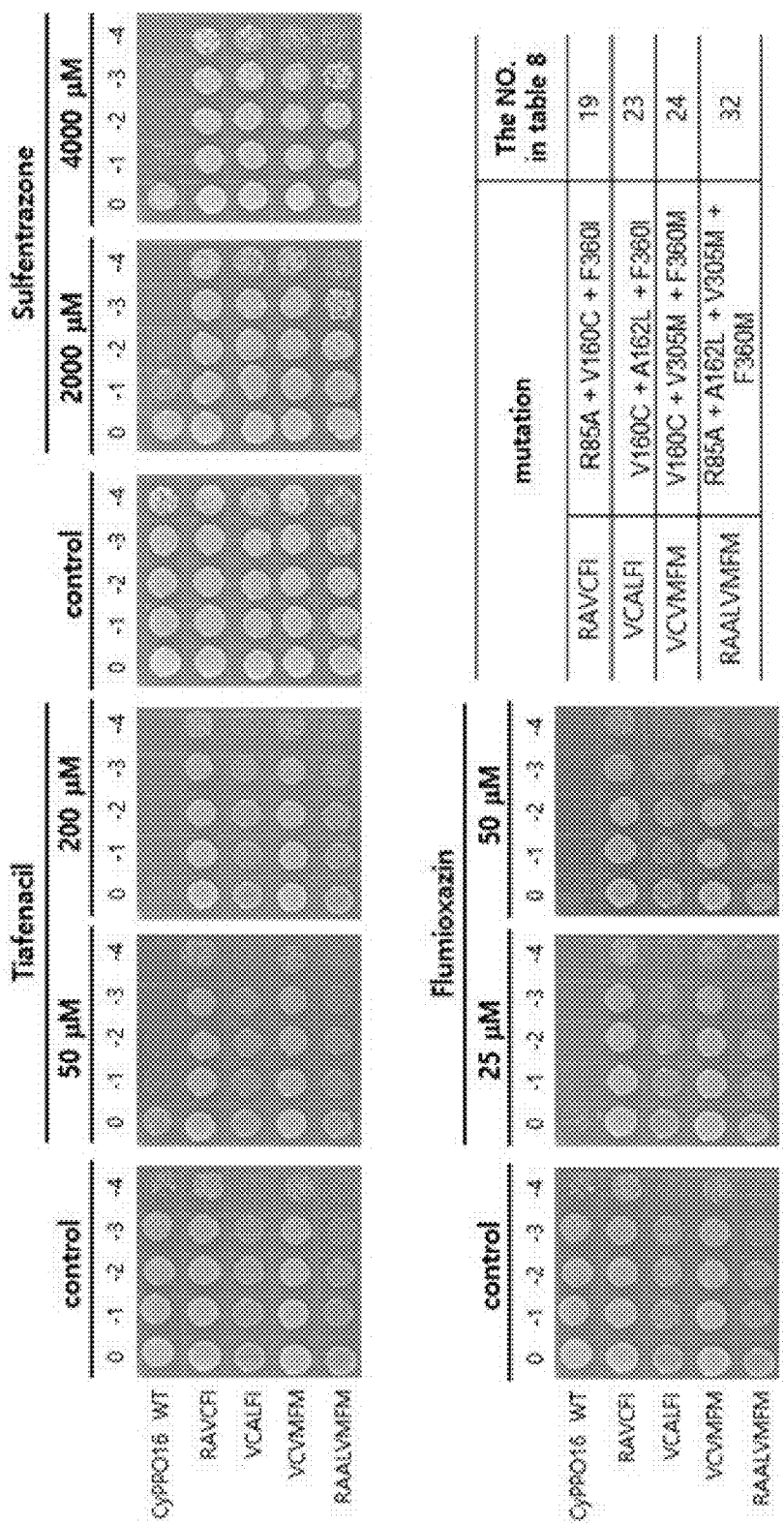

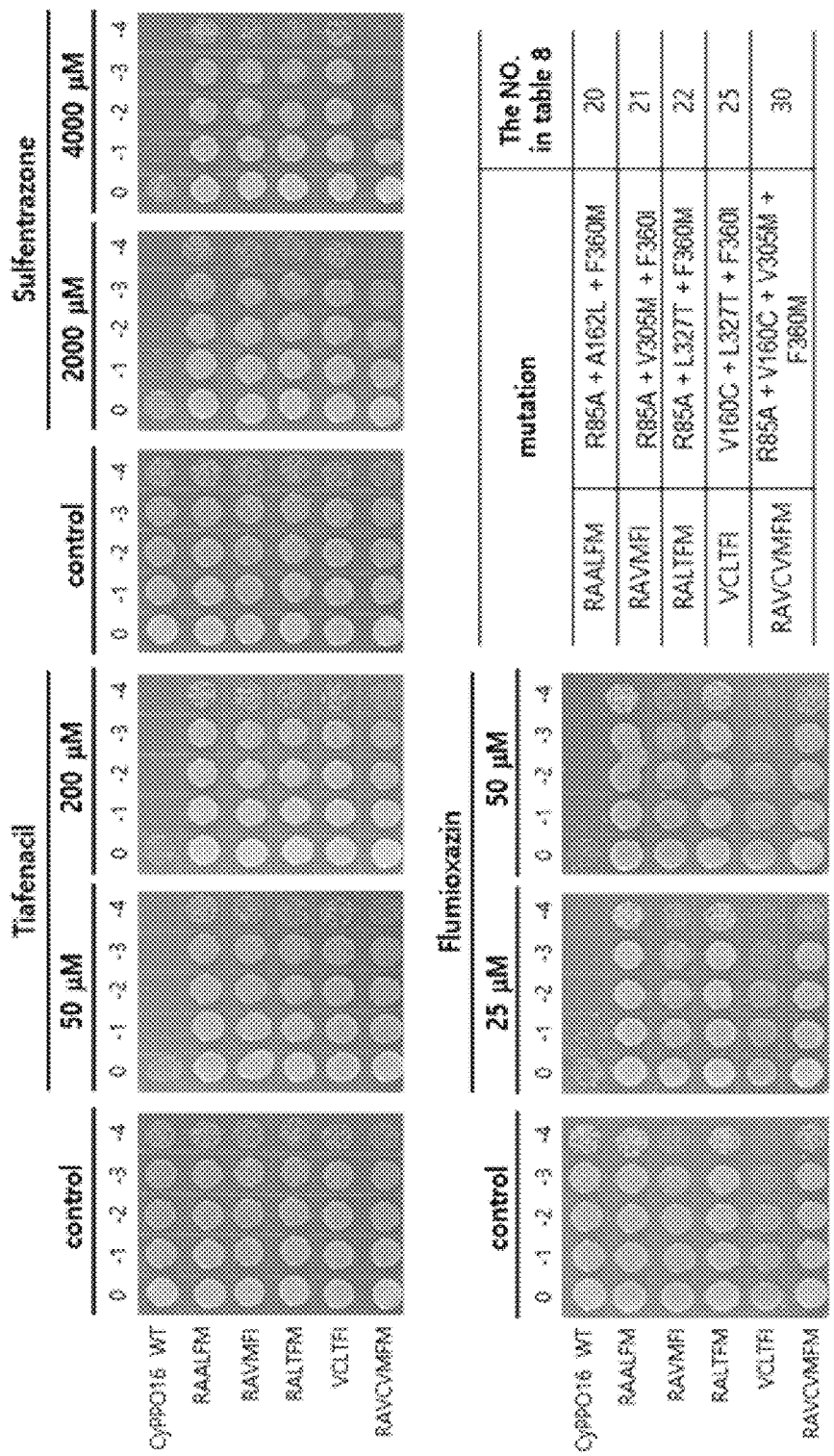
[FIG. 13]

[FIG. 14]
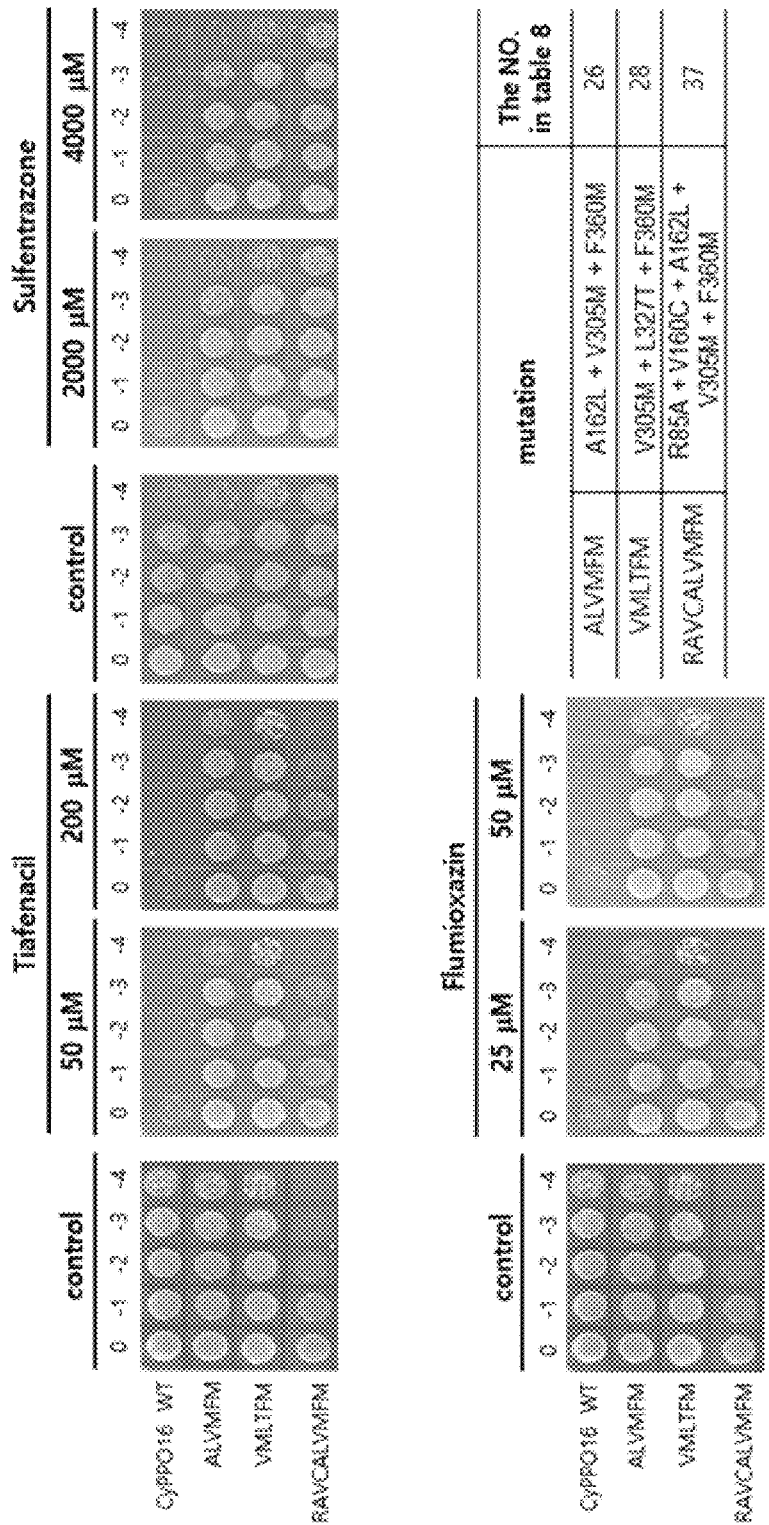

[FIG. 15]
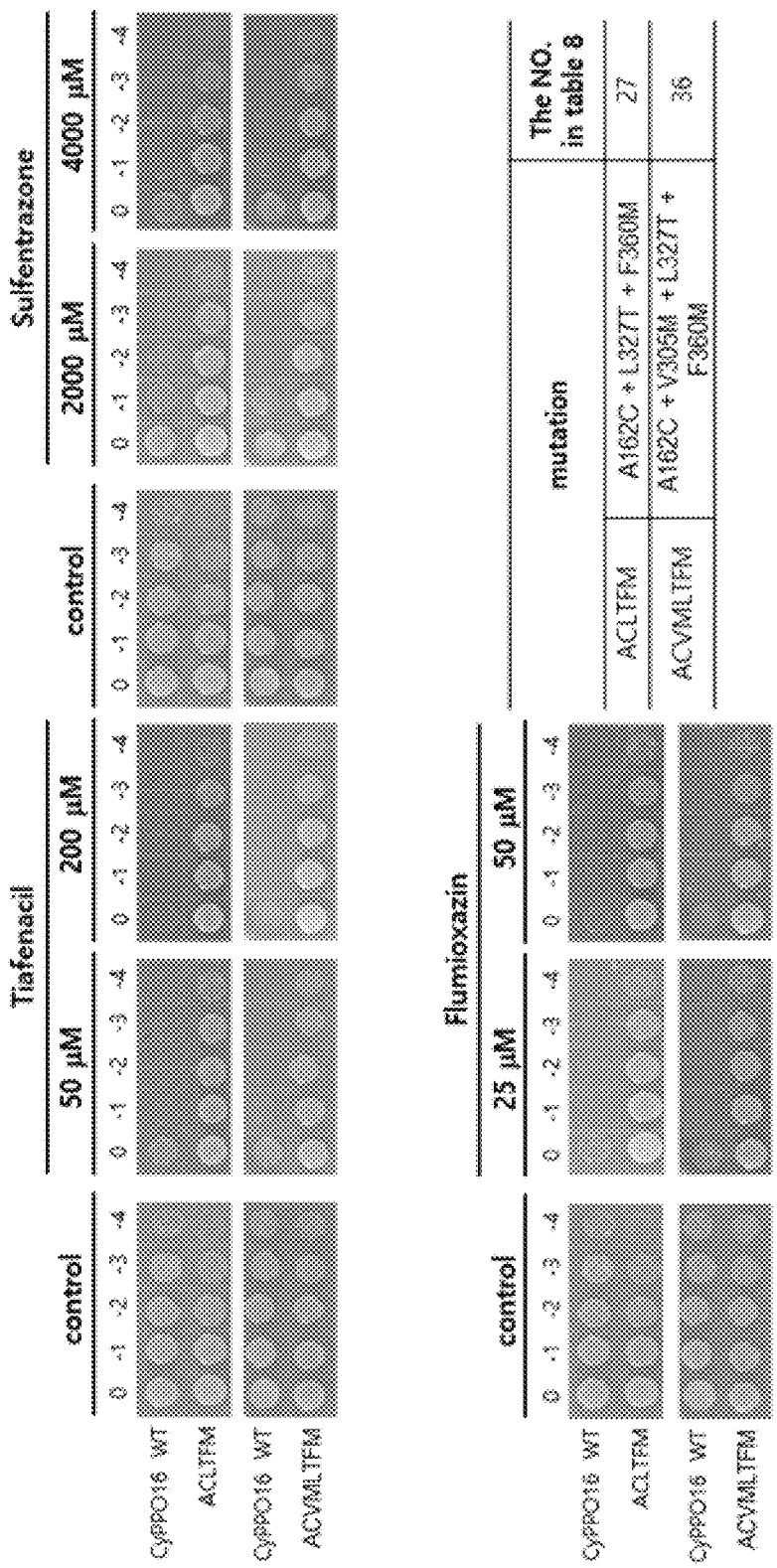

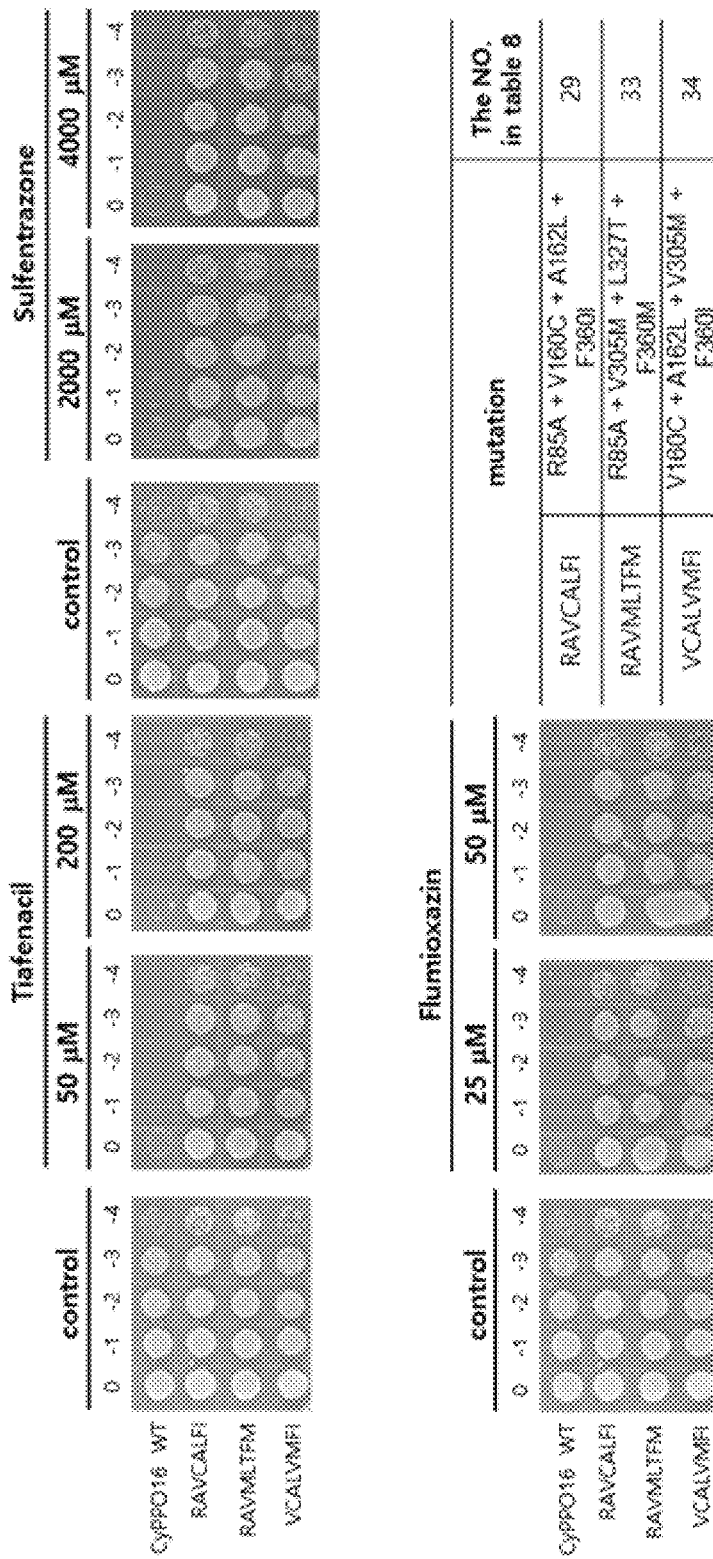
[FIG. 16]

[FIG. 17]
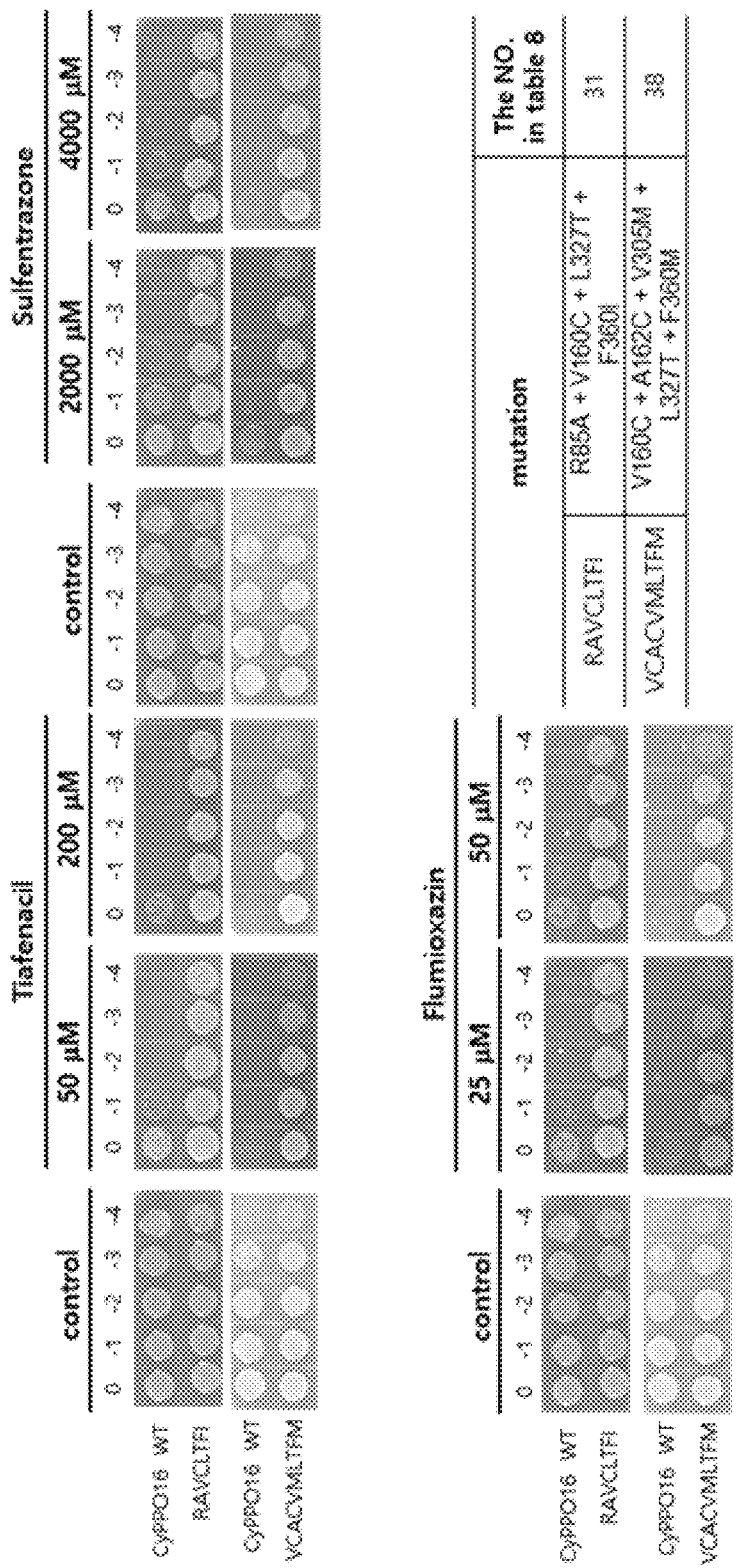

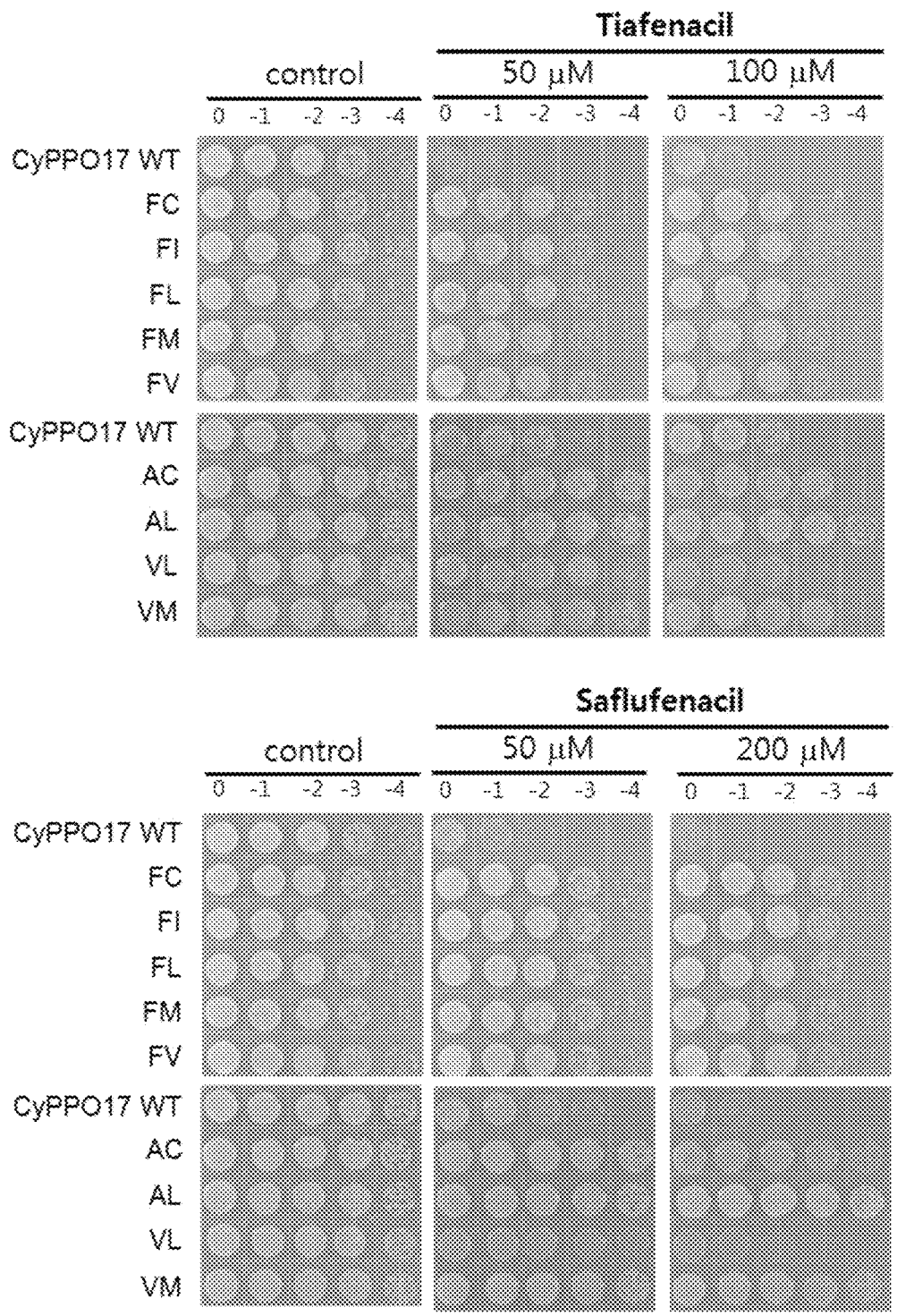
[FIG. 18]

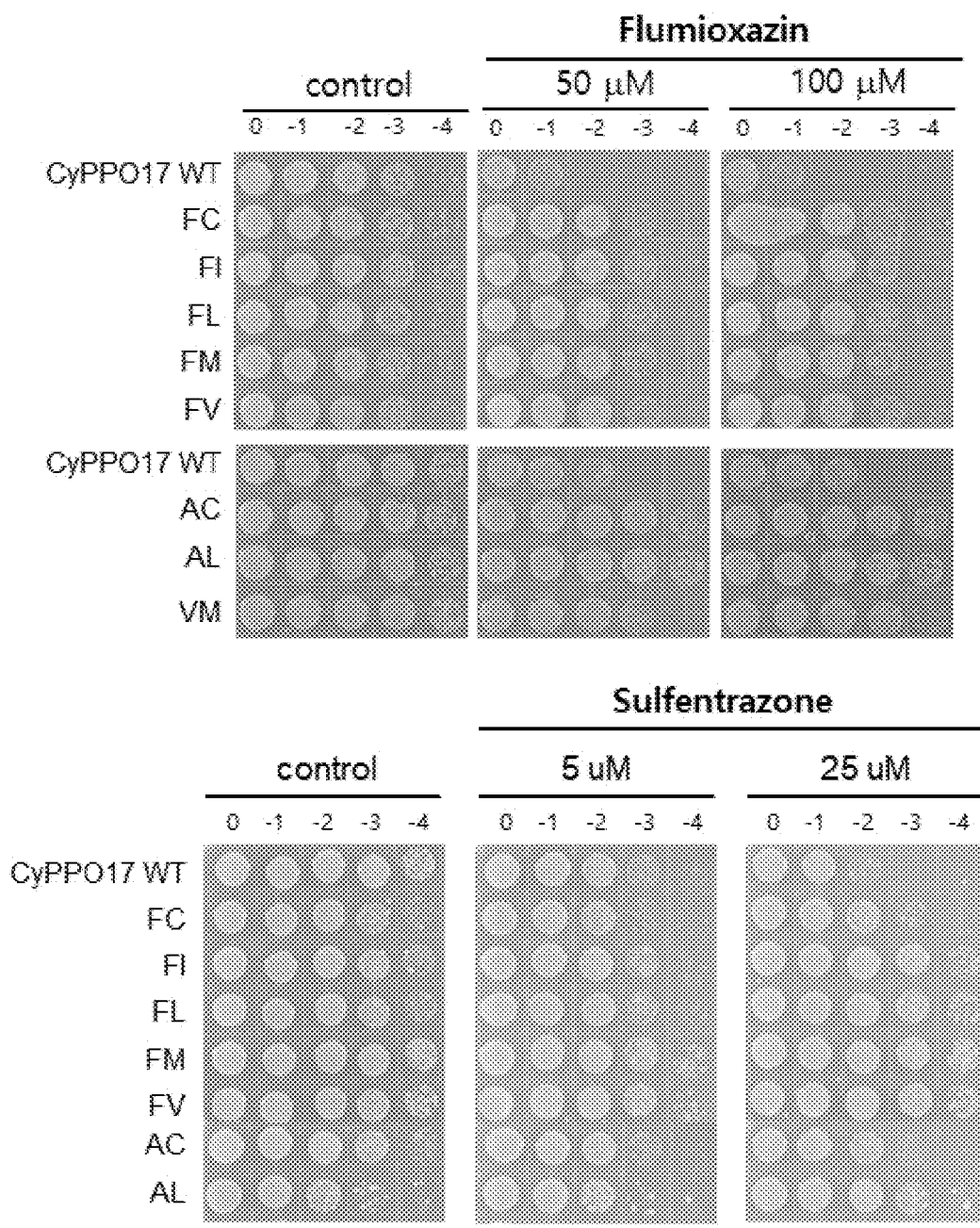
[FIG. 19]

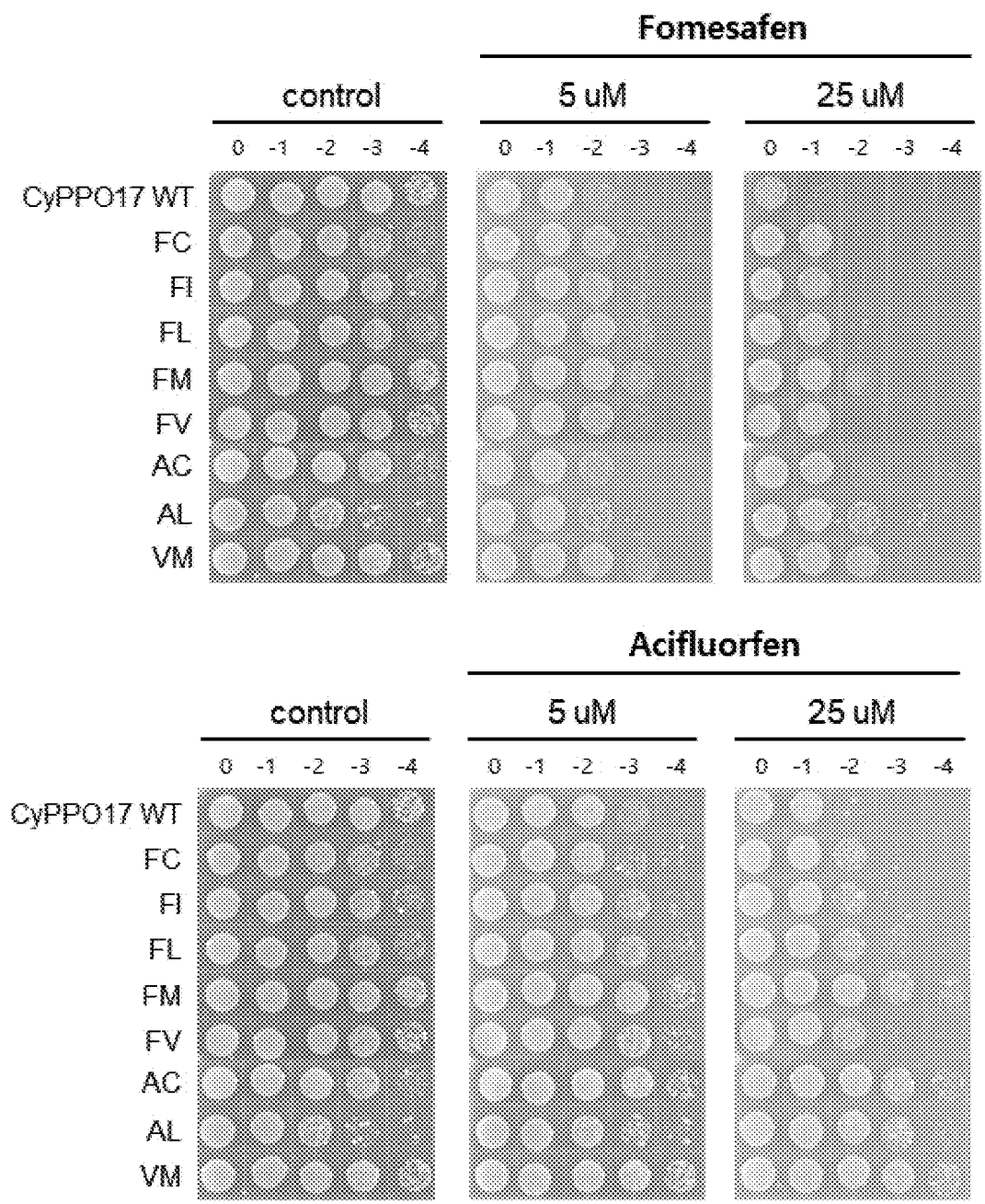
[FIG. 20]

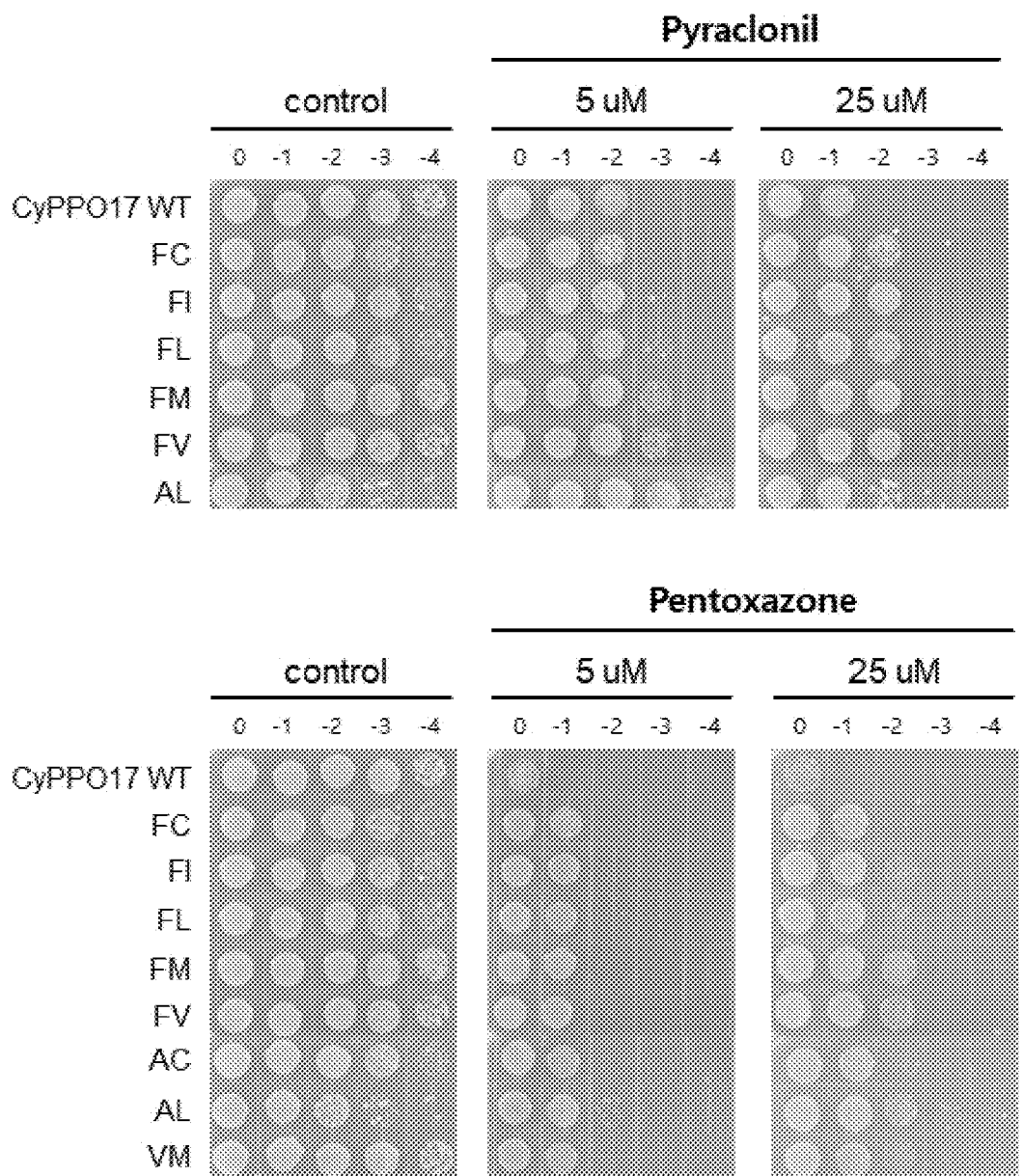
[FIG. 21]

[FIG. 22]
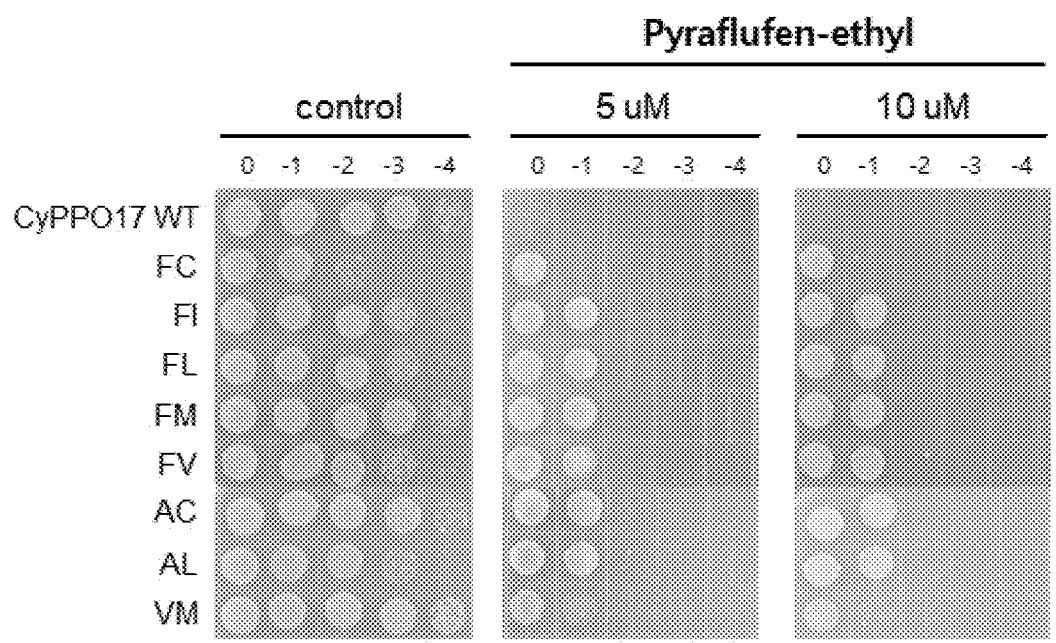

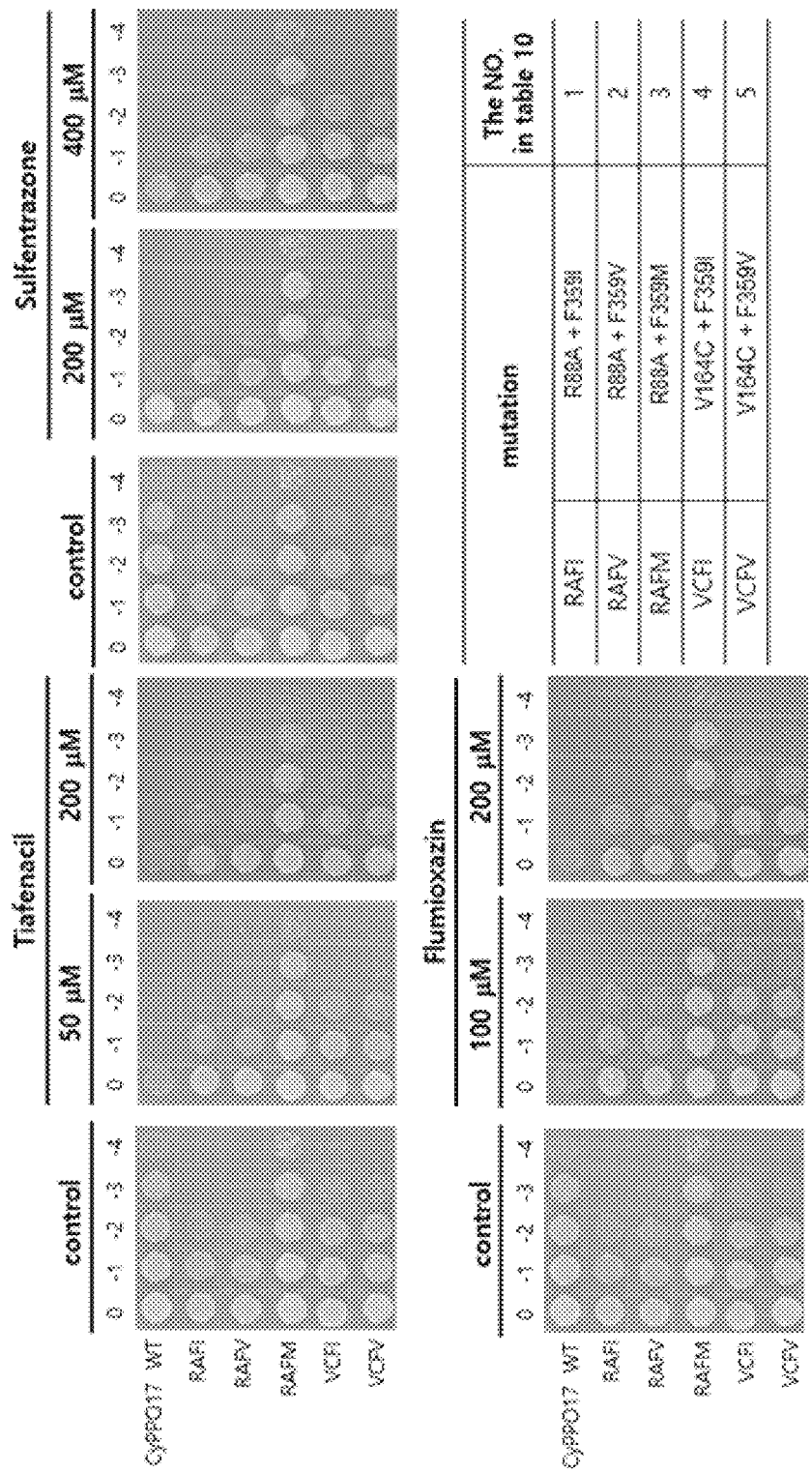
[FIG. 23]

[FIG. 24]
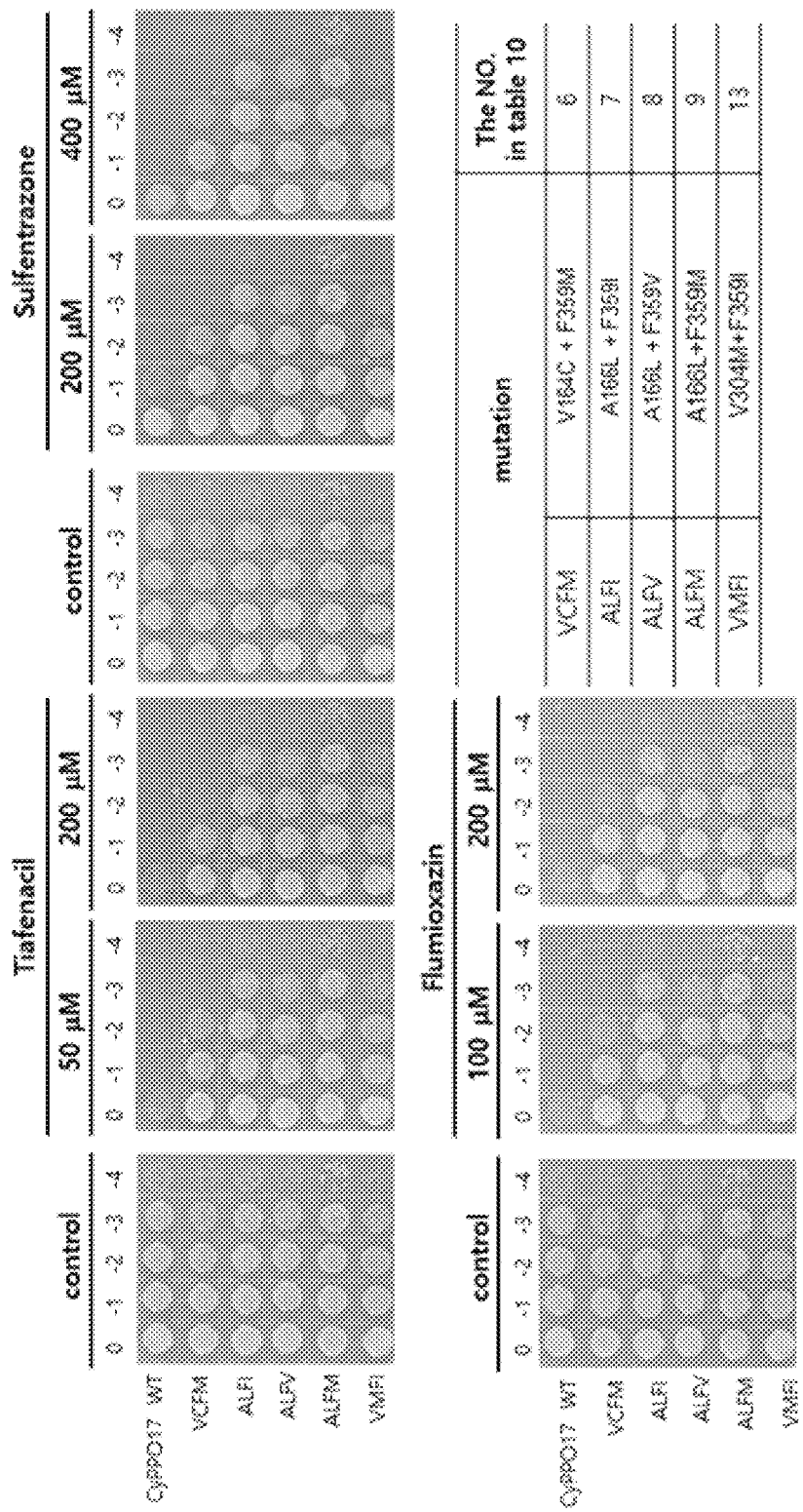

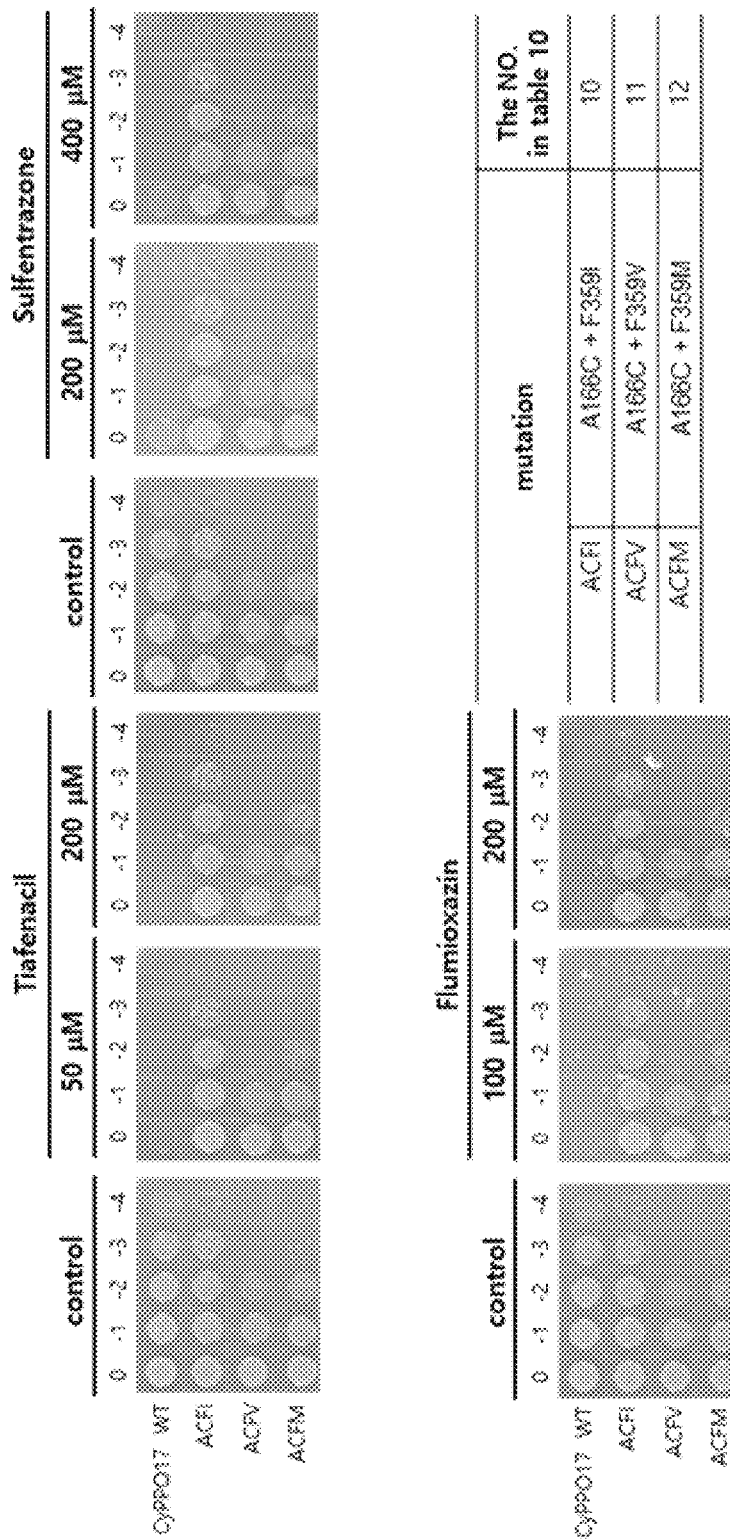
[FIG. 25]

[FIG. 26]
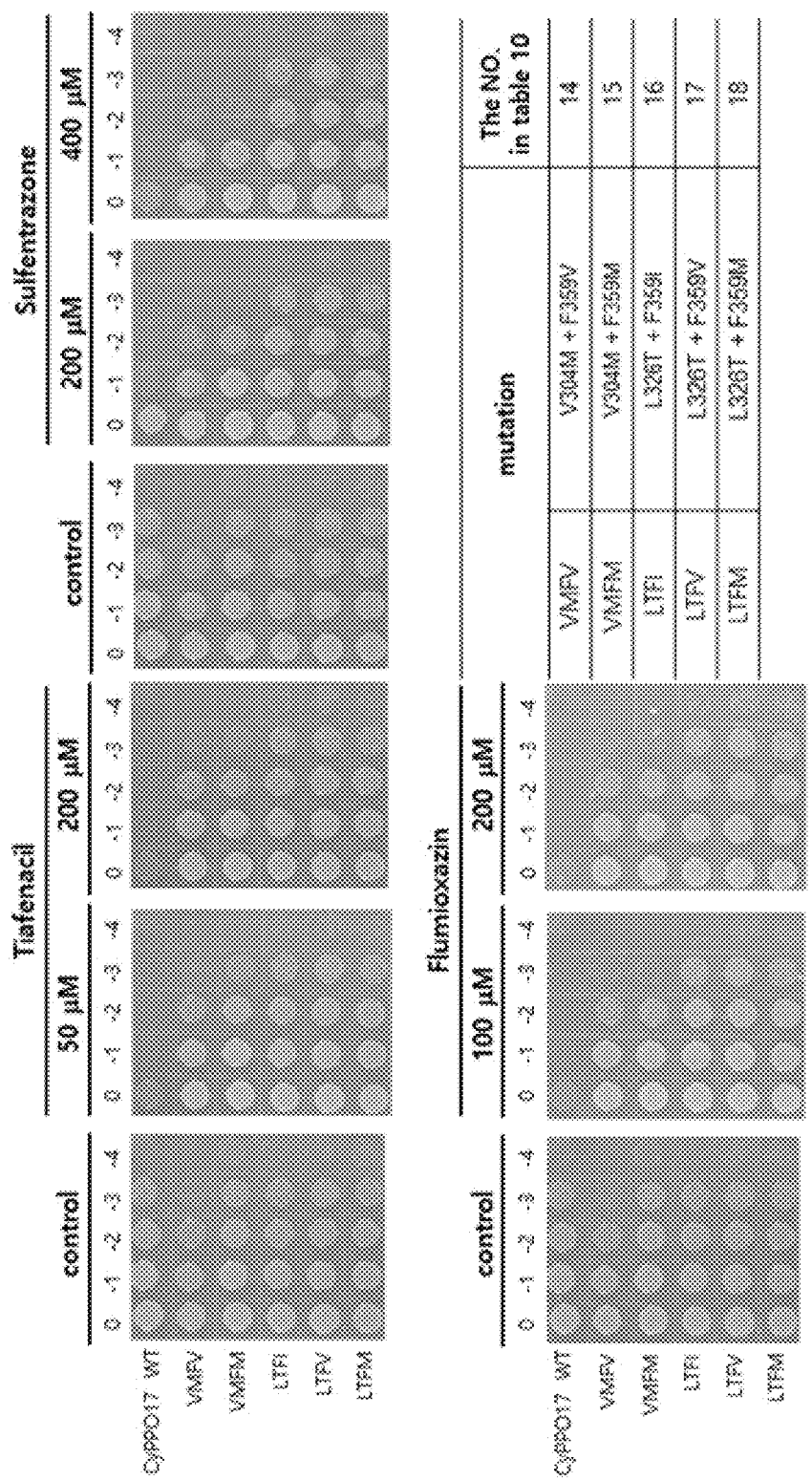

[FIG. 27]
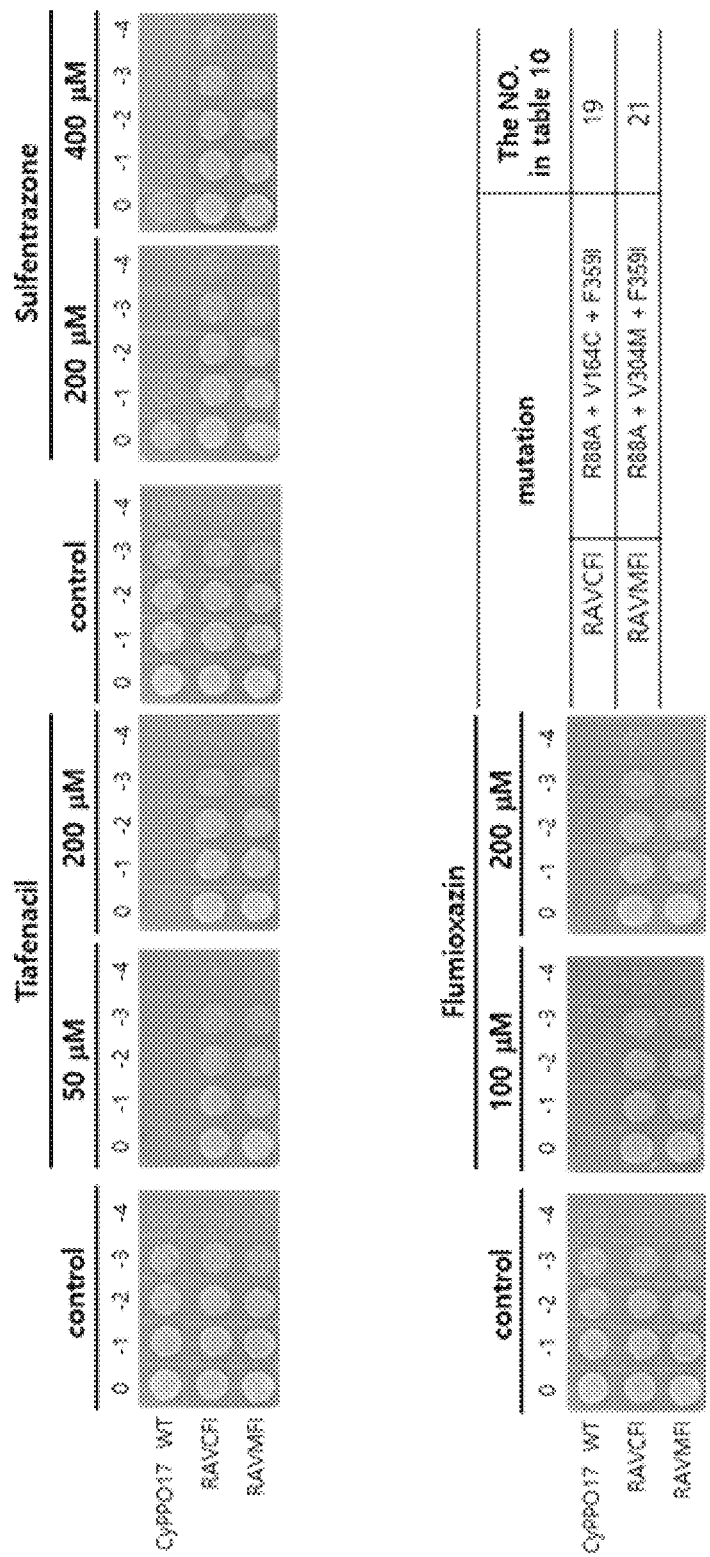

[FIG. 28]
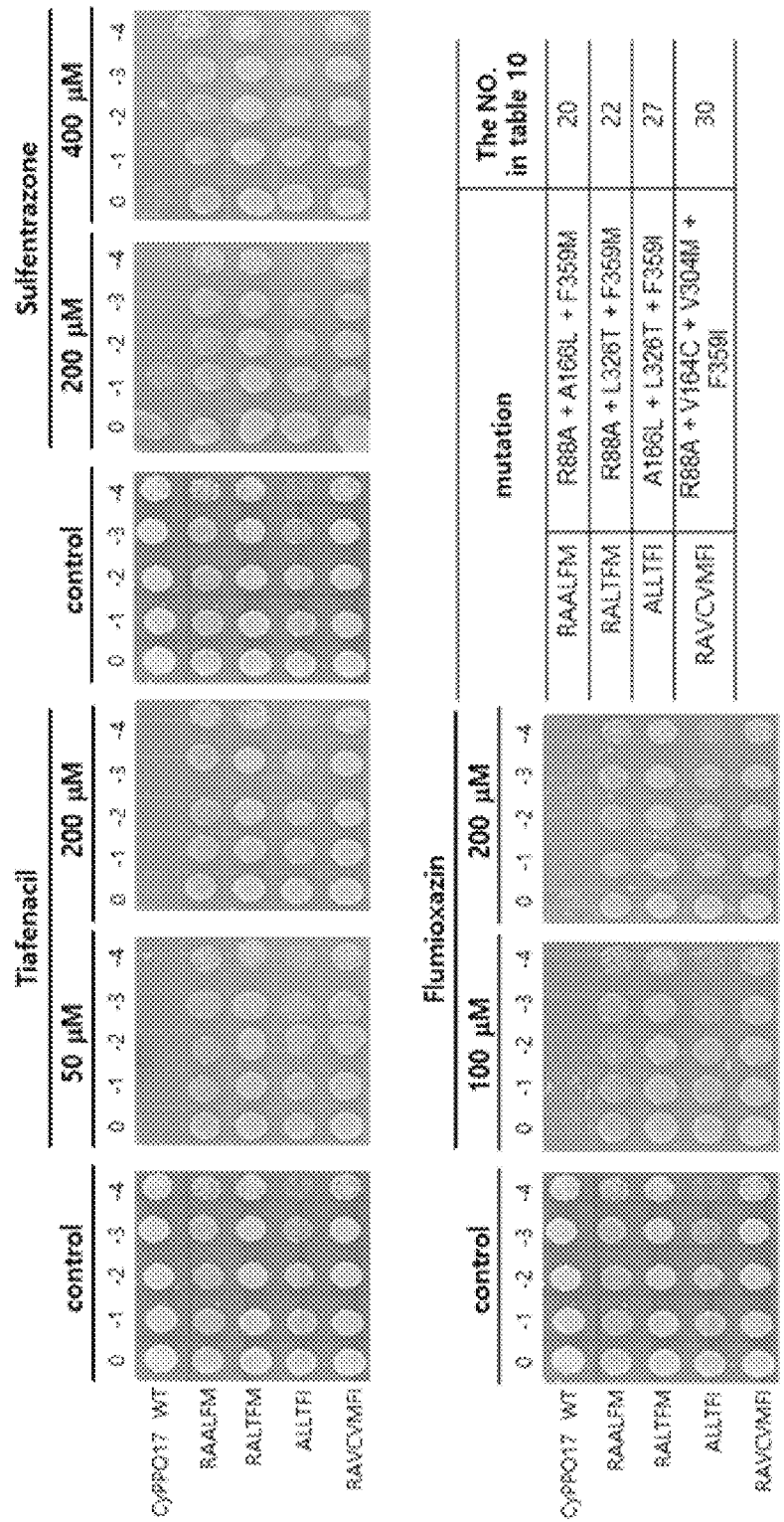

[FIG. 29]

| | mutation | The NO. in table 10 |
|---|---|---|
| VCALFI | V164C + A166L + F359I | 23 |
| VCVMFM | V164C + V304M + F359M | 24 |
| VCLTFI | V164C + L326T + F359I | 25 |
| ALVMFM | A166L + V304M + F359M | 26 |
| VMLTFM | V304M + L326T + F359M | 28 |

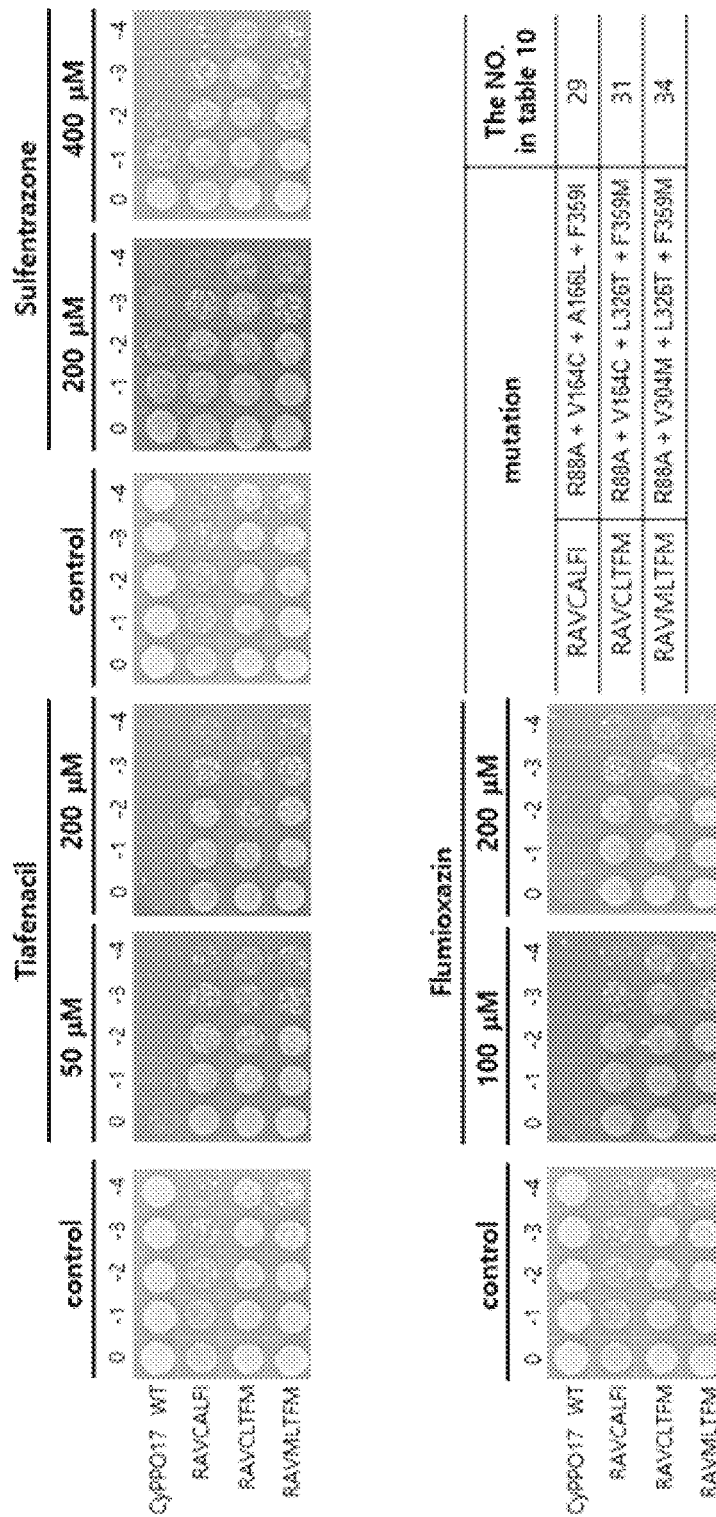
[FIG. 30]

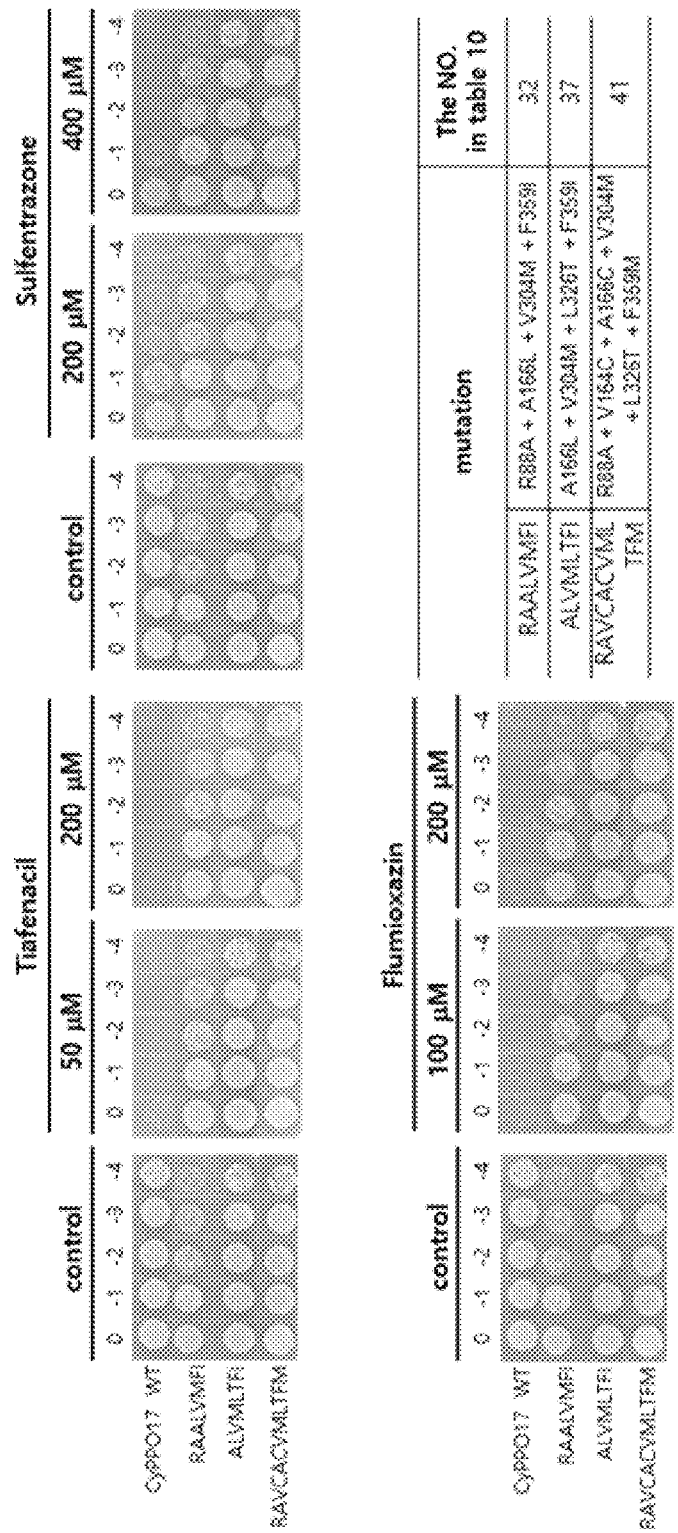
[FIG. 31]

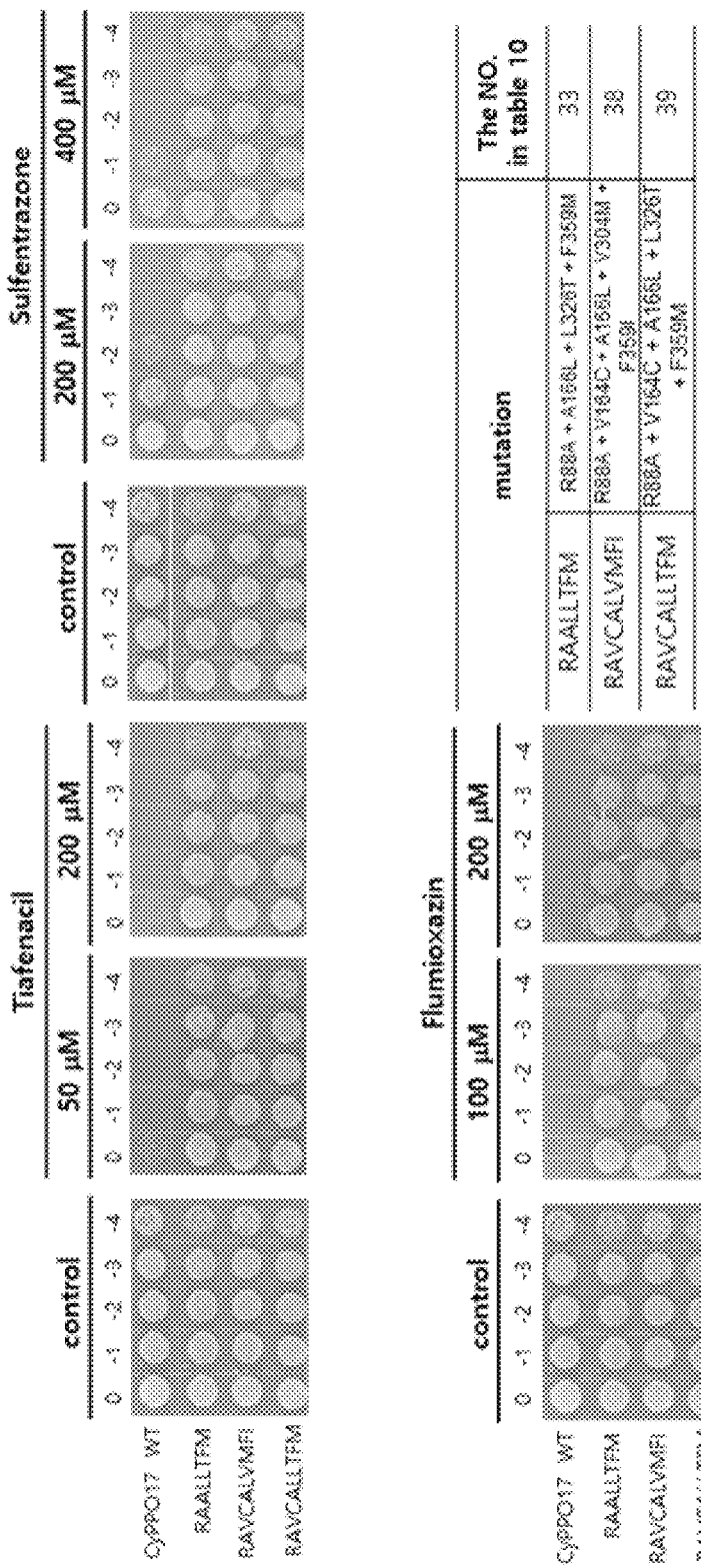
[FIG. 32]

[FIG. 33]
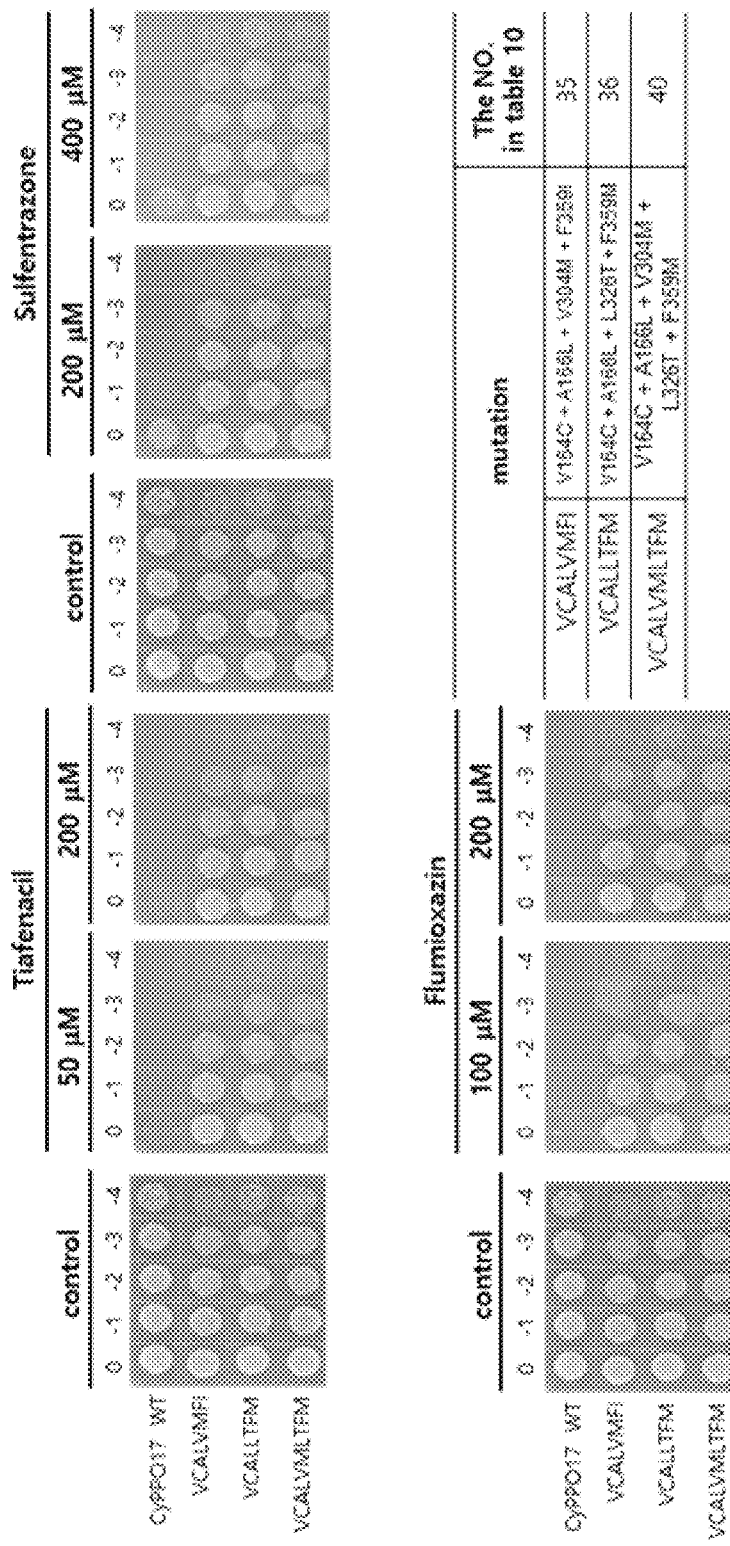

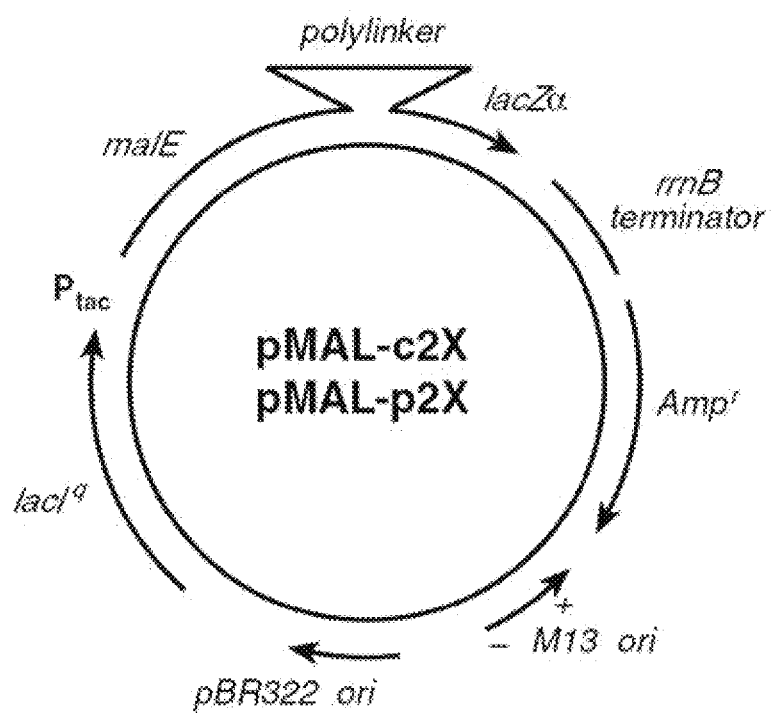
[FIG. 34]

[FIG. 35]
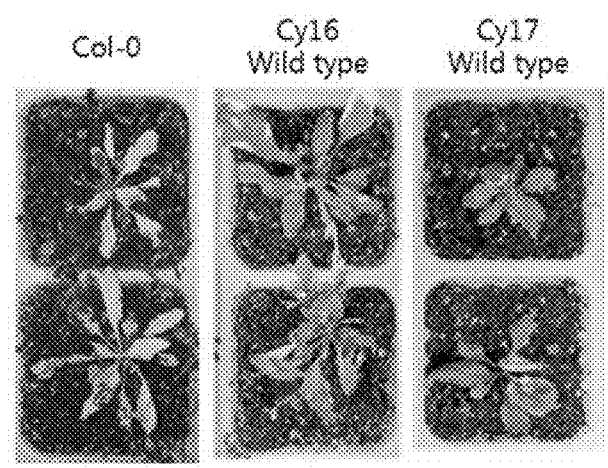

[FIG. 36]
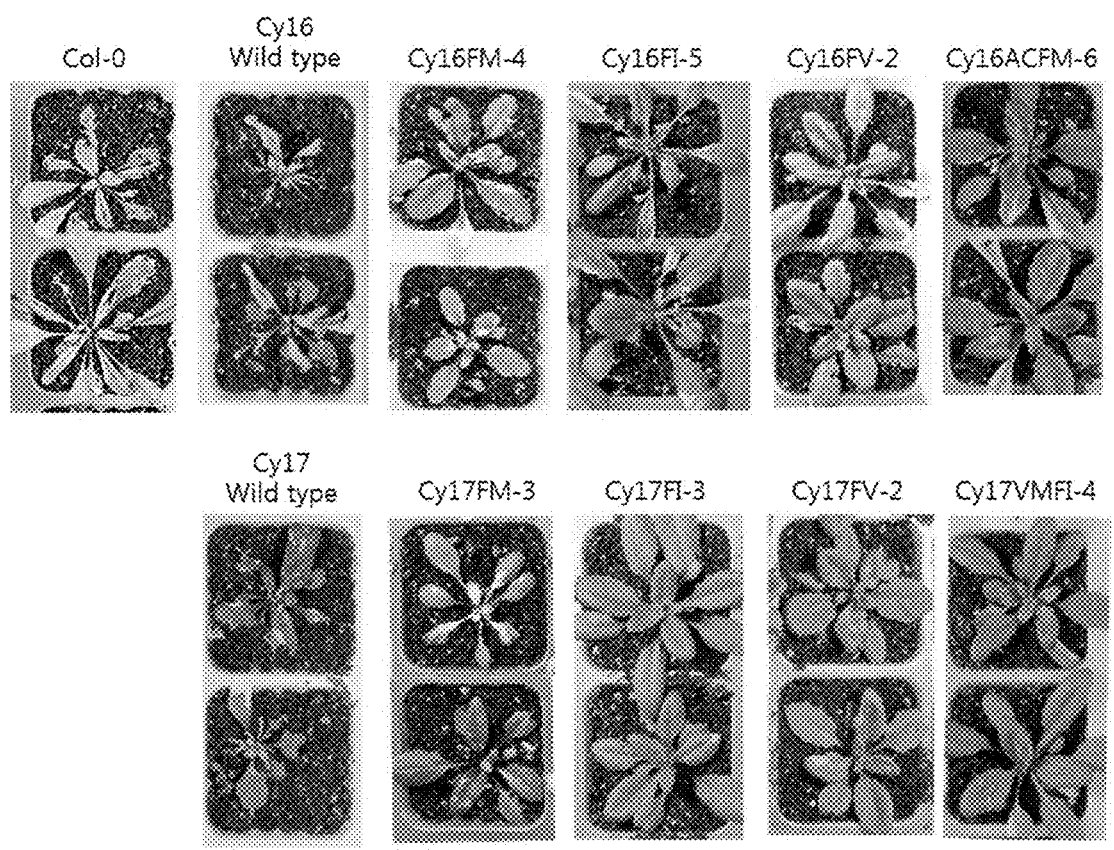

SEQUENCE LISTING

```
<160> NUMBER OF SEQ ID NOS: 90

<210> SEQ ID NO 1
<211> LENGTH: 462
<212> TYPE: PRT
<213> ORGANISM: Artificial Sequence
<220> FEATURE:
<223> OTHER INFORMATION: Synthetic (Protoporphyrinogen IX oxidase
      (CyPPO16) of Spirulina subsalsa)

<400> SEQUENCE: 1
```

```
Met Leu Asp Ser Leu Ile Val Gly Ala Gly Ile Ser Gly Leu Ser Ala
1               5                   10                  15

Ala His Thr Leu Gln Lys Gln Gln Thr Gln Phe Leu Val Thr Glu Ser
                20                  25                  30

Gln Gly Arg Val Gly Gly Asn Ile Thr Thr Asn Arg Gln Gly Asp Tyr
                35                  40                  45

Leu Trp Glu Glu Gly Pro Asn Ser Phe Ala Pro Thr Glu Asp Leu Leu
    50                  55                  60

Arg Leu Ala Val Glu Val Gly Leu Lys Glu Asp Leu Val Phe Ala Asp
65                  70                  75                  80

Arg Arg Leu Pro Arg Phe Val Tyr Trp Asn Gln Gln Leu His Pro Val
                85                  90                  95

Pro Met Ser Pro Pro Ala Ala Leu Lys Thr Gln Leu Leu Ser Glu Ala
                100                 105                 110

Gly Lys Trp Arg Ala Ala Leu Gly Ala Leu Gly Phe Val Gly Gly Leu
                115                 120                 125

Val Gly Arg Glu Glu Glu Thr Val Arg Gln Phe Phe Thr Arg His Leu
                130                 135                 140

Gly Thr Glu Val Thr Glu Arg Leu Val Ala Pro Phe Val Ser Gly Val
145                 150                 155                 160

Tyr Ala Gly Asp Val Asp Gln Leu Ser Ala Gln Ala Ala Phe Arg Arg
                165                 170                 175

Val Phe Glu Phe Ala Gln Leu Gly Gly Gly Leu Ala Ala Gly Gly Ile
                180                 185                 190

Leu Ala Arg Arg Gln Ala Pro Pro Lys Ala Pro Asp Pro Ser Leu
                195                 200                 205

Pro Glu Thr Lys Thr Gly Gln Leu Gly Ser Phe Arg Glu Gly Leu Glu
                210                 215                 220

Met Leu Pro Arg Ala Ile Ala Ser Gln Leu Gly Asp Arg Leu Lys Leu
225                 230                 235                 240

Gln Trp Arg Leu Thr His Leu Glu Ile Thr Pro Gln Gln Thr Tyr Leu
                245                 250                 255

Ala His Phe Asn Thr Pro Asp Gly Pro Gln Gln Ile Ala Thr Arg Thr
                260                 265                 270

Leu Ile Leu Thr Thr Pro Ala Pro Ile Thr Ala Asp Leu Leu Lys Pro
                275                 280                 285

Leu Thr Pro Ala Leu His Gly Val Leu Lys Glu Ile Tyr Tyr Pro Pro
                290                 295                 300

Val Ala Cys Val Val Leu Ala Tyr Pro Arg Ala Ala Ser Ala Arg Pro
305                 310                 315                 320

Leu Glu Gly Phe Gly His Leu Ile Pro Arg Asn Gln Gly Ile Arg Thr
                325                 330                 335

Leu Gly Thr Ile Trp Ser Ser Cys Leu Phe Pro Gly Arg Thr Pro Glu
                340                 345                 350

Gly Glu His Leu Leu Thr Asn Phe Ile Gly Gly Ala Thr Asp Pro Gly
                355                 360                 365

Ile Ala Gln Leu Asp Pro Glu Glu Ile Ala Gln Ala Val His Gln Asp
                370                 375                 380

Leu Cys Lys Ile Leu Ile Arg Pro Glu Phe Thr Pro Lys Ile Leu Ala
385                 390                 395                 400

Val Arg Leu Trp Lys Gln Ala Ile Pro Gln Tyr Thr Leu Gly His Leu
                405                 410                 415
```

```
Gln Arg Leu Ala Thr Leu Glu Gln Glu Leu Ser Lys Phe Pro Gly Leu
            420                 425                 430

His Ile Leu Ala Asn Tyr Thr Asp Gly Val Ala Leu Gly Asp Cys Val
            435                 440                 445

Lys Arg Gly Val Ala Val Ala Gln Lys Ile Arg Ser Arg Glu
    450                 455                 460

<210> SEQ ID NO 2
<211> LENGTH: 1389
<212> TYPE: DNA
<213> ORGANISM: Artificial Sequence
<220> FEATURE:
<223> OTHER INFORMATION: Synthetic (CyPPO16 coding gene from Spirulina
      subsalsa)

<400> SEQUENCE: 2
atgctagact ccctgattgt aggggccgga atatcaggac tctcagctgc acacacctt      60 cagaagcagc agactcagtt tctggtcacg gaatcccaag ggcgtgtggg tggcaatata    120
acgacgaacc gtcaaggtga ttacttgtgg gaggaaggtc ccaattcttt tgcgccaaca    180
gaggaccttt tacgacttgc tgtcgaggta gggctcaaag aggatctggt attcgccgac    240
agacgtctac cgaggtttgt gtattggaac caacagttac ccctgtacc catgagccct    300 cctgcggcgt tgaagactca actactgtca gaagctggaa agtggagagc agcattgggg    360
gcgctgggat tgtaggcgg cctgtcgga agagaggaag aaacggttcg acaatttttt    420
acgcgtcatc ttggtacgga agttaccgag cgtttagtcg caccattgt ctccggtgtg    480 tatgctggcg acgttgatca actatccgcg caagcggcgt tcgtagagt ctttgagttc    540 gcacagctcg gcgggggggtt ggccgcgggg gggattcttg cgcgtcgtca ggcccccca    600 aaagccccac ccgatcccag tttacccgaa accaagactg gcagttagg ctcttttcgt    660 gaagggctag aaatgctccc cagagcaata gccagccaac tcggagacag gttaaagcta    720
cagtggcgac taacgcatct ggagataact ccccaacaaa cttatttggc gcattttaat    780
actccggatg cccgcagca atcgcaaca aggactctga tcctaacaac cccgctcct    840 atcactgctg atcttcttaa acctttgacg cccgcgcttc atggggtgct caaggaaatt    900
tactatcctc cggtagcctg cgtagtccta gcatacccaa gggccgcgag tgcgcgtcca    960
ttggaaggtt ttggtcatct tataccagg aatcagggga taaggactct tggtacaatc    1020
tggtcctcct gtctcttccc gggcaggacg cctgagggtg agcatctgct gaccaatttc    1080
atcggcggcg caacggaccc tggtatagcc cagctagatc ctgaggaaat cgctcaagcc    1140
gtccatcaag atttgtgcaa gatactgatc agaccagaat tcactcccaa atcttagcc    1200 gtcaggctgt ggaagcaagc tattcctcag tatacgctag gcacttgca gcgacttgca    1260 accttggaac aggagttgtc caagtttcct gggcttcata tcctagctaa ttatacggat    1320
ggtgttgcgc tcggcgattg cgtcaaacgt ggagttgcag tggctcaaaa aattagaagc    1380
agggagtga                                                            1389

<210> SEQ ID NO 3
<211> LENGTH: 466
<212> TYPE: PRT
<213> ORGANISM: Artificial Sequence
<220> FEATURE:
<223> OTHER INFORMATION: Synthetic (Protoporphyrinogen IX oxidase
      (CyPPO17) of Thermosynechococcus sp. NK55a)

<400> SEQUENCE: 3
```

Met Glu Val Asp Val Ala Ile Val Gly Gly Leu Ser Gly Leu Ser
1               5                   10                  15

Val Ala Trp Arg Leu Gln Gln Ser Ala Pro Gln Tyr Ser Gly Val Leu
            20                  25                  30

Leu Glu Ala Ser Asp Arg Leu Gly Gly Asn Ile Thr Thr Gln Gly Ala
                35                  40                  45

Glu Gly Phe Val Trp Glu Leu Gly Pro Asn Ser Phe Ala Pro Thr Pro
50                  55                  60

Ala Leu Leu Gln Leu Ile Ala Glu Val Gly Leu His Ser Glu Leu Ile
65                  70                  75                  80

Arg Gly Asp Arg His Leu Pro Arg Tyr Ile Tyr Trp Arg Gly Glu Leu
                85                  90                  95

Tyr Pro Leu Glu Pro Thr Arg Pro Leu Ala Leu Ala Thr Ser Asn Leu
                100                 105                 110

Leu Ser Pro Trp Gly Lys Val Arg Ala Ala Leu Gly Ala Leu Gly Phe
            115                 120                 125

Val Pro Pro Tyr Leu Gly Ser Gly Asp Glu Ser Val Asn Ser Phe Phe
            130                 135                 140

Arg Arg His Leu Gly Gln Glu Val Ala Glu Arg Leu Val Ala Pro Phe
145                 150                 155                 160

Val Ser Gly Val Tyr Ala Gly Asp Pro Gln Gln Leu Ser Ala Ala Ala
                165                 170                 175

Ala Phe Arg Arg Ile Ala Gln Leu Glu Lys Leu Gly Gly Gly Leu Ile
                180                 185                 190

Ala Gly Ala Leu Arg Leu Arg Arg Gln Gln Pro Pro Lys Pro Arg Pro
            195                 200                 205

Pro Ala Glu Val Gln Met Arg Pro Gly Glu Leu Gly Ser Phe Lys Glu
            210                 215                 220

Gly Leu Ala Ala Leu Pro Arg Ala Ile Ala Gln Gln Leu Lys Ala Pro
225                 230                 235                 240

Val His Leu Gln Thr Pro Val Glu Ala Ile Thr Pro Glu Pro Asn Gly
                245                 250                 255

Gly Tyr Leu Leu Arg Ser Gly Glu Gln Thr Trp Gln Ala Arg Ser Val
                260                 265                 270

Val Leu Ala Thr Pro Ala Tyr Gln Thr Ala Ala Leu Val Ala Pro Phe
            275                 280                 285

Gln Pro Ala Ile Ala Arg Val Leu Ala Ala Ile Pro Tyr Pro Thr Val
            290                 295                 300

Ala Cys Val Val Leu Ala Tyr Pro Ala Gly Leu Gly Arg Ser Val Arg
305                 310                 315                 320

Pro Gly Phe Gly Val Leu Ile Pro Arg Gly Gln Gly Ile Arg Thr Leu
                325                 330                 335

Gly Thr Ile Trp Ser Ser Cys Leu Phe Pro Gln Arg Thr Pro Ala Gly
                340                 345                 350

Trp Gln Val Phe Thr Ser Phe Ile Gly Gly Ala Thr Asp Pro Asp Leu
            355                 360                 365

Ala Ser Leu Arg Glu Glu Ala Ile Val Gln Val Gln Gln Asp Leu
            370                 375                 380

Thr Arg Leu Leu Asp Leu Pro Ala Ala Lys Ala Arg Leu Leu Gly Met
385                 390                 395                 400

Lys Val Trp Arg Arg Ala Ile Pro Gln Tyr Leu Val Gly Tyr Pro Gln
                405                 410                 415

Gln Trp Gln Gln Val Thr His Ala Leu Ser Gln Thr Pro Gly Leu Phe

Leu Cys Ser Asn Tyr Ala Glu Gly Val Ala Leu Gly Asp Arg Val Glu
      420                 425                 430

His Gly Asn Arg Thr Ala Ala Ala Val Ala Ala Tyr Leu Ser Gly Gly
      435                 440                 445

Gln Ser
450                 455                 460

465

<210> SEQ ID NO 4
<211> LENGTH: 1401
<212> TYPE: DNA
<213> ORGANISM: Artificial Sequence
<220> FEATURE:
<223> OTHER INFORMATION: Synthetic (CyPPO17 coding gene from Thermosynechococcus sp. NK55a)

<400> SEQUENCE: 4

| | | | | |
|---|---|---|---|---|
| atggaggtcg | atgttgcaat | tgtcggcggc | ggcctgtcag | gcttgagcgt tgcctggcgt | 60 |
| ctccagcagt | ctgctcctca | atacagtggc | gttctattgg | aagcgtcaga ccgtctaggt | 120 |
| gggaacatta | ctacgcaagg | ggcagagggg | ttcgtgtggg | aactaggccc taacagcttc | 180 |
| gctccgactc | ccgcgctttt | acagcttata | gcagaagtag | gcttcactc cgagcttata | 240 |
| cgtggcgatc | gacatctacc | gcgatacatt | tattggcgag | gcgaacttta tccattggag | 300 |
| ccgaccaggc | cgcttgcttt | ggcaacaagc | aatctcctct | ctccatgggg taaggtcaga | 360 |
| gcagcgttgg | gcgccctcgg | gtttgtcccc | ccgtatctcg | gatctggcga tgaatccgtt | 420 |
| aattcatttt | tccgacgaca | cctaggtcag | gaggtagccg | aacgtctggt ggcacctttc | 480 |
| gtctctggcg | tgtatgcggg | agatccccag | caactgtccg | ccgccgctgc atttagacga | 540 |
| atagcgcagc | tggaaaaact | aggtggggga | ctcatagcag | gagcattgag gctgaggaga | 600 |
| cagcaacccc | ccaaacccag | gccccggca | gaggttcaaa | tgcgacccgg tgagttgggg | 660 |
| tctttcaaag | agggattggc | cgccttgcca | cgtgcaatag | ctcaacagct gaaagcacca | 720 |
| gtgcacctac | aaaccccagt | cgaagcaatc | acgccggagc | caacggagg ttatctactc | 780 |
| agatccggcg | aacagacttg | gcaagcgaga | agcgtcgtcc | tagcaacacc tgcctatcag | 840 |
| accgcagcat | tagtggcgcc | gtttcaacct | gcaatagcgc | gagtgttagc ggccattccg | 900 |
| tatccaacag | tggcctgtgt | agtactcgcc | tatcccgcgg | gactaggcag gtcagtacga | 960 |
| ccaggctttg | gcgtccttat | accccgtggc | caaggtatcc | gtacactcgg cactatatgg | 1020 |
| tctagctgct | tatttccaca | gcgaactcca | gctgggtggc | aagtttttac ttcattcatc | 1080 |
| ggtggagcaa | cagatccgga | cctcgcctca | ctgagggaag | aagcgatcgt tcaacaggtg | 1140 |
| caacaggact | tgacccgtct | acttgatctt | cctgccgcca | aggcgagact cctcggtatg | 1200 |
| aaagtgtggc | gaagggcgat | cccacaatac | ttggtagggt | atccacagca atggcagcaa | 1260 |
| gtaacccatg | cccttagtca | gacgccgggc | cttttcctgt | gtagtaacta cgccgagggc | 1320 |
| gtggcattag | gcgacagggt | tgaacatggt | aacaggaccg | ctgcggcagt ggccgcgtac | 1380 |
| ctgagtgggg | ggcaatcctg | a | | | 1401 |

<210> SEQ ID NO 5
<211> LENGTH: 467
<212> TYPE: PRT
<213> ORGANISM: Artificial Sequence
<220> FEATURE:
<223> OTHER INFORMATION: Synthetic (Protoporphyrinogen IX oxidase (CyPPO10) of Thermosynechococcus elongatus BP-1)

-continued

<400> SEQUENCE: 5

Met Ile Glu Val Asp Val Ala Ile Val Gly Gly Gly Leu Ser Gly Leu
1               5                   10                  15

Ser Val Ala Trp Arg Leu Gln Arg Ser Ala Pro His Tyr Ser Gly Val
            20                  25                  30

Leu Leu Glu Ala Ser Asp Arg Leu Gly Gly Asn Ile Thr Thr Gln Ala
        35                  40                  45

Ala Glu Gly Phe Val Trp Glu Leu Gly Pro Asn Ser Phe Ala Pro Thr
    50                  55                  60

Pro Ala Leu Leu Gln Leu Ile Ala Glu Val Gly Leu His Ser Glu Leu
65                  70                  75                  80

Ile Arg Gly Asp Arg His Leu Pro Arg Tyr Ile Tyr Trp Arg Gly Glu
                85                  90                  95

Leu Tyr Pro Leu Glu Pro Thr Arg Pro Leu Ala Leu Ala Thr Ser Asn
            100                 105                 110

Leu Leu Ser Pro Trp Gly Lys Val Arg Ala Ala Leu Gly Ala Leu Gly
        115                 120                 125

Phe Val Pro Pro Tyr Leu Gly Ser Gly Asp Glu Ser Val Asp Ser Phe
    130                 135                 140

Phe Arg Arg His Leu Gly Gln Glu Val Ala Glu Arg Leu Val Ala Pro
145                 150                 155                 160

Phe Val Ser Gly Val Tyr Ala Gly Asp Pro Gln Gln Leu Ser Ala Ala
                165                 170                 175

Ala Ala Phe Arg Arg Ile Ala Gln Leu Glu Lys Leu Gly Gly Ser Leu
            180                 185                 190

Ile Ala Gly Ala Leu Arg Leu Arg Arg Gln Gln Pro Pro Gln Pro Lys
        195                 200                 205

Pro Pro Ala Gln Val Gln Met Arg Pro Gly Glu Leu Gly Ser Phe Arg
    210                 215                 220

Glu Gly Leu Ala Ala Leu Pro Arg Ala Ile Ala Gln Gln Leu Lys Ala
225                 230                 235                 240

Pro Leu His Leu Gln Thr Pro Val Glu Ala Ile Thr Pro Glu Pro Lys
                245                 250                 255

Gly Gly Tyr Leu Leu Arg Ser Gly Glu Gln Thr Trp His Ala Arg Ser
            260                 265                 270

Val Val Leu Ala Thr Pro Ala Tyr Gln Thr Ala Glu Leu Val Ala Pro
        275                 280                 285

Phe Gln Pro Ala Ile Ala Arg Ala Leu Ala Thr Ile Pro Tyr Pro Thr
    290                 295                 300

Val Ala Cys Val Val Leu Ala Tyr Pro Ala Gly Leu Gly Arg Ser Val
305                 310                 315                 320

Arg Pro Gly Phe Gly Val Leu Val Pro Arg Gly Gln Gly Ile Arg Thr
                325                 330                 335

Leu Gly Thr Ile Trp Ser Ser Cys Leu Phe Pro Gln Arg Thr Pro Ala
            340                 345                 350

Gly Trp Gln Val Phe Thr Ser Phe Ile Gly Gly Ala Thr Asp Pro Asp
        355                 360                 365

Leu Ala Ser Leu Arg Glu Glu Ala Ile Val Glu Gln Val Gln Gln Asp
    370                 375                 380

Leu Thr Arg Leu Leu Asp Leu Pro Ala Lys Ala Arg Leu Leu Gly
385                 390                 395                 400

Met Lys Val Trp Arg Arg Ala Ile Pro Gln Tyr Ile Val Gly Tyr Pro
                405                 410                 415

Gln Gln Trp Gln Gln Val Thr His Ala Leu Thr Gln Thr Pro Gly Leu
                420                 425                 430

Phe Leu Cys Ser Asn Tyr Ala Glu Gly Val Ala Leu Gly Asp Arg Val
            435                 440                 445

Glu His Gly Asn Arg Thr Ala Ala Val Ala Ala Tyr Leu Ala Gly
450                 455                 460

Gly Gln Ser
465

<210> SEQ ID NO 6
<211> LENGTH: 1404
<212> TYPE: DNA
<213> ORGANISM: Artificial Sequence
<220> FEATURE:
<223> OTHER INFORMATION: Synthetic (CyPPO10 coding gene)

<400> SEQUENCE: 6

| | |
|---|---|
| atgattgaag tggatgtggc tattgttggt ggtggtctta gtggattgtc agtggcttgg | 60 |
| agattacaga ggagtgctcc tcattattct ggagttcttc ttgaggcttc tgatagactt | 120 |
| ggaggtaata tcactacaca agctgctgaa ggatttgtgt gggagcttgg tccaaacagt | 180 |
| ttcgctccta ctccagcact cttacagttg attgctgaag ttggactcca ttctgagtta | 240 |
| atcagaggag ataggcacct tccaagatat atatactgga ggggagaact ttatcctttg | 300 |
| gagccaacta ggcctcttgc tttggcaaca tcaaatcttt gagtccttg gggaaaggtt | 360 |
| agagctgcac tcggagcttt aggttttgtg cctccatatc ttggatctgg agatgaaagt | 420 |
| gttgattctt tctttagaag gcatcttgga caagaagttg ctgagagatt ggtggcacca | 480 |
| tttgtttcag gagtgtacgc tggagatcct aacagctttt ctgctgctgc tgcttttaga | 540 |
| aggattgctc aacttgagaa gttgggaggt tcattgatcg ctggagcact cagattaaga | 600 |
| aggcaacagc ctccacagcc aaaacctcca gctcaagtgc agatgagacc tggagaactc | 660 |
| ggtagtttta gggagggtct cgctgcatta cctagagcta tcgcacaaca gttgaaggca | 720 |
| ccacttcatt tgcaaacacc tgttgaagct attaccctg agccaaaagg aggttatctc | 780 |
| ttaaggagtg gtgaacagac ttggcacgct agatcagttg tgttggctac tccagcatac | 840 |
| caaactgctg aacttgttgc accattccag cctgctatcg ctagagcttt ggctaccata | 900 |
| ccttatccaa ctgttgcttg tgttgtgctt gcttaccctg ctggattggg tagatcagtt | 960 |
| agacctggat tggtgttttt ggtgcctaga ggacaaggta aggacact cggaaccatt | 1020 |
| tggtcttcat gcttattccc acaaagaact cctgctggtt ggcaggtttt tacctctttc | 1080 |
| ataggaggtg ctactgatcc tgatcttgca tcattgagag aagaggctat tgttgaacaa | 1140 |
| gtgcaacagg atctcacaag gcttcttgat cttcctgctg caaaggcaag actcttgggt | 1200 |
| atgaaggttt ggagaagggc tattccacaa tatatcgttg gttaccctca acagtggcaa | 1260 |
| caggtgacac acgctcttac ccagactcct ggtctcttct tatgttcaaa ctacgctgag | 1320 |
| ggagttgcat tggagataga gtggaacac ggaaatagga ctgctgctgc tgtggctgct | 1380 |
| tacctcgctg gtggacaatc ataa | 1404 |

<210> SEQ ID NO 7
<211> LENGTH: 1389
<212> TYPE: DNA
<213> ORGANISM: Artificial Sequence
<220> FEATURE:
<223> OTHER INFORMATION: Synthetic (Optimized codon encoding CyPPO16)

```
<400> SEQUENCE: 7
atgctagact ccctgattgt aggggccgga atatcaggac tctcagctgc acacacccct     60
cagaagcagc agactcagtt tctggtcacg gaatcccaag ggcgtgtggg tggcaatata    120
acgacgaacc gtcaaggtga ttacttgtgg gaggaaggtc ccaattcttt tgcgccaaca    180
gaggaccttt tacgacttgc tgtcgaggta gggctcaaag aggatctggt attcgccgac    240
agacgtctac cgaggtttgt gtattggaac caacagttac accctgtacc catgagccct    300
cctgcggcgt tgaagactca actactgtca gaagctggaa agtggagagc agcattgggg    360
gcgctgggat ttgtaggcgg ccttgtcgga agagaggaag aaacggttcg acaattttt     420 acgcgtcatc ttggtacgga agttaccgag cgtttagtcg caccatttgt ctccggtgtg    480
tatgctggcg acgttgatca actatccgcg caagcggcgt ttcgtagagt ctttgagttc    540
gcacagctcg gcgggggggtt ggccgcgggg gggattcttg cgcgtcgtca ggcccccca     600 aaagccccac ccgatcccag tttacccgaa accaagactg ggcagttagg ctcttttcgt    660
gaagggctag aaatgctccc cagagcaata gccagccaac tcggagacag gttaaagcta    720
cagtggcgac taacgcatct ggagataact ccccaacaaa cttatttggc gcattttaat    780
actccggatg gcccgcagca aatcgcaaca aggactctga tcctaacaac cccgctcct     840 atcactgctg atcttcttaa accttttgacg cccgcgcttc atggggtgct caaggaaatt    900
tactatcctc cggtagcctg cgtagtccta gcataccccaa gggccgcgag tgcgcgtcca    960
ttggaaggtt ttggtcatct tatacccagg aatcagggga taaggactct tggtacaatc   1020
tggtcctcct gtctcttccc gggcaggacg cctgagggtg agcatctgct gaccaatttc   1080
atcggcggcg caacggaccc tggtatagcc cagctagatc ctgaggaaat cgctcaagcc   1140
gtccatcaag atttgtgcaa gatactgatc agaccagaat tcactcccaa aatcttagcc   1200
gtcaggctgt ggaagcaagc tattcctcag tatacgctag ggcacttgca gcgacttgca   1260
accttggaac aggagttgtc caagtttcct gggcttcata tcctagctaa ttatacggat   1320
ggtgttgcgc tcggcgattg cgtcaaacgt ggagttgcag tggctcaaaa aattagaagc   1380
agggagtga                                                          1389

<210> SEQ ID NO 8
<211> LENGTH: 1401
<212> TYPE: DNA
<213> ORGANISM: Artificial Sequence
<220> FEATURE:
<223> OTHER INFORMATION: Synthetic (Optimized codon encoding CyPPO17)

<400> SEQUENCE: 8
atggaggtcg atgttgcaat tgtcggcggc ggcctgtcag gcttgagcgt tgcctggcgt     60
ctccagcagt ctgctcctca atacagtggc gttctattgg aagcgtcaga ccgtctaggt    120
gggaacatta ctacgcaagg ggcagagggg ttcgtgtggg aactaggccc taacagcttc    180
gctccgactc ccgcgctttt acagcttata gcagaagtag gcttcactc cgagcttata    240 cgtggcgatc gacatctacc gcgatacatt tattggcgag gcgaacttta tccattggag    300
ccgaccaggc cgcttgcttt ggcaacaagc aatctcctct ctccatgggg taaggtcaga    360
gcagcgttgg gcgccctcgg gtttgtcccc ccgtatctcg gatctggcga tgaatccgtt    420
aattcatttt tccgacgaca cctaggtcag gaggtagccg aacgtctggt ggcacctttc    480
gtctctggcg tgtatgcggg agatccccag caactgtccg ccgccgctgc atttagacga    540
atagcgcagc tggaaaaaact aggtgggggga ctcatagcag gagcattgag gctgaggaga    600
```

```
cagcaaccce ccaaacccag gcccccggca gaggttcaaa tgcgacccgg tgagttgggg      660
tctttcaaag agggattggc cgccttgcca cgtgcaatag ctcaacagct gaaagcacca      720
gtgcacctac aaaccccagt cgaagcaatc acgccggagc ccaacggagg ttatctactc      780
agatccggcg aacagacttg gcaagcgaga agcgtcgtcc tagcaacacc tgcctatcag      840
accgcagcat tagtggcgcc gtttcaacct gcaatagcgc gagtgttagc ggccattccg      900
tatccaacag tggcctgtgt agtactcgcc tatcccgcgg gactaggcag gtcagtacga      960
ccaggctttg gcgtccttat accccgtggc caaggtatcc gtacactcgg cactatatgg     1020
tctagctgct tatttccaca gcgaactcca gctgggtggc aagttttttac ttcattcatc     1080 ggtggagcaa cagatccgga cctcgcctca ctgagggaag aagcgatcgt caacaggtg      1140 caacaggact tgacccgtct acttgatctt cctgccgcca aggcgagact cctcggtatg     1200
aaagtgtggc gaagggcgat cccacaatac ttggtagggt atccacagca atggcagcaa     1260
gtaacccatg cccttagtca gacgccgggc ctttcctgt gtagtaacta cgccgagggc      1320
gtggcattag gcgacagggt tgaacatggt aacaggaccg ctgcggcagt ggccgcgtac     1380
ctgagtgggg ggcaatcctg a                                               1401

<210> SEQ ID NO 9
<211> LENGTH: 30
<212> TYPE: DNA
<213> ORGANISM: Artificial Sequence
<220> FEATURE:
<223> OTHER INFORMATION: Synthetic (CyPPO16_XbaIF primer)

<400> SEQUENCE: 9
cccctctaga atgctagact ccctgattgt                                         30

<210> SEQ ID NO 10
<211> LENGTH: 31
<212> TYPE: DNA
<213> ORGANISM: Artificial Sequence
<220> FEATURE:
<223> OTHER INFORMATION: Synthetic (CyPPO16_XhoIR primer)

<400> SEQUENCE: 10
ccccctcgag ctccctgctt ctaatttttt g                                       31

<210> SEQ ID NO 11
<211> LENGTH: 30
<212> TYPE: DNA
<213> ORGANISM: Artificial Sequence
<220> FEATURE:
<223> OTHER INFORMATION: Synthetic (CyPPO17_XbaIF primer)

<400> SEQUENCE: 11
cccctctaga atggaggtcg atgttgcaat                                         30

<210> SEQ ID NO 12
<211> LENGTH: 30
<212> TYPE: DNA
<213> ORGANISM: Artificial Sequence
<220> FEATURE:
<223> OTHER INFORMATION: Synthetic (CyPPO17_XhoIR primer)

<400> SEQUENCE: 12
ccccctcgag ggattgcccc ccactcaggt                                         30

<210> SEQ ID NO 13
```

```
<211> LENGTH: 33
<212> TYPE: DNA
<213> ORGANISM: Artificial Sequence
<220> FEATURE:
<223> OTHER INFORMATION: Synthetic (F360M forward primer)

<400> SEQUENCE: 13
catctgctga ccaatatgat cggcggcgca acg                            33

<210> SEQ ID NO 14
<211> LENGTH: 33
<212> TYPE: DNA
<213> ORGANISM: Artificial Sequence
<220> FEATURE:
<223> OTHER INFORMATION: Synthetic (F360M reverse primer)

<400> SEQUENCE: 14
cgttgcgccg ccgatcatat tggtcagcag atg                            33

<210> SEQ ID NO 15
<211> LENGTH: 32
<212> TYPE: DNA
<213> ORGANISM: Artificial Sequence
<220> FEATURE:
<223> OTHER INFORMATION: Synthetic (F360L forward primer)

<400> SEQUENCE: 15
gaccaatttg atcggcggcg caacggaccc tg                             32

<210> SEQ ID NO 16
<211> LENGTH: 32
<212> TYPE: DNA
<213> ORGANISM: Artificial Sequence
<220> FEATURE:
<223> OTHER INFORMATION: Synthetic (F360L reverse primer)

<400> SEQUENCE: 16
cgccgatcaa attggtcagc agatgctcac cc                             32

<210> SEQ ID NO 17
<211> LENGTH: 33
<212> TYPE: DNA
<213> ORGANISM: Artificial Sequence
<220> FEATURE:
<223> OTHER INFORMATION: Synthetic (F360I forward primer)

<400> SEQUENCE: 17
catctgctga ccaatatcat cggcggcgca acg                            33

<210> SEQ ID NO 18
<211> LENGTH: 33
<212> TYPE: DNA
<213> ORGANISM: Artificial Sequence
<220> FEATURE:
<223> OTHER INFORMATION: Synthetic (F360I reverse primer)

<400> SEQUENCE: 18
cgttgcgccg ccgatgatat tggtcagcag atg                            33

<210> SEQ ID NO 19
<211> LENGTH: 33
<212> TYPE: DNA
<213> ORGANISM: Artificial Sequence
<220> FEATURE:
<223> OTHER INFORMATION: Synthetic (F360C forward primer)

<400> SEQUENCE: 19
```
tgaccaattg catcggcggc gcaacggacc ctg                           33

<210> SEQ ID NO 20
<211> LENGTH: 32
<212> TYPE: DNA
<213> ORGANISM: Artificial Sequence
<220> FEATURE:
<223> OTHER INFORMATION: Synthetic (F360C reverse primer)

<400> SEQUENCE: 20
cgccgatgca attggtcagc agatgctcac cc                            32

<210> SEQ ID NO 21
<211> LENGTH: 32
<212> TYPE: DNA
<213> ORGANISM: Artificial Sequence
<220> FEATURE:
<223> OTHER INFORMATION: Synthetic (F360V forward primer)

<400> SEQUENCE: 21
ctgaccaatg tcatcggcgg cgcaacggac cc                            32

<210> SEQ ID NO 22
<211> LENGTH: 33
<212> TYPE: DNA
<213> ORGANISM: Artificial Sequence
<220> FEATURE:
<223> OTHER INFORMATION: Synthetic (F360V reverse primer)

<400> SEQUENCE: 22
gccgatgaca ttggtcagca gatgctcacc ctc                           33

<210> SEQ ID NO 23
<211> LENGTH: 33
<212> TYPE: DNA
<213> ORGANISM: Artificial Sequence
<220> FEATURE:
<223> OTHER INFORMATION: Synthetic (F360T forward primer)

<400> SEQUENCE: 23
catctgctga ccaataccat cggcggcgca acg                           33

<210> SEQ ID NO 24
<211> LENGTH: 33
<212> TYPE: DNA
<213> ORGANISM: Artificial Sequence
<220> FEATURE:
<223> OTHER INFORMATION: Synthetic (F360T reverse primer)

<400> SEQUENCE: 24
cgttgcgccg ccgatggtat tggtcagcag atg                           33

<210> SEQ ID NO 25
<211> LENGTH: 33
<212> TYPE: DNA
<213> ORGANISM: Artificial Sequence
<220> FEATURE:
<223> OTHER INFORMATION: Synthetic (V305L forward primer)

<400> SEQUENCE: 25
tatcctccgc tagcctgcgt agtcctagca tac                           33

<210> SEQ ID NO 26
<211> LENGTH: 32
<212> TYPE: DNA

<213> ORGANISM: Artificial Sequence
<220> FEATURE:
<223> OTHER INFORMATION: Synthetic (V305L reverse primer)

<400> SEQUENCE: 26
cgcaggctag cggaggatag taaatttcct tg                32

<210> SEQ ID NO 27
<211> LENGTH: 33
<212> TYPE: DNA
<213> ORGANISM: Artificial Sequence
<220> FEATURE:
<223> OTHER INFORMATION: Synthetic (A162L forward primer)

<400> SEQUENCE: 27
gtctccggtg tgtatcttgg cgacgttgat caa               33

<210> SEQ ID NO 28
<211> LENGTH: 33
<212> TYPE: DNA
<213> ORGANISM: Artificial Sequence
<220> FEATURE:
<223> OTHER INFORMATION: Synthetic (A162L reverse primer)

<400> SEQUENCE: 28
ttgatcaacg tcgccaagat acacaccgga gac               33

<210> SEQ ID NO 29
<211> LENGTH: 33
<212> TYPE: DNA
<213> ORGANISM: Artificial Sequence
<220> FEATURE:
<223> OTHER INFORMATION: Synthetic (A162C forward primer)

<400> SEQUENCE: 29
gtctccggtg tgtattgtgg cgacgttgat caa               33

<210> SEQ ID NO 30
<211> LENGTH: 33
<212> TYPE: DNA
<213> ORGANISM: Artificial Sequence
<220> FEATURE:
<223> OTHER INFORMATION: Synthetic (A162C reverse primer)

<400> SEQUENCE: 30
ttgatcaacg tcgccacaat acacaccgga gac               33

<210> SEQ ID NO 31
<211> LENGTH: 33
<212> TYPE: DNA
<213> ORGANISM: Artificial Sequence
<220> FEATURE:
<223> OTHER INFORMATION: Synthetic (V305M forward primer)

<400> SEQUENCE: 31
atttactatc ctccgatggc ctgcgtagtc cta               33

<210> SEQ ID NO 32
<211> LENGTH: 33
<212> TYPE: DNA
<213> ORGANISM: Artificial Sequence
<220> FEATURE:
<223> OTHER INFORMATION: Synthetic (V305M reverse primer)

<400> SEQUENCE: 32
taggactacg caggccatcg gaggatagta aat               33

<210> SEQ ID NO 33
<211> LENGTH: 33
<212> TYPE: DNA
<213> ORGANISM: Artificial Sequence
<220> FEATURE:
<223> OTHER INFORMATION: Synthetic (R85A forward primer)

<400> SEQUENCE: 33
gacagacgtc taccggcgtt tgtgtattgg aac                33

<210> SEQ ID NO 34
<211> LENGTH: 33
<212> TYPE: DNA
<213> ORGANISM: Artificial Sequence
<220> FEATURE:
<223> OTHER INFORMATION: Synthetic (R85A reverse primer)

<400> SEQUENCE: 34
gttccaatac acaaacgccg gtagacgtct gtc                33

<210> SEQ ID NO 35
<211> LENGTH: 34
<212> TYPE: DNA
<213> ORGANISM: Artificial Sequence
<220> FEATURE:
<223> OTHER INFORMATION: Synthetic (F156A forward primer)

<400> SEQUENCE: 35
cgtttagtcg caccagcggt ctccggtgtg tatg               34

<210> SEQ ID NO 36
<211> LENGTH: 34
<212> TYPE: DNA
<213> ORGANISM: Artificial Sequence
<220> FEATURE:
<223> OTHER INFORMATION: Synthetic (F156A reverse primer)

<400> SEQUENCE: 36
catacacacc ggagaccgct ggtgcgacta aacg               34

<210> SEQ ID NO 37
<211> LENGTH: 34
<212> TYPE: DNA
<213> ORGANISM: Artificial Sequence
<220> FEATURE:
<223> OTHER INFORMATION: Synthetic (V160C forward primer)

<400> SEQUENCE: 37
ccatttgtct ccggttgcta tgctggcgac gttg               34

<210> SEQ ID NO 38
<211> LENGTH: 34
<212> TYPE: DNA
<213> ORGANISM: Artificial Sequence
<220> FEATURE:
<223> OTHER INFORMATION: Synthetic (V160C reverse primer)

<400> SEQUENCE: 38
caacgtcgcc agcatagcaa ccggagacaa atgg               34

<210> SEQ ID NO 39
<211> LENGTH: 33
<212> TYPE: DNA
<213> ORGANISM: Artificial Sequence
<220> FEATURE:

<223> OTHER INFORMATION: Synthetic (F324V forward primer)

<400> SEQUENCE: 39
cgtccattgg aaggtgtggg tcatcttata ccc                33

<210> SEQ ID NO 40
<211> LENGTH: 33
<212> TYPE: DNA
<213> ORGANISM: Artificial Sequence
<220> FEATURE:
<223> OTHER INFORMATION: Synthetic (F324V reverse primer)

<400> SEQUENCE: 40
gggtataaga tgacccacac cttccaatgg acg                33

<210> SEQ ID NO 41
<211> LENGTH: 33
<212> TYPE: DNA
<213> ORGANISM: Artificial Sequence
<220> FEATURE:
<223> OTHER INFORMATION: Synthetic (L327T forward primer)

<400> SEQUENCE: 41
gaaggttttg gtcataccat acccaggaat cag                33

<210> SEQ ID NO 42
<211> LENGTH: 33
<212> TYPE: DNA
<213> ORGANISM: Artificial Sequence
<220> FEATURE:
<223> OTHER INFORMATION: Synthetic (L327T reverse primer)

<400> SEQUENCE: 42
ctgattcctg ggtatggtat gaccaaaacc ttc                33

<210> SEQ ID NO 43
<211> LENGTH: 33
<212> TYPE: DNA
<213> ORGANISM: Artificial Sequence
<220> FEATURE:
<223> OTHER INFORMATION: Synthetic (I340T forward primer)

<400> SEQUENCE: 43
aggactcttg gtacaacctg gtcctcctgt ctc                33

<210> SEQ ID NO 44
<211> LENGTH: 33
<212> TYPE: DNA
<213> ORGANISM: Artificial Sequence
<220> FEATURE:
<223> OTHER INFORMATION: Synthetic (I340T reverse primer)

<400> SEQUENCE: 44
gagacaggag gaccaggttg taccaagagt cct                33

<210> SEQ ID NO 45
<211> LENGTH: 35
<212> TYPE: DNA
<213> ORGANISM: Artificial Sequence
<220> FEATURE:
<223> OTHER INFORMATION: Synthetic (V160C+A162C forward primer)

<400> SEQUENCE: 45
tgtctccggt tgctattgtg gcgacgttga tcaac                35

<210> SEQ ID NO 46
<211> LENGTH: 35
<212> TYPE: DNA
<213> ORGANISM: Artificial Sequence
<220> FEATURE:
<223> OTHER INFORMATION: Synthetic (V160C+A162C reverse primer)

<400> SEQUENCE: 46
gttgatcaac gtcgccacaa tagcaaccgg agaca                              35

<210> SEQ ID NO 47
<211> LENGTH: 48
<212> TYPE: DNA
<213> ORGANISM: Artificial Sequence
<220> FEATURE:
<223> OTHER INFORMATION: Synthetic (V160C+A162L forward primer)

<400> SEQUENCE: 47
cgcaccattt gtctccggtt gctatcttgg cgacgttgat caactatc                48

<210> SEQ ID NO 48
<211> LENGTH: 48
<212> TYPE: DNA
<213> ORGANISM: Artificial Sequence
<220> FEATURE:
<223> OTHER INFORMATION: Synthetic (V160C+A162L reverse primer)

<400> SEQUENCE: 48
gatagttgat caacgtcgcc aagatagcaa ccggagacaa atggtgcg                48

<210> SEQ ID NO 49
<211> LENGTH: 33
<212> TYPE: DNA
<213> ORGANISM: Artificial Sequence
<220> FEATURE:
<223> OTHER INFORMATION: Synthetic (F359M forward primer)

<400> SEQUENCE: 49
caagttttta cttcaatgat cggtggagca aca                                33

<210> SEQ ID NO 50
<211> LENGTH: 33
<212> TYPE: DNA
<213> ORGANISM: Artificial Sequence
<220> FEATURE:
<223> OTHER INFORMATION: Synthetic (F359M reverse primer)

<400> SEQUENCE: 50
tgttgctcca ccgatcattg aagtaaaaac ttg                                33

<210> SEQ ID NO 51
<211> LENGTH: 32
<212> TYPE: DNA
<213> ORGANISM: Artificial Sequence
<220> FEATURE:
<223> OTHER INFORMATION: Synthetic (F359C forward primer)

<400> SEQUENCE: 51
ccaccgatgc atgaagtaaa aacttgccac cc                                 32

<210> SEQ ID NO 52
<211> LENGTH: 33
<212> TYPE: DNA
<213> ORGANISM: Artificial Sequence
<220> FEATURE:
<223> OTHER INFORMATION: Synthetic (F359C reverse primer)

<400> SEQUENCE: 52
tttacttcat gcatcggtgg agcaacagat ccg					33

<210> SEQ ID NO 53
<211> LENGTH: 33
<212> TYPE: DNA
<213> ORGANISM: Artificial Sequence
<220> FEATURE:
<223> OTHER INFORMATION: Synthetic (F359L forward primer)

<400> SEQUENCE: 53
tccaccgatc aatgaagtaa aaacttgcca ccc					33

<210> SEQ ID NO 54
<211> LENGTH: 33
<212> TYPE: DNA
<213> ORGANISM: Artificial Sequence
<220> FEATURE:
<223> OTHER INFORMATION: Synthetic (F359L reverse primer)

<400> SEQUENCE: 54
ttacttcatt gatcggtgga gcaacagatc cgg					33

<210> SEQ ID NO 55
<211> LENGTH: 33
<212> TYPE: DNA
<213> ORGANISM: Artificial Sequence
<220> FEATURE:
<223> OTHER INFORMATION: Synthetic (F359I forward primer)

<400> SEQUENCE: 55
caagttttta cttcaatcat cggtggagca aca					33

<210> SEQ ID NO 56
<211> LENGTH: 33
<212> TYPE: DNA
<213> ORGANISM: Artificial Sequence
<220> FEATURE:
<223> OTHER INFORMATION: Synthetic (F359I reverse primer)

<400> SEQUENCE: 56
tgttgctcca ccgatgattg aagtaaaaac ttg					33

<210> SEQ ID NO 57
<211> LENGTH: 33
<212> TYPE: DNA
<213> ORGANISM: Artificial Sequence
<220> FEATURE:
<223> OTHER INFORMATION: Synthetic (F359V forward primer)

<400> SEQUENCE: 57
caagttttta cttcagtcat cggtggagca aca					33

<210> SEQ ID NO 58
<211> LENGTH: 33
<212> TYPE: DNA
<213> ORGANISM: Artificial Sequence
<220> FEATURE:
<223> OTHER INFORMATION: Synthetic (F359V reverse primer)

<400> SEQUENCE: 58
tgttgctcca ccgatgactg aagtaaaaac ttg					33

<210> SEQ ID NO 59
<211> LENGTH: 34

```
<212> TYPE: DNA
<213> ORGANISM: Artificial Sequence
<220> FEATURE:
<223> OTHER INFORMATION: Synthetic (F359T forward primer)

<400> SEQUENCE: 59 caagtttttta cttcaaccat cggtggagca acag                              34

<210> SEQ ID NO 60
<211> LENGTH: 34
<212> TYPE: DNA
<213> ORGANISM: Artificial Sequence
<220> FEATURE:
<223> OTHER INFORMATION: Synthetic (F359T reverse primer)

<400> SEQUENCE: 60
ctgttgctcc accgatggtt gaagtaaaaa cttg                               34

<210> SEQ ID NO 61
<211> LENGTH: 30
<212> TYPE: DNA
<213> ORGANISM: Artificial Sequence
<220> FEATURE:
<223> OTHER INFORMATION: Synthetic (V304L forward primer)

<400> SEQUENCE: 61
tatccaacac tggcctgtgt agtactcgcc                                    30

<210> SEQ ID NO 62
<211> LENGTH: 31
<212> TYPE: DNA
<213> ORGANISM: Artificial Sequence
<220> FEATURE:
<223> OTHER INFORMATION: Synthetic (V304L reverse primer)

<400> SEQUENCE: 62
cacaggccag tgttggatac ggaatggccg c                                  31

<210> SEQ ID NO 63
<211> LENGTH: 33
<212> TYPE: DNA
<213> ORGANISM: Artificial Sequence
<220> FEATURE:
<223> OTHER INFORMATION: Synthetic (A166L forward primer)

<400> SEQUENCE: 63
gtctctggcg tgtatctggg agatccccag caa                                33

<210> SEQ ID NO 64
<211> LENGTH: 33
<212> TYPE: DNA
<213> ORGANISM: Artificial Sequence
<220> FEATURE:
<223> OTHER INFORMATION: Synthetic (A166L reverse primer)

<400> SEQUENCE: 64
ttgctgggga tctcccagat acacgccaga gac                                33

<210> SEQ ID NO 65
<211> LENGTH: 33
<212> TYPE: DNA
<213> ORGANISM: Artificial Sequence
<220> FEATURE:
<223> OTHER INFORMATION: Synthetic (A166C forward primer)

<400> SEQUENCE: 65
```
gtctctggcg tgtattgcgg agatccccag caa					33

<210> SEQ ID NO 66
<211> LENGTH: 33
<212> TYPE: DNA
<213> ORGANISM: Artificial Sequence
<220> FEATURE:
<223> OTHER INFORMATION: Synthetic (A166C reverse primer)

<400> SEQUENCE: 66
ttgctgggga tctccgcaat acacgccaga gac					33

<210> SEQ ID NO 67
<211> LENGTH: 33
<212> TYPE: DNA
<213> ORGANISM: Artificial Sequence
<220> FEATURE:
<223> OTHER INFORMATION: Synthetic (V304M forward primer)

<400> SEQUENCE: 67
attccgtatc caacaatggc ctgtgtagta ctc					33

<210> SEQ ID NO 68
<211> LENGTH: 33
<212> TYPE: DNA
<213> ORGANISM: Artificial Sequence
<220> FEATURE:
<223> OTHER INFORMATION: Synthetic (V304M reverse primer)

<400> SEQUENCE: 68
gagtactaca caggccattg ttggatacgg aat					33

<210> SEQ ID NO 69
<211> LENGTH: 34
<212> TYPE: DNA
<213> ORGANISM: Artificial Sequence
<220> FEATURE:
<223> OTHER INFORMATION: Synthetic (R88A forward primer)

<400> SEQUENCE: 69
gatcgacatc taccggcgta catttattgg cgag					34

<210> SEQ ID NO 70
<211> LENGTH: 34
<212> TYPE: DNA
<213> ORGANISM: Artificial Sequence
<220> FEATURE:
<223> OTHER INFORMATION: Synthetic (R88A reverse primer)

<400> SEQUENCE: 70
ctcgccaata aatgtacgcc ggtagatgtc gatc					34

<210> SEQ ID NO 71
<211> LENGTH: 34
<212> TYPE: DNA
<213> ORGANISM: Artificial Sequence
<220> FEATURE:
<223> OTHER INFORMATION: Synthetic (F160A forward primer)

<400> SEQUENCE: 71
cgtctggtgg cacctgcggt ctctggcgtg tatg					34

<210> SEQ ID NO 72
<211> LENGTH: 34
<212> TYPE: DNA
<213> ORGANISM: Artificial Sequence

```
<220> FEATURE:
<223> OTHER INFORMATION: Synthetic (F160A reverse primer)

<400> SEQUENCE: 72
catacacgcc agagaccgca ggtgccacca gacg                                    34

<210> SEQ ID NO 73
<211> LENGTH: 33
<212> TYPE: DNA
<213> ORGANISM: Artificial Sequence
<220> FEATURE:
<223> OTHER INFORMATION: Synthetic (V164C forward primer)

<400> SEQUENCE: 73
cctttcgtct ctggctgcta tgcgggagat ccc                                     33

<210> SEQ ID NO 74
<211> LENGTH: 33
<212> TYPE: DNA
<213> ORGANISM: Artificial Sequence
<220> FEATURE:
<223> OTHER INFORMATION: Synthetic (V164C reverse primer)

<400> SEQUENCE: 74
gggatctccc gcatagcagc cagagacgaa agg                                     33

<210> SEQ ID NO 75
<211> LENGTH: 34
<212> TYPE: DNA
<213> ORGANISM: Artificial Sequence
<220> FEATURE:
<223> OTHER INFORMATION: Synthetic (F323V forward primer)

<400> SEQUENCE: 75
gtcagtacga ccaggcgtgg gcgtccttat accc                                    34

<210> SEQ ID NO 76
<211> LENGTH: 34
<212> TYPE: DNA
<213> ORGANISM: Artificial Sequence
<220> FEATURE:
<223> OTHER INFORMATION: Synthetic (F323V reverse primer)

<400> SEQUENCE: 76
gggtataagg acgcccacgc ctggtcgtac tgac                                    34

<210> SEQ ID NO 77
<211> LENGTH: 42
<212> TYPE: DNA
<213> ORGANISM: Artificial Sequence
<220> FEATURE:
<223> OTHER INFORMATION: Synthetic (L326T forward primer)

<400> SEQUENCE: 77
ggctttggcg tcactatacc ccgtggccaa ggtatccgta ca                           42

<210> SEQ ID NO 78
<211> LENGTH: 42
<212> TYPE: DNA
<213> ORGANISM: Artificial Sequence
<220> FEATURE:
<223> OTHER INFORMATION: Synthetic (L326T reverse primer)

<400> SEQUENCE: 78
gccacggggt atagtgacgc caaagcctgg tcgtactgac ct                           42
```

<210> SEQ ID NO 79
<211> LENGTH: 33
<212> TYPE: DNA
<213> ORGANISM: Artificial Sequence
<220> FEATURE:
<223> OTHER INFORMATION: Synthetic (I339T forward primer)

<400> SEQUENCE: 79
cgtacactcg gcactacctg gtctagctgc tta          33

<210> SEQ ID NO 80
<211> LENGTH: 33
<212> TYPE: DNA
<213> ORGANISM: Artificial Sequence
<220> FEATURE:
<223> OTHER INFORMATION: Synthetic (I339T reverse primer)

<400> SEQUENCE: 80
taagcagcta gaccaggtag tgccgagtgt acg          33

<210> SEQ ID NO 81
<211> LENGTH: 39
<212> TYPE: DNA
<213> ORGANISM: Artificial Sequence
<220> FEATURE:
<223> OTHER INFORMATION: Synthetic (V164C+A166L forward primer)

<400> SEQUENCE: 81
cctttcgtct ctggctgcta tctgggagat ccccagcaa          39

<210> SEQ ID NO 82
<211> LENGTH: 39
<212> TYPE: DNA
<213> ORGANISM: Artificial Sequence
<220> FEATURE:
<223> OTHER INFORMATION: Synthetic (V164C+A166L reverse primer)

<400> SEQUENCE: 82
ttgctgggga tctcccagat agcagccaga gacgaaagg          39

<210> SEQ ID NO 83
<211> LENGTH: 33
<212> TYPE: DNA
<213> ORGANISM: Artificial Sequence
<220> FEATURE:
<223> OTHER INFORMATION: Synthetic (V164C+A166C forward primer)

<400> SEQUENCE: 83
ttcgtctctg gctgctattg cggagatccc cag          33

<210> SEQ ID NO 84
<211> LENGTH: 33
<212> TYPE: DNA
<213> ORGANISM: Artificial Sequence
<220> FEATURE:
<223> OTHER INFORMATION: Synthetic (V164C+A166C reverse primer)

<400> SEQUENCE: 84
ctggggatct ccgcaatagc agccagagac gaa          33

<210> SEQ ID NO 85
<211> LENGTH: 30
<212> TYPE: DNA
<213> ORGANISM: Artificial Sequence
<220> FEATURE:
<223> OTHER INFORMATION: Synthetic (CyPPO16_BamHIF primer)

<400> SEQUENCE: 85 cccc ggatcc atgctagact ccctgattgt                              30

<210> SEQ ID NO 86
<211> LENGTH: 34
<212> TYPE: DNA
<213> ORGANISM: Artificial Sequence
<220> FEATURE:
<223> OTHER INFORMATION: Synthetic (CyPPO16_SalIR primer)

<400> SEQUENCE: 86
ccccgtcgac tcactccctg cttctaattt tttg                          34

<210> SEQ ID NO 87
<211> LENGTH: 30
<212> TYPE: DNA
<213> ORGANISM: Artificial Sequence
<220> FEATURE:
<223> OTHER INFORMATION: Synthetic (CyPPO17_BamHIF primer)

<400> SEQUENCE: 87
ccccggatcc atggaggtcg atgttgcaat                               30

<210> SEQ ID NO 88
<211> LENGTH: 33
<212> TYPE: DNA
<213> ORGANISM: Artificial Sequence
<220> FEATURE:
<223> OTHER INFORMATION: Synthetic (CyPPO17_SalIR primer)

<400> SEQUENCE: 88
ccccgtcgac tcaggattgc cccccactca ggt                           33

<210> SEQ ID NO 89
<211> LENGTH: 1614
<212> TYPE: DNA
<213> ORGANISM: Artificial Sequence
<220> FEATURE:
<223> OTHER INFORMATION: Gene for AtPPO1 of Arabidopsis thaliana

<400> SEQUENCE: 89
atggagttat ctcttctccg tccgacgact caatcgcttc ttccgtcgtt ttcgaagccc    60
aatctccgat taaatgttta taagcctctt agactccgtt gttcagtggc cggtggacca   120
accgtcggat cttcaaaaat cgaaggcgga ggaggcacca ccatcacgac ggattgtgtg   180
attgtcggcg gaggtattag tggtctttgc atcgctcagg cgcttgctac taagcatcct   240
gatgctgctc cgaatttaat tgtgaccgag gctaaggatc gtgttggagg caacattatc   300
actcgtgaag agaatggttt tctctgggaa gaaggtccca atagttttca accgtctgat   360
cctatgctca ctatggtggt agatagtggt ttgaaggatg atttggtgtt gggagatcct   420
actgcgccaa ggtttgtgtt gtggaatggg aaattgaggc cggttccatc gaagctaaca   480
gacttaccgt tctttgattt gatgagtatt ggtgggaaga ttagagctgg ttttggtgca   540
cttggcattc gaccgtcacc tccaggtcgt gaagaatctg tggaggagtt tgtacggcgt   600
aacctcggtg atgaggtttt tgagcgcctg attgaaccgt tttgttcagg tgtttatgct   660
ggtgatcctt caaaactgag catgaaagca gcgtttggga aggtttggaa actagagcaa   720
aatggtggaa gcataatagg tggtacttta aggcaattca ggagaggaa aaacgctccc   780 aaggcagaac gagacccgcg cctgccaaaa ccacagggcc aaacagttgg ttctttcagg   840

-continued

```
aagggacttc gaatgttgcc agaagcaata tctgcaagat taggtagcaa agttaagttg       900
tcttggaagc tctcaggtat cactaagctg gagagcggag gatacaactt aacatatgag       960
actccagatg gtttagtttc cgtgcagagc aaaagtgttg taatgacggt gccatctcat      1020
gttgcaagtg gtctcttgcg ccctctttct gaatctgctg caaatgcact ctcaaaacta      1080
tattacccac cagttgcagc agtatctatc tcgtacccga aagaagcaat ccgaacagaa      1140
tgtttgatag atggtgaact aaagggtttt gggcaattgc atccacgcac gcaaggagtt      1200
gaaacattag gaactatcta cagctcctca ctctttccaa atcgcgcacc gcccggaaga      1260
attttgctgt tgaactacat tggcgggtct acaaacaccg gaattctgtc caagtctgaa      1320
ggtgagttag tggaagcagt tgacagagat ttgaggaaaa tgctaattaa gcctaattcg      1380
accgatccac ttaaattagg agttagggta tggcctcaag ccattcctca gtttctagtt      1440
ggtcactttg atatccttga cacggctaaa tcatctctaa cgtcttcggg ctacgaaggg      1500 ctattttgg gtggcaatta cgtcgctggt gtagccttag gccggtgtgt agaaggcgca       1560
tatgaaaccg cgattgaggt caacaacttc atgtcacggt acgcttacaa gtaa            1614
```

<210> SEQ ID NO 90
<211> LENGTH: 155
<212> TYPE: DNA
<213> ORGANISM: Artificial Sequence
<220> FEATURE:
<223> OTHER INFORMATION: Synthetic (Gene for Transit Peptide of AtPPO1)

<400> SEQUENCE: 90

```
atggagttat tcttctccgt ccgacgactc aatcgcttct tccgtcgttt tcgaagccca        60
atctccgatt aaatgtttat aagcctctta gactccgttg ttcagtggcc ggtggaccaa       120
ccgtcggatc ttcaaaaatc gaaggcggag gaggc                                  155
```

COMPOSITION AND METHOD FOR CONFERRING AND/OR ENHANCING HERBICIDE TOLERANCE USING VARIANTS OF PROTOPORPHYRINOGEN IX OXIDASE FROM CYANOBACTERIA

TECHNICAL FIELD

Provided are variants of a protoporphyrinogen IX oxidase derived from a prokaryote, and technology for conferring and/or enhancing herbicide tolerance of a plant and/or algae using the same.

BACKGROUND ART

A porphyrin biosynthetic pathway serves for the synthesis of chlorophyll and heme which play vital roles in plant metabolism, and it takes place in the chloroplast. In this pathway, protoporphyrinogen IX oxidase (hereinafter, referred to as PPO; EC:1.3.3.4) catalyzes the oxidation of protoporphyrinogen IX to protoporphyrin IX. After the oxidation of protoporphyrinogen IX to protoporphyrin IX, protoporphyrin IX binds with magnesium by Mg-chelatase to synthesize chlorophyll, or it binds with iron by Fe-chelatase to synthesize heme.

Therefore, when PPO activity is inhibited, synthesis of chlorophylls and heme is inhibited and the substrate protoporphyrinogen IX leaves the normal porphyrin biosynthetic pathway, resulting in the rapid export of protoporphyrinogen IX from the chloroplast to the cytoplasm, and cytoplasmic accumulation of protoporphyrin IX oxidized by nonspecific peroxidases and auto-oxidation. Accumulated protoporphyrin IX generates highly reactive singlet oxygen ($^1O_2$) in the presence of light and oxygen molecules which destroy cell membrane and rapidly leads to plant cell death. Based on this principle, herbicides inhibiting PPO activity have been developed. Until now, there have been 10 families of PPO-inhibiting herbicides, including pyrimidinediones, diphenyl-ethers, phenylpyrazoles, N-phenylphthalimides, thiadiazoles, oxadiazoles, triazinone, triazolinones, oxazolidinediones, and others herbicides, which are classified according to their chemical structures.

Further, in order to prevent effects of these herbicides on the growth of crops while using the herbicides, there is a need to provide herbicide tolerance for the crops.

Meanwhile, algae are photosynthetic organisms that can convert light energy into chemical energy which can be used to synthesize various useful compounds. For example, algae can fix carbon by photosynthesis and convert carbon dioxide into sugar, starch, lipids, fats, or other biomolecules, thereby removing greenhouse gases from the atmosphere. In addition, large-scale cultivation of algae can produce a variety of substances such as industrial enzymes, therapeutic compounds and proteins, nutrients, commercial materials and fuel materials.

However, in case of large-scale cultivation of algae in a bioreactor or in an open or enclosed pond, contamination may occur by undesired competent organisms, for example, undesired algae, fungi, rotifer, or zooplankton.

Thus, a technology is needed to harvest desired plants and/or algae on a large scale by treating herbicides at a concentration that would inhibit the growth of competent organisms without herbicide tolerance, after conferring herbicide tolerance to desired plants and/or algae.

REFERENCES (Patent document 1) U.S. Pat. No. 6,308,458 (2001 Oct. 30)
(Patent document 2) U.S. Pat. No. 6,808,904 (2004 Oct. 26)
(Patent document 3) U.S. Pat. No. 7,563,950 (2009 Jul. 21)
(Patent document 4) WO2011/085221 (2011 Jul. 14)
(Non-patent document 1) Li X, Volrath S L, Chilcott C E, Johnson M A, Ward E R, Law M D, Development of protoporphyrinogen IX oxidase as an efficient selection marker for *Agrobacterium tumefaciens*-mediated transformation of maize. Plant Physiol. 133:736-747, 2003

DISCLOSURE

Technical Problem

In this disclosure, it is found that hemY-type PPO genes derived from prokaryotes and mutants thereof show a broad herbicide tolerance to protoporphyrinogen IX oxidase (PPO)-inhibiting herbicides, thereby suggesting that the hemY-type PPO gene can conferr and/or enhance herbicide tolerance when it is introduced in a plant and/or algae.

One embodiment provides a polypeptide variant comprising:

an amino acid sequence having modification to SEQ ID NO: 1, wherein the modification comprises deletion and/or substitution with a different amino acid from an original amino acid at one or more amino acids selected from amino acids involved in the interaction of a polypeptide of SEQ ID NO: 1 with a PPO-inhibiting herbicide (e.g., at least one amino acid selected from amino acids positioned on binding sites of the polypeptide of SEQ ID NO: 1 interacting with PPO-inhibiting herbicide), or an amino acid sequence having at least 95%, at least 96%, at least 97%, at least 98%, or at least 99% identity with the amino acid sequence.

The at least one amino acid selected from the group consisting of amino acids of the polypeptide of SEQ ID NO: 1 involved in the interaction with a PPO-inhibiting herbicide, may be at least one amino acid selected from the group consisting of R85, F156, V160, A162, G163, V305, C307, F324, L327, L337, I340, and F360, of the amino acid sequence of SEQ ID NO: 1.

Another embodiment provides a polypeptide variant the variant comprising:

an amino acid sequence having modification to SEQ ID NO: 3, wherein the modification comprises deletion and/or substitution with a different amino acid from an original amino acid at one or more amino acids selected from amino acids involved in the interaction of a polypeptide of SEQ ID NO: 3 with a PPO-inhibiting herbicide (e.g., at least one amino acid selected from amino acids positioned on binding sites of the polypeptide of SEQ ID NO: 1 interacting with PPO-inhibiting herbicide), or an amino acid sequence having at least 95%, at least 96%, at least 97%, at least 98%, or at least 99% sequence identity with the amino acid sequence.

The at least one amino acid selected from the group consisting of amino acids of the polypeptide of SEQ ID NO: 3 affecting to the interaction with a PPO-inhibiting herbicide, SEQ ID NO: 3, may be at least one amino acid selected from the group consisting of R88, F160, V164, A166, G167, V304, C306, F323, L326, L336, I339, and F359, of the amino acid sequence of SEQ ID NO: 3.

Another embodiment provides a polynucleotide encoding the polypeptide variant.

Another embodiment provides a recombinant vector comprising the polynucleotide.

Another embodiment provides a recombinant cell comprising the recombinant vector.

Another embodiment provides a composition for conferring and/or enhancing herbicide tolerance of a plant and/or algae, comprising at least one selected from the group consisting of:

a polypeptide variant having modification to SEQ ID NO: 1 or SEQ ID NO: 3, or a polypeptide comprising an amino acid sequence having 95% or higher, 96% or higher, 97% or higher, 98% or higher, or 99% or higher sequence identity with the polypeptide variant;

a polynucleotide encoding the polypeptide variant or the polypeptide comprising an amino acid sequence having 95% or higher, 96% or higher, 97% or higher, 98% or higher, or 99% or higher sequence identity with the polypeptide variant;

a recombinant vector comprising the polynucleotide; and a recombinant cell comprising the recombinant vector.

In a concrete embodiment, the polynucleotide encoding the polypeptide of SEQ ID NO: 1 may comprise the nucleic acid sequence of SEQ ID NO: 2, the polynucleotide encoding the polypeptide of SEQ ID NO: 3 may comprise the nucleic acid sequence of SEQ ID NO: 4; but the polynucleotides may not be limited thereto.

The herbicide may be an herbicide inhibiting a protoporphyrinogen IX oxidase activity.

For example, the herbicide may be at least one selected from the group consisting of pyrimidinediones, diphenylethers, phenylpyrazoles, N-phenylphthalimides, phenylesters, thiadiazoles, oxadiazoles, triazinone, triazolinones, oxazolidinediones, and other herbicides, but not be limited thereto.

In a specific embodiment, the herbicide may be at least one selected from the group consisting of tiafenacil, butafenacil, saflufenacil, benzfendizone, fomesafen, oxyfluorfen, aclonifen, acifluorfen, bifenox, ethoxyfen, lactofen, chlomethoxyfen, chlornitrofen, fluoroglycofen-ethyl, halosafen, pyraflufen-ethyl, fluazolate, flumioxazin, cinidon-ethyl, flumiclorac-pentyl, fluthiacet, thidiazimin, oxadiargyl, oxadiazon, carfentrazone, sulfentrazone, trifludimoxazin, azafenidin, pentoxazone, pyraclonil, flufenpyrethyl, profluazol, phenopylate (2,4-dichlorophenyl 1-pyrrolidinecarboxylate), carbamate analogues of phenopylate (for example, O-phenylpyrrolidino- and piperidinocarbamate analoges (refer to "Ujjana B. Nandihalli, Mary V. Duke, Stephen O. Duke, Relationships between molecular properties and biological activities of 0-phenyl pyrrolidino- and piperidinocarbamate herbicides, J. Agric. Food Chem., 40(10) 1993-2000, 1992")), agriculturally acceptable salts thereof, and combinations thereof, but not be limited thereto.

The plant may refer to a multicellular eukaryotic organism having photosynthetic capability, which may be a monocotyledonous plant or a dicotyledonous plant, or may be an herbaceous plant or a woody plant. The algae may refer to unicellular organism having photosynthetic capability, which may be prokaryotic algae or eukaryotic algae.

In an embodiment, the plant or algae may be genetically manipulated in order to further comprise a second herbicide tolerance polypeptide or a gene encoding the second herbicide tolerance polypeptide, whereby herbicide tolerance to the second herbicide can be conferred and/or enhanced. The plant or algae, which is genetically manipulated in order to comprise the second herbicide tolerance polypeptide or a gene encoding the second herbicide tolerance polypeptide, may be prepared using the second herbicide tolerance polypeptide or a gene encoding the second herbicide tolerance polypeptide in addition to the above mentioned composition for conferring and/or enhancing herbicide tolerance. Thus, a composition for conferring and/or enhancing tolerance to the herbicide may further comprise the second herbicide tolerance polypeptide or a gene encoding the second herbicide tolerance polypeptide.

Examples of the second herbicide may comprise cell division-inhibiting herbicides, photosynthesis-inhibiting herbicides, amino acid synthesis-inhibiting herbicides, plastid-inhibiting herbicides, cell membrane-inhibiting herbicides, and the like, but not be limited thereto.

In a specific embodiment, the second herbicide may be exemplified by glyphosate, glufosinate, dicamba, 2,4-D (2,4-Dichlorophenoxyacetic acid), isoxaflutole, ALS (acetolactate synthase)-inhibiting herbicide, photosystem II-inhibiting herbicide, or phenylurea-based herbicide, bromoxynil-based herbicide, or combinations thereof, but not be limited thereto.

For example, the second herbicide-tolerant polypeptide may be exemplified by at least one selected from the group consisting of glyphosate herbicide-tolerant EPSPS (glyphosate resistant 5-enolpyruvylshikimate-3-phosphate synthase), GOX (glyphosate oxidase), GAT (glyphosate-N-acetyltransferase) or glyphosate decarboxylase); glufosinate herbicide-tolerant PAT (phosphinothricin-N-acetyltransferase); dicamba herbicide-tolerant DMO (dicamba monooxygenase); 2,4-D herbicide-tolerant 2,4-D monooxygenase or AAD (aryloxyalkanoate dioxygenase); ALS-inhibiting sulfonylurea-based herbicide-tolerant ALS (acetolactate synthase), AHAS (acetohydroxyacid synthase), or AtAHASL (*Arabidopsis thaliana* acetohydroxyacid synthase large subunit); photosystem II-inhibiting herbicide-tolerant photosystem II protein Dl; phenylurea-based herbicide-tolerant cytochrome P450; plastid-inhibiting herbicide-tolerant HPPD (hydroxyphenylpyruvate dioxygenase); bromoxynil herbicide-tolerant nitrilase; and combinations thereof, but not limited thereto.

In addition, the gene encoding the second herbicide-tolerant polypeptide may be exemplified by at least one selected from the group consisting of glyphosate herbicide-tolerant cp4 epsps, mepsps, 2mepsps, goxv247, gat4601 or gat4621 gene; glufosinate herbicide-tolerant bar, pat or pat (SYN) gene; dicamba herbicide-tolerant dmo gene; 2,4-D herbicide-tolerant AAD-1, AAD-12 gene; ALS-inhibiting sulfonylurea-based herbicide-tolerant ALS, GM-HRA, S4-HRA, ZM-HRA, Csr1, Csr1-1, Csr1-2, SurA or SurB; photosystem II-inhibiting herbicide-tolerant psbA gene; phenylurea herbicide-tolerant CYP76B1 gene; isoxaflutole herbicide-tolerant HPPDPF W336 gene and bromoxynil herbicide-tolerant bxn gene; and combinations thereof, but not limited thereto.

Another embodiment provides a transformant of a plant and/or algae having herbicide tolerance, which is transformed with the polynucleotide, or a clone or progeny thereof.

Another embodiment provides a method of preparing a transgenic plant or a transgenic alga having herbicide tolerance or enhanced herbicide tolerance, comprising a step of transforming a plant and/or algae with the polynucleotide.

Another embodiment provides a method of conferring or enhancing herbicide tolerance of a plant and/or algae, comprising a step of transforming a plant and/or algae with the polynucleotide.

The transformation may be performed to an alga, and/or a cell, protoplast, callus, hypocotyl, seed, cotyledon, shoot, or whole body of a plant.

The transformant may be an alga, and/or a cell, protoplast, callus, hypocotyl, seed, cotyledon, shoot, or whole body of a plant.

Another embodiment provides a method of controlling weeds in a cropland comprising:

providing a plant to the cropland, wherein the plant comprises at least one selected from the group consisting of the polypeptide, the variant of the polypeptide, a polynucleotide encoding the polypeptide, a polynucleotide encoding the variant, a recombinant vector comprising the polynucleotide, and a recombinant cell comprising the recombinant vector; and applying an effective amount of a protoporphyrinogen IX oxidase-inhibiting herbicide to the cropland.

In a specific embodiment, the step of applying an effective amount of a protoporphyrinogen IX oxidase-inhibiting herbicide to the cropland may be performed by applying an effective amount of at least two protoporphyrinogen IX oxidase-inhibiting herbicides sequentially or simultaneously.

In another embodiment, the plant may be genetically manipulated in order to further comprise a second herbicide-tolerant polypeptide or a gene encoding the second herbicide-tolerant polypeptide, and an effective amount of the protoporphyrinogen IX oxidase-inhibiting herbicide and the second herbicide may be applied sequentially or simultaneously.

Another embodiment provides a method of removing an undesired organism from a culture medium, comprising providing an alga to a culture medium, wherein the algae comprises at least one selected from the group consisting of the polypeptide, the variant of the polypeptide, a polynucleotide encoding the polypeptide, a polynucleotide encoding the variant, a recombinant vector comprising the polynucleotide, and a recombinant cell comprising the recombinant vector; and applying an effective amount of a protoporphyrinogen IX oxidase-inhibiting herbicide to the culture medium.

Technical Solution

Provided is a technology of conferring and/or enhancing herbicide tolerance of plants or algae.

As used herein, 'conferring and/or enhancing herbicide tolerance of plants or algae' or 'enhancing herbicide tolerance of plants or algae' may be interpreted as conferring herbicide tolerance to a plant or algae which do not have herbicide tolerance, and/or more strengthening herbicide tolerance of a plant or algae which have herbicide tolerance.

As used herein, 'consisting of a sequence' or 'comprising a sequence' may be used in order to cover both cases of comprising described sequence, and/or necessarily comprising the sequence, but it is not intended to exclude comprising further sequence other than the described sequence.

An embodiment provides a polypeptide variant which is at least one selected from the group consisting of:

a polypeptide variant comprising an amino acid sequence having modification to SEQ ID NO: 1, wherein the modification comprises deletion and/or substitution with a different amino acid from an original amino acid at one or more amino acids selected from amino acids involved in the interaction of a polypeptide of SEQ ID NO: 1 with a PPO-inhibiting herbicide (e.g., at least one amino acid selected from amino acids positioned on binding sites of the polypeptide of SEQ ID NO: 1 interacting with PPO-inhibiting herbicide), or an amino acid sequence having 95% or higher, 96% or higher, 97% or higher, 98% or higher, or 99% or higher sequence identity with the amino acid sequence; and a polypeptide variant comprising an amino acid sequence having modification to SEQ ID NO: 3, wherein the modification comprises deletion and/or substitution with a different amino acid from an original amino acid at one or more amino acids selected from amino acids involved in the interaction of a polypeptide of SEQ ID NO: 3 with a PPO-inhibiting herbicide (e.g., at least one amino acid selected from amino acids positioned on binding sites of the polypeptide of SEQ ID NO: 3 interacting with PPO-inhibiting herbicide), or an amino acid sequence having 95% or higher, 96% or higher, 97% or higher, 98% or higher, or 99% or higher sequence identity with the amino acid sequence.

In other embodiment, provided is a polynucleotide encoding a polypeptide variant from the polypeptide of SEQ ID NO: 1 or 3, a recombinant vector comprising the polynucleotide, and a recombinant cell comprising the recombinant vector. The polynucleotide may be designed in order to comprise a codon which is optimized to a cell to be transformed. The optimized codon may be easily known to a person skilled in the art (for example, refer to "http://www.genscript.com/codon-opt.html", "http://sg.idtdna.com/CodonOpt", etc.).

Another embodiment provides a composition for conferring and/or enhancing herbicide tolerance of a plant and/or algae, comprising at least one selected from the group consisting of:

a polypeptide variant having modification to SEQ ID NO: 1 or SEQ ID NO: 3, or a polypeptide comprising an amino acid sequence having 95% or higher, 96% or higher, 97% or higher, 98% or higher, or 99% or higher sequence identity with the polypeptide variant;

a polynucleotide encoding the polypeptide variant or the polypeptide comprising an amino acid sequence having 95% or higher, 96% or higher, 97% or higher, 98% or higher, or 99% or higher sequence identity with the polypeptide variant;

a recombinant vector comprising the polynucleotide; and a recombinant cell comprising the recombinant vector.

In a concrete embodiment, the polynucleotide encoding the polypeptide of SEQ ID NO: 1 may comprise the nucleic acid sequence of SEQ ID NO: 2, the polynucleotide encoding the polypeptide of SEQ ID NO: 3 may comprise the nucleic acid sequence of SEQ ID NO: 4; but the polynucleotides may not be limited thereto.

In other embodiment, provided is a transformant of a plant and/or algae having herbicide tolerance, which is transformed with the polypeptide or a polynucleotide encoding the polypeptide. The polynucleotide may be designed in order to comprise a codon which is optimized to a cell to be transformed. The optimized codon may be easily known to a person skilled in the art (for example, refer to "http://www.genscript.com/codon-opt.html", "http://sg.idtdna.com/CodonOpt", etc.)

Another embodiment provides a method of preparing a transgenic plant or a transgenic algae having herbicide tolerance or enhanced herbicide tolerance, comprising a step of transforming a cell, protoplast, callus, hypocotyl, seed, cotyledon, shoot, or whole body of a plant or algae, with the polynucleotide.

Another embodiment provides a method of conferring or enhancing herbicide tolerance of a plant and/or algae, comprising a step of transforming a cell, protoplast, callus, hypocotyl, seed, cotyledon, shoot, or whole body of a plant or algae, with the polynucleotide.

The polypeptides of SEQ ID NO: 1 and 3 described herein are PPO proteins derived from a prokaryote (for example, cyanobacteria), and are herbicide-tolerant PPO proteins having tolerance to a PPO-inhibiting herbicide(s). Specifically, a PPO protein which is derived from *Spirulina subsalsa* is provided, and it is designated as CyPPO16, and its amino acid sequence is represented by SEQ ID NO: 1, and a nucleotide sequence of a gene encoding the same is represented by SEQ ID NO: 2. In addition, a PPO derived from *Thermosynechococcus* sp. NK55a strain is provided, and it is designated as CyPPO17, and its amino acid sequence is represented by SEQ ID NO: 3, and a nucleotide sequence of a gene encoding the same is represented by SEQ ID NO: 4.

Herein, the polypeptide and variants of polypeptide may be expressed respectively as herbicide-tolerant PPO protein or herbicide-tolerant PPO protein variant having tolerance to a PPO-inhibiting herbicide(s). In addition, as used herein, the wording "a herbicide-tolerant PPO or its variant" may be used in order to refer to the above herbicide-tolerant PPO protein or herbicide-tolerant PPO protein variant, a herbicide-tolerant PPO protein-encoding gene or a herbicide-tolerant PPO protein variant-encoding gene, or all of them.

Cyanobacteria-derived PPO proteins are possessing excellent enzymatic activities compared to those of plant PPO proteins, and capable of conferring tolerance to PPO-inhibiting herbicides. In addition, when the cyanobacteria-derived PPO proteins are modified by amino acid mutation (variation) within a range capable of maintaining their overall enzymatic activities, their tolerance to PPO-inhibiting herbicides can be more enhanced compared to those of wild type PPO proteins. Such amino acid mutation may comprise substitution, deletion, addition and/or introduction of one or more amino acids selected from amino acid residues of interaction sites of the PPO proteins where the PPO proteins interact with herbicides.

The PPO protein variant will be described in more detail as follows.

One embodiment provides a polypeptide variant, which is a variant of a polypeptide of SEQ ID NO: 1 (CyPPO16), the variant comprising:

an amino acid sequence having modification to SEQ ID NO: 1 (CyPPO16), wherein the modification comprises deletion and/or substitution with a different amino acid from an original amino acid at one or more amino acids selected from amino acids involved in the interaction of a polypeptide of SEQ ID NO: 1 with a PPO-inhibiting herbicide (e.g., at least one amino acid selected from amino acids positioned on binding sites of the polypeptide of SEQ ID NO: 1 (CyPPO16) interacting with PPO-inhibiting herbicide), or an amino acid sequence having at least 95%, at least 96%, at least 97%, at least 98%, or at least 99% identity with the amino acid sequence.

The amino acid residue of SEQ ID NO: 1 to be deleted or substituted with other amino acid that is different from the original amino acid (e.g., at least one residue selected from the group consisting of amino acids positioned on binding sites to PPO-inhibiting herbicides of polypeptide of SEQ ID NO: 1) may be at least one selected from the group consisting of R85 (referring to "R(Arg) at the 85$^{th}$ position; the expression of the following amino acid residues is interpreted in this manner), F156, V160, A162, G163, V305, C307, F324, L327, L337, I340, and F360 of the amino acid sequence of SEQ ID NO: 1.

In one specific embodiment, the variant of polypeptide may comprise:

an amino acid sequence having modification to SEQ ID NO: 1, wherein one or more amino acid residues selected from the group consisting of R85, F156, V160, A162, G163, V305, C307, F324, L327, L337, I340, and F360 of the amino acid sequence of SEQ ID NO: 1 are respectively and independently deleted or substituted with an amino acid selected from the group consisting of M(Met), V(Val), I(Ile), T(Thr), L(Leu), C(Cys), A(Ala), S(Ser), F(Phe), P(Pro), W(Trp), N(Asn), Q(Gln), G(Gly), Y(Tyr), D(Asp), E(Glu), R(Arg), H(His), K(Lys), and the like, which is different from the amino acid at the corresponding position in the wild type (for example, respectively and independently substituted with an amino acid selected from the group consisting of M(Met), V(Val), I(Ile), T(Thr), L(Leu), C(Cys), S(Ser), A(Ala), and the like, which is different from the amino acid at the corresponding position in the wild type), or an amino acid sequence having at least 95%, at least 96%, at least 97%, at least 98%, or at least 99% sequence identity with the amino acid sequence.

For example, the variant of polypeptide may comprise:

an amino acid sequence having modification to SEQ ID NO: 1, wherein the modification comprises at least one amino acid mutation selected from the group consisting of F360M (referring to a mutant or mutation wherein "the amino acid residue at the 360$^{th}$ position is substituted from F(Phe) to M(Met)"; the expression of the following amino acid mutations is interpreted in this manner), F360L, F360I, F360C, F360V, F360T, V305I, V305L, A162L, A162C, A162I, V305M, R85A, F156A, V160C, V160S, F324V, L327T, and I340T, in the amino acid sequence of SEQ ID NO: 1; or an amino acid sequence having at least 95%, at least 96%, at least 97%, at least 98%, or at least 99% sequence identity with the amino acid sequence.

More specifically, the variant of polypeptide may comprise:

an amino acid sequence having modification to SEQ ID NO: 1, wherein the modification comprises at least one amino acid mutation selected from the group consisting of amino acid mutations of F360M, F360L, F360I, F360C, F360V, F360T, V305I, V305L, A162L, A162C, A162I, V305M, R85A, F156A, V160C, V160S, F324V, L327T, I340T, R85A+F360M (referring to a mutant or mutation comprising all of substitution of the 85$^{th}$ residue from R to A and substitution of the 360$^{th}$ residue from F to M; the expression of the following two or more amino acid mutations is interpreted in this manner), R85A+F360V, R85A+F360I, F156A+F360M, V160C+F360M, V160C+F360I, V160C+F360V, A162C+F360M, A162C+F360I, A162C+F360V, A162L+F360M, A162L+F360I, A162L+F360V, V305M+F360M, V305M+F360I, V305M+F360V, F324V+F360M, L327T+F360M, L327T+F360I, L327T+F360V, I340T+F360M, R85A+V160C+F360I, R85A+A162L+F360M, R85A+V305M+F360I, R85A+L327T+F360M, V160C+A162L+F360I, V160C+V305M+F360M, V160C+L327T+F360I, A162L+V305M+F360M, A162C+L327T+F360M, V305M+L327T+F360M, A162C+V305M+F360M, A162I+V305M+F360M, V160C+A162C+F360M, V160C+A162L+F360M, R85A+V160C+A162L+F360I, R85A+V160C+V305M+F360M, R85A+V160C+L327T+F360I, R85A+A162C+L327T+F360M, R85A+A162L+V305M+F360M, R85A+V305M+L327T+F360M, V160C+A162L+V305M+F360I, V160C+A162C+L327T+F360M, A162C+V305M+L327T+F360M, R85A+V160C+A162C+L327T+F360M, R85A+V160C+A162L+V305M+F360M, V160C+A162C+V305M+L327T+F360M, or R85A+V160C+A162C+V305M+L327T+F360M, in the amino acid sequence of SEQ ID NO: 1, or an amino acid sequence having at least 95%, at least 96%, at least 97%, at least 98%, or at least 99% sequence identity with the amino acid sequence.

Another embodiment provides a polypeptide variant, which is a variant of a polypeptide of SEQ ID NO: 3 (CyPPO17), the variant comprising:

an amino acid sequence having modification to SEQ ID NO: 3 (CyPPO17), wherein the modification comprises deletion and/or substitution with a different amino acid from an original amino acid at one or more amino acids selected from amino acids involved in the interaction of a polypeptide of SEQ ID NO: 3 with a PPO-inhibiting herbicide (e.g., at least one amino acid selected from amino acids positioned on binding sites of the polypeptide of SEQ ID NO: 3 (CyPPO17) interacting with PPO-inhibiting herbicide), or an amino acid sequence having at least 95%, at least 96%, at least 97%, at least 98%, or at least 99% identity with the amino acid sequence.

The amino acid residue of polypeptide of SEQ ID NO: 3 to be deleted or substituted with other amino acid which is different from the original amino acid (e.g., at least one residue selected from the group consisting of amino acids positioned on binding sites to PPO-inhibiting herbicides of polypeptide of SEQ ID NO: 3), may be at least one selected from the group consisting of R88, F160, V164, A166, G167, V304, C306, F323, L326, L336, I339, and F359 of the amino acid sequence of SEQ ID NO: 3.

In one specific embodiment, the variant of polypeptide may comprise:

an amino acid sequence having modification to SEQ ID NO: 3, wherein one or more amino acid residues selected from the group consisting of R88, F160, V164, A166, G167, V304, C306, F323, L326, L336, I339 and F359 of the amino acid sequence of SEQ ID NO: 3 are respectively and independently deleted or substituted with an amino acid selected from the group consisting of M(Met), V(Val), I(Ile), T(Thr), L(Leu), C(Cys), A(Ala), S(Ser), F(Phe), P(Pro), W(Trp), N(Asn), Q(Gln), G(Gly), Y(Tyr), D(Asp), E(Glu), R(Arg), H(His), K(Lys), and the like, which is different from the amino acid at the corresponding position in the wild type (for example, one or more amino acid residues selected from the group consisting of R88, F160, V164, A166, G167, V304, C306, F323, L326, L336, I339 and F359 of the amino acid sequence of SEQ ID NO: 3 are respectively and independently substituted with an amino acid selected from the group consisting of M(Met), V(Val), I(Ile), T(Thr), L(Leu), C(Cys), A(Ala), and the like, which is different from the amino acid at the corresponding position in the wild type), or an amino acid sequence having at least 95%, at least 96%, at least 97%, at least 98%, or at least 99% sequence identity with the amino acid sequence.

For example, the variant of polypeptide may comprise:

an amino acid sequence having modification to SEQ ID NO: 3, wherein the modification comprises at least one amino acid mutation selected from the group consisting of F359M, F359C, F359L, F359I, F359V, F359T, V304I, V304L, A166L, A166C, A166I, V304M, R88A, F160A, V164C, V164S, F323V, L326T, and I339T in the amino acid sequence of SEQ ID NO: 3; or an amino acid sequence having at least 95%, at least 96%, at least 97%, at least 98%, or at least 99% sequence identity with the amino acid sequence.

More specifically, the variant of polypeptide may comprise:

an amino acid sequence having modification to SEQ ID NO: 3, wherein the modification comprises at least one amino acid mutation selected from the group consisting of amino acid mutations of F359M, F359C, F359L, F359I, F359V, F359T, V304I, V304L, A166C, A166I, V304M, R88A, F160A, V164C, V164S, F323V, L326T, I339T, R88A+F359I, R88A+F359V, R88A+F359M, V164C+F359I, V164C+F359V, V164C+F359M, A166L+ F359I, A166L+F359V, A166L+F359M, A166C+F359I, A166C+F359V, A166C+F359M, F160A+F359M, V304M+ F359I, V304M+F359V, V304M+F359M, F323V+F359M, L326T+F359I, L326T+F359V, L326T+F359M, I339T+ F359M, R88A+V164C+F359I, R88A+A166L+F359M, R88A+V304M+F359I, R88A+L326T+F359M, V164C+ A166L+F359I, V164C+V304M+F359M, V164C+L326T+ F359I, A166L+V304M+F359M, A166L+L326T+F359I, V304M+L326T+F359M, A166C+V304M+F359M, A166I+ V304M+F359M, V164C+A166C+F359M, V164C+ A166L+F359M, R88A+V164C+A166L+F359I, R88A+ V164C+V304M+F359I, R88A+V164C+L326T+F359M, R88A+A166L+V304M+F359I, R88A+A166L+L326T+ F359M, R88A+V304M+L326T+F359M, V164C+A166L+ V304M+F359I, V164C+A166L+L326T+F359M, A166L+ V304M+L326T+F359I, R88A+V164C+A166L+V304M+ F359I, R88A+V164C+A166L+L326T+F359M, V164C+ A166L+V304M+L326T+F359M, or R88A+V164C+ A166C+V304M+L326T+F359M, in the amino acid sequence of SEQ ID NO: 3, or an amino acid sequence having at least 95%, at least 96%, at least 97%, at least 98%, or at least 99% sequence identity with the amino acid sequence.

The polypeptide variant comprising an amino acid sequence having sequence identity (for example, 95% or higher, 98% or higher, or 99% or higher sequence identity) described herein may maintain enzyme activity equivalent to that of a polypeptide having an amino acid sequence which is a standard of identification of sequence identity (for example, the PPO protein having amino acid mutation described above), for example, 5% or higher, 10% or higher, 20% or higher, 30% or higher, 40% or higher, 50% or higher, 60% or higher, 70% or higher, 80% or higher, 90% or higher, or 95% or higher enzyme activity to a polypeptide having an amino acid sequence which is a standard in plants (in a whole plant, in a plant cell or cell culture, in a plant tissue, etc.), in algae, and/or in vitro, and having function to confer herbicide tolerance. The sequence identity description is used in order to clarify that the herbicide-tolerance PPO protein variant or polypeptide variant described herein may comprise any sequence mutation within the range capable of satisfying the above condition (maintaining enzymatic activity and possessing a function to confer herbicide tolerance).

The amino acids used in the description are summarized as follows:

| Amino acid | 3-letter code | 1-letter code |
|---|---|---|
| Alanine | Ala | A |
| Isoleucine | Ile | I |
| Leucine | Leu | L |
| Methionine | Met | M |
| Phenylalanine | Phe | F |
| Proline | Pro | P |
| Tryptophan | Trp | W |
| Valine | Val | V |
| Aspargine | Asn | N |
| Cysteine | Cys | C |
| Glutamine | Gln | Q |
| Glycine | Gly | G |
| Serine | Ser | S |
| Threonine | Thr | T |
| Tyrosine | Tyr | Y |
| Aspartic acid | Asp | D |
| Glutamic acid | Glu | E |
| Arginine | Arg | R |
| Histidine | His | H |
| Lysine | Lys | K |

The polypeptide variant (herbicide-tolerant PPO protein variant) may maintain its enzymatic activities as a PPO protein, and exhibit increased herbicide tolerance compared to the wild type.

In addition, the polypeptide variant (herbicide-tolerant PPO protein variant) may comprise further mutation exhibiting biologically equal activity to a polypeptide consisting of SEQ ID NO: 1, SEQ ID NO: 3, or an amino acid sequence having amino acid mutation(s) described above. For example, the additional mutation may be amino acid substitution which does not entirely alter molecular activity, and such amino acid substitution may be properly selected by a person skilled in the relevant art. In one example, the additional substitution may be substitution between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, or Asp/Gly, but not be limited thereto. In some cases, the herbicide-tolerant PPO protein variant may be subjected to at least one modification selected from the group consisting of phosphorylation, sulfation, acylation, glycosylation, methylation, farnesylation, and the like. In addition, the herbicide-tolerant PPO protein variant may be one having increased structural stability to heat, pH, etc. of the protein, or increased protein activity by amino acid variation (mutation) and/or modification.

The term "sequence identity" refers to the degree of similarity to the wild type or reference amino acid sequence or nucleotide sequence, and any protein may be included in the scope of the present invention, as long as it includes amino acid residues having 60% or higher, 65% or higher, 70% or higher, 75% or higher, 80% or higher, 85% or higher, 90% or higher, 95% or higher, 98% or higher, or 99% or higher identity to the amino acid sequence of the herbicide-tolerant PPO protein variant as described above, and retains biological activities equivalent to the herbicide-tolerant PPO protein variant. Such protein homologues may comprise an active site equivalent to that of a targeted protein (the herbicide-tolerant PPO protein variant as described above).

The herbicide-tolerant PPO protein or its variant may be obtained by extracting and/or purifying from nature by methods well known in the relevant art. Alternatively, it may be obtained as a recombinant protein using a gene recombination technology. In case of using a gene recombination technology, it may be obtained by a process of introducing a nucleic acid encoding the herbicide-tolerant PPO protein or its variant into an appropriate expression vector, and introducing the expression vector into a host cell in order to express the herbicide-tolerant PPO protein or its variant, and then collecting the expressed herbicide-tolerant PPO protein or its variant from the host cell. After the protein is expressed in a selected host cell, the protein can be separated and/or purified by general biochemical separation techniques, for example, treatment with a protein precipitating agent (salting out), centrifugation, ultrasonic disruption, ultrafiltration, dialysis, chromatography such as molecular sieve chromatography (gel filtration), adsorption chromatography, ion exchange chromatography, affinity chromatography and the like, and in order to separate the protein with a high purity, these methods may be used in combination.

The herbicide-tolerant PPO nucleic acid molecule (polynucleotide encoding the PPO protein or its variant) may be isolated or prepared using standard molecular biological techniques, for example, a chemical synthesis or recombination method, or as the herbicide-tolerant PPO nucleic acid molecule, commercially available one can be used.

In this disclosure, the PPO proteins/nucleic acids or variants thereof were found to exhibit broad herbicide tolerance against representative 10 families of PPO inhibiting herbicides classified according to their chemical structures in a herbicide tolerance test system using PPO-deficient $E.\ coli$ BT3($\Delta$PPO). It was also found that the proteins may be expressed in the chloroplast of a plant by using a transit peptide (TP). Further, it was found that the PPO proteins/nucleic acids or variants thereof may be also expressed in a monocotyledon, such as $Oryza\ sativa$, or a dicotyledon, such as, $Arabidopsis\ thaliana$ ecotype Columbia-0 ($A.\ thaliana$), by a plant expression vector. Even when the transformed plants are treated with PPO-inhibiting herbicides, germination and growth of the plants are observed. Furthermore, it was confirmed, by an inheritance study, that the above herbicide-tolerant traits can be successfully inherited to the next generation.

Therefore, the PPO protein and its variants provided herein may be introduced into a plant or algae, thereby conferring herbicide tolerance to the plant or algae, and/or enhancing herbicide tolerance of the plant or algae.

One embodiment provides a composition for conferring and/or enhancing herbicide tolerance of plants and/or algae, comprising at least one selected from the group consisting of:

(1) a polypeptide variant as described above or comprising an amino acid sequence having at least 95%, at least 96%, at least 97%, at least 98%, or at least 99% sequence identity thereto;

(2) a polynucleotide encoding the polypeptide variant;

(3) a recombinant vector comprising the polynucleotide; and (4) a recombinant cell comprising the recombinant vector.

The herbicide herein refers to an active ingredient that kills, controls, or otherwise adversely modifies the growth of plants or algae. In addition, the herbicide tolerance means that even after treatment of a herbicide which normally kills a normal or wild-type plant or normally inhibits growth thereof, inhibition of the plant growth is weakened or eliminated, compared to that of the normal or wild-type plant, and therefore, the plant continues to grow. The herbicide includes a herbicide inhibiting protoporphyrinogen IX oxidase (PPO) of a plant or an alga. Such PPO-inhibiting herbicide may be classified into pyrimidinediones, diphenylethers, phenylpyrazoles, N-phenylphthalimides, phenylesters, thiadiazoles, oxadiazoles, triazinone, triazolinones, oxazolidinediones, and other herbicides, according to their chemical structures.

As a specific embodiment, the pyrimidinedione-based herbicide may include butafenacil, saflufenacil, benzfendizone, and tiafenacil, but not be limited thereto.

The diphenyl-ether-based herbicide may include fomesafen, oxyfluorfen, aclonifen, acifluorfen, bifenox, ethoxyfen, lactofen, chlomethoxyfen, chlornitrofen, fluoroglycofen-ethyl, and halosafen, but not be limited thereto.

The phenylpyrazole-based herbicide may include pyraflufen-ethyl and fluazolate, but not be limited thereto.

The phenylphthalimide-based herbicide may include flumioxazin, cinidon-ethyl, and flumiclorac-pentyl, but not be limited thereto.

The phenylesters herbicide may include phenopylate (2,4-dichlorophenyl 1-pyrrolidinecarboxylate) and carbamate analogues of phenopylate (for example, O-phenylpyrrolidino- and piperidinocarbamate analoges (refer to "Ujjana B. Nandihalli, Mary V. Duke, Stephen O. Duke, Relationships between molecular properties and biological activities of O-phenyl pyrrolidino- and piperidinocarbamate herbicides, J. Agric. Food Chem., 40(10) 1993-2000, 1992")), and the like, but not be limited thereto. In one specific embodiment, the carbamate analogue of phenopylate may be one or more selected from the group consisting of pyrrolidine-1-carboxylic acid phenyl ester (CAS No. 55379-71-0), 1-pyrrolidinecarboxylicacid, 2-chlorophenyl ester (CAS No. 143121-06-6), 4-chlorophenyl pyrrolidine-1-carboxylate (CAS No. 1759-02-0), carbamic acid, diethyl-,2,4-dichloro-5-(2-propynyloxy)phenyl ester (9CI) (CAS No. 143121-07-7), 1-pyrrolidinecarboxylicacid, 2,4-dichloro-5-hydroxyphenyl ester (CAS No. 143121-08-8), 2,4-dichloro-5-(methoxycarbonyl)phenyl pyrrolidine-1-carboxylate (CAS No. 133636-94-9), 2,4-dichloro-5-[(propan-2-yloxy)carbonyl]phenyl pyrrolidine-1-carboxylate (CAS No. 133636-96-1), 1-piperidinecarboxylic acid, 2,4-dichloro-5-(2-propynyloxy)phenyl ester (CAS No. 87374-78-5), 2,4-dichloro-5-(prop-2-yn-1-yloxy)phenyl pyrrolidine-1-carboxylate (CAS No. 87365-63-7), 2,4-dichloro-5-(prop-2-yn-1-yloxy)phenyl 4,4-difluoropiperidine-1-carboxylate (CAS No. 138926-22-4), 1-pyrrolidinecarboxylicacid, 3,3-difluoro-,2,4-dichloro-5-(2-propyn-1-yloxy)phenyl ester (CAS No. 143121-10-2), 4-chloro-2-fluoro-5-[(propan-2-yloxy)carbonyl]phenyl pyrrolidine-1-carboxylate (CAS No. 133636-98-3), and the like.

The thiadiazole-based herbicide may include fluthiacet and thidiazimin, but not be limited thereto.

The oxadiazole-based herbicide may include oxadiargyl and oxadiazon, but not be limited thereto.

The triazinone-based herbicide may include trifludimoxazin, but not be limited thereto.

The triazolinone-based herbicide may include carfentrazone, sulfentrazone, and azafenidin, but not be limited thereto.

The oxazolidinedione-based herbicide may include pentoxazone, but not be limited thereto.

The other herbicide may include pyraclonil, flufenpyrethyl, and profluazol, but not be limited thereto.

The herbicide-tolerant PPO gene provided herein may be introduced into a plant or algae by various methods known in the art, and preferably, by using an expression vector for plant or alga transformation.

In case of introducing the gene into a plant, an appropriate promoter which may be included in the vector may be any promoter generally used in the art for introduction of the gene into the plant. For example, the promoter may include an SP6 promoter, a T7 promoter, a T3 promoter, a PM promoter, a maize ubiquitin promoter, a cauliflower mosaic virus (CaMV) 35S promoter, a nopaline synthase (nos) promoter, a figwort mosaic virus 35S promoter, a sugarcane bacilliform virus promoter, a commelina yellow mottle virus promoter, a light-inducible promoter from the small subunit of ribulose-1,5-bisphosphate carboxylase (ssRUBISCO), a rice cytosolic triosephosphate isomerase (TPI) promoter, an adenine phosphoribosyltransferae (APRT) promoter of *A. thaliana*, an octopine synthase promoter, and a BCB (blue copper binding protein) promoter, but not be limited thereto.

Further, the vector may include a poly A signal sequence causing polyadenylation of 3'-terminus, and for example, it may include NOS 3'-end derived from a nopaline synthase gene of *Agrobacterium tumefaciens*, an octopine synthase terminator derived from an octopine synthase gene of *Agrobacterium tumefaciens*, 3'-end of protease inhibitor I or II gene of tomato or potato, a CaMV 35S terminator, a rice α-amylase terminator RAmy1 A, and a phaseolin terminator, but not be limited thereto.

In addition, the case of introducing the gene into an alga, chloroplast-specific promoter, nucleus promoter, constitutive promoter, or inducible promoter may be used for introduction of the gene into the algae as a promoter. The herbicide-tolerant PPO gene or its variant provided herein may be designed in order to operationally link to 5' UTR or 3' UTR, thereby expressing function in nucleus of algae. In addition, the vector may further comprise a transcriptional regulatory sequence which is appropriate to transformation of algae. A recombinant gene conferring herbicide tolerance may be integrated to genome of nucleus or genome of chloroplast in a host alga, but not be limited thereto.

In addition, in the vector, a transit peptide required for targeting to chloroplasts may be linked to 5'-end of the PPO gene in order to express the herbicide-tolerant PPO gene in the chloroplasts.

In addition, optionally, the vector may further include a gene encoding selectable marker as a reporter molecule, and example of the selectable marker may include a gene having tolerance to an antibiotic (e.g., neomycin, carbenicillin, kanamycin, spectinomycin, hygromycin, bleomycin, chloramphenicol, ampicillin, etc.) or herbicide (glyphosate, glufosinate, phosphinothricin, etc.), but is not limited thereto.

Further, the recombinant vector for plant expression may include an *Agrobacterium* binary vector, a cointegration vector, or a general vector which has no T-DNA region but is designed to be expressed in the plant. Of them, the binary vector refers to a vector containing two separate vector systems harboring one plasmid responsible for migration consisting of left border (LB) and right border (RB) in Ti (tumor inducing) plasmid, and the other plasmid for target gene-transferring, and the vector may include a promoter region and a polyadenylation signal sequence for expression in plants.

When the binary vector or cointegration vector is used, a strain for transformation of the recombinant vector into the plant is preferably *Agrobacterium* (*Agrobacterium*-mediated transformation). For this transformation, *Agrobacterium tumefaciens* or *Agrobacterium rhizogenes* may be used. In addition, when the vector having no T-DNA region is used, electroporation, particle bombardment, polyethylene glycol-mediated uptake, and the like may be used for introduction of the recombinant plasmid into the plant.

The plant transformed with the gene by the above method may be re-differentiated into a plant through callus induction, rhizogenesis, and soil acclimatization, using a standard technique known in the relevant art.

The plant subjected to transformation herein may cover not only a mature plant but also a plant cell (containing a suspension-cultured cell), a protoplast, a callus, a hypocotyl, a seed, a cotyledon, a shoot, and the loke, which can grow to a mature plant.

Further, the scope of the transformant may include a transformant which the gene is introduced as well as a clone or progeny thereof ($T_1$ generation, $T_2$ generation, $T_3$ generation, $T_4$ generation, $T_5$ generation, or any subsequent generations). For example, the transformed plant also includes a plant having the inherited herbicide tolerance traits as sexual and asexual progeny of the plant transformed with the gene provided herein. The scope of the present invention also includes all mutants and variants showing the characteristics of the initial transformed plant, together with all hybridization and fusion products of the plant transformed with the gene provided herein. Furthermore, the scope of the present invention also includes a part of the plant, such as a seed, a flower, a stem, a fruit, a leaf, a root, a tuber, and/or a tuberous root, which is originated from a transformed plant which is transformed in advance by the method of the present invention, or a progeny thereof, and is composed of at least a part of the transformed cells.

The plant, to which the present invention is applied, is not particularly limited to, but may be at least one selected from the group consisting of monocotyledonous or dicotyledonous plants. Further, the plant may be at least one selected from the group consisting of herbaceous plants and woody plants. The monocotyledonous plant may include plants belonging to families Alismataceae, Hydrocharitaceae, Juncaginaceae, Scheuchzeriaceae, Potamogetonaceae, Najadaceae, Zosteraceae, Liliaceae, Haemodoraceae, Agavaceae, Amaryllidaceae, Dioscoreaceae, Pontederiaceae, Iridaceae, Burmanniaceae, Juncaceae, Commelinaceae, Eriocaulaceae, Gramineae (Poaceae), Araceae, Lemnaceae, Sparganiaceae, Typhaceae, Cyperaceae, Musaceae, Zingiberaceae, Cannaceae, Orchidaceae, and the like, but not be limited thereto.

The dicotyledonous plant may include plants belonging to families Diapensiaceae, Clethraceae, Pyrolaceae, Ericaceae, Myrsinaceae, Primulaceae, Plumbaginaceae, Ebenaceae, Styracaceae, Symplocaceae, Symplocaceae, Oleaceae, Loganiaceae, Gentianaceae, Menyanthaceae, Apocynaceae, Asclepiadaceae, Rubiaceae, Polemoniaceae, Convolvulaceae, Boraginaceae, Verbenaceae, Labiatae, Solanaceae, Scrophulariaceae, Bignoniaceae, Acanthaceae, Pedaliaceae, Orobanchaceae, Gesneriaceae, Lentibulariaceae, Phrymaceae, Plantaginaceae, Caprifoliaceae, Adoxaceae, Valerianaceae, Dipsacaceae, Campanulaceae, Compositae, Myricaceae, Juglandaceae, Salicaceae, Betulaceae, Fagaceae, Ulmaceae, Moraceae, Urticaceae, Santalaceae, Loranthaceae, Polygonaceae, Phytolaccaceae, Nyctaginaceae, Aizoaceae, Portulacaceae, Caryophyllaceae, Chenopodiaceae, Amaranthaceae, Cactaceae, Magnoliaceae, Illiciaceae, Lauraceae, Cercidiphyllaceae, Ranunculaceae, Berberidaceae, Lardizabalaceae, Menispermaceae, Nymphaeaceae, Ceratophyllaceae, Cabombaceae, Saururaceae, Piperaceae, Chloranthaceae, Aristolochiaceae, Actinidiaceae, Theaceae, Guttiferae, Droseraceae, Papaveraceae, Capparidaceae, Cruciferae, Platanaceae, Hamamelidaceae, Crassulaceae, Saxifragaceae, Eucommiaceae, Pittosporaceae, Rosaceae, Leguminosae, Oxalidaceae, Geraniaceae, Tropaeolaceae, Zygophyllaceae, Linaceae, Euphorbiaceae, Callitrichaceae, Rutaceae, Simaroubaceae, Meliaceae, Polygalaceae, Anacardiaceae, Aceraceae, Sapindaceae, Hippocastanaceae, Sabiaceae, Balsaminaceae, Aquifoliaceae, Celastraceae, Staphyleaceae, Buxaceae, Empetraceae, Rhamnaceae, Vitaceae, Elaeocarpaceae, Tiliaceae, Malvaceae, Sterculiaceae, Thymelaeaceae, Elaeagnaceae, Flacourtiaceae, Violaceae, Passifloraceae, Tamaricaceae, Elatinaceae, Begoniaceae, Cucurbitaceae, Lythraceae, Punicaceae, Onagraceae, Haloragaceae, Alangiaceae, Cornaceae, Araliaceae, Umbelliferae (Apiaceae)), and the like, but not be limited thereto.

In a specific embodiment, the plant may be at least one selected from the group consisting of food crops such as rice, wheat, barley, corn, soybean, potato, red bean, oat, and sorghum; vegetable crops such as Chinese cabbage, radish, red pepper, strawberry, tomato, watermelon, cucumber, cabbage, oriental melon, pumpkin, welsh anion, anion, and carrot; crops for special use such as ginseng, tobacco, cotton, soilage, forage, sesame, sugar cane, sugar beet, *Perilla* sp., peanut, rapeseed, grass, and castor-oil plant; fruit trees such as apple tree, pear tree, jujube tree, peach tree, kiwi fruit tree, grape tree, citrus fruit tree, persimmon tree, plum tree, apricot tree and banana tree; woody plants such as pine, palm oil, and eucalyptus; flowering crops such as rose, gladiolus, gerbera, carnation, chrysanthemum, lily and tulip; and fodder crops such as ryegrass, red clover, orchardgrass, alfalfa, tall fescue and perennial ryegrass, but not be limited thereto. As a specific embodiment, the plant may be at least one selected from the group consisting of dicotyledonous plants such as *arabidopsis*, potato, eggplant, tobacco, red pepper, tomato, burdock, crown daisy, lettuce, balloon flower, spinach, chard, sweet potato, celery, carrot, water dropwort, parsley, Chinese cabbage, cabbage, radish, watermelon, oriental melon, cucumber, pumpkin, gourd, strawberry, soybean, mung bean, kidney bean, and pea; and monocotyledonous plants such as rice, wheat, barley, corn, sorghum, and the like, but not be limited thereto.

The algae, to which the present invention is applied, are not particularly limited to, but may be at least one prokaryotic algae or/and eukaryotic algae. For example, the algae may be at least one selected from the group consisting of cyanobacteria, green algae, red algae, brown algae, macroalgae, microalgae, and the like.

The cyanobacteria may include phylums Chroococcales (e.g., *Aphanocapsa, Aphanothece, Chamaesiphon, Chondrocystis, Chroococcus, Chroogloeocystis, Crocosphaera, Cyanobacterium, Cyanobium, Cyanodictyon, Cyanosarcina, Cyanothece, Dactylococcopsis, Gloeocapsa, Gloeothece, Halothece, Johannesbaptistia, Merismopedia, Microcystis, Radiocystis, Rhabdoderma, Snowella, Synechococcus, Synechocystis, Thermosynechococcus, Woronichinia*), Gloeobacteria, Nostocales (e.g., *Microchaetaceae, Nostocaceae, Rivulariaceae, Scytonemataceae*), Oscillatoriales (e.g., *Arthronema, Arthrospira, Blennothrix, Crinalium, Geitlerinema, Halomicronema, Halospirulina, Hydrocoleum, Jaaginema, Katagnymene, Komvophoron, Leptolyngbya, Limnothrix, Lyngbya, Microcoleus, Oscillatoria, Phormidium, Planktothricoides, Planktothrix, Plectonema, Pseudanabaena, Pseudophormidium, Schizothrix, Spirulina, Starria, Symploca, Trichodesmium, Tychonema*), Pleurocapsales (e.g., *Chroococcidiopsis, Dermocarpa, Dermocarpella, Myxosarcina, Pleurocapsa, Solentia, Stanieria, Xenococcus*), Prochlorales Stigonematales (e.g., *Capsosira, Chlorogloeopsis, Fischerella, Hapalosiphon, Mastigocladopsis, Mastigocladus, Nostochopsis, Stigonema, Symphyonema, Symphonemopsis, Umezakia, Westiellopsis*), and the like.

As another example of algae, *Chlorophyta, Chlamydomonas, Volvacales, Dunaliella, Scenedesmus, Chlorella,* or *Hematococcm* may be exemplified.

As other example of algae, *Phaeodactylum tricornutum, Amphiprora hyaline, Amphora* spp., *Chaetoceros muelleri, Navicula saprophila, Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleoabundans, Synechococcus elongatus, Botryococcus braunii, Gloeobacter violaceus, Synechocystis, Thermosynechococcus elongatus, Nannochloropsis oculata, Nannochloropsis salina, Nannochloropsis gaditana, Isochrysis galbana, Botryococcus sudeticus, Euglena gracilis, Neochloris oleoabundans, Nitzschia palea, Pleurochrysis carterae, Tetraselmis chuii, Pavlova* spp., *Aphanocapsa* spp., *Synechocystis* spp., *Nannochloris* spp., and the like may be exemplified. However, it is not limited to kinds listed above, and algae belonging to other various genus and family may be comprised.

In an embodiment, the plant or algae with the herbicide-tolerant PPO or its variant provided herein may exhibit tolerance against two or more of PPO-inhibiting herbicides.

Therefore, the technology provided by this disclosure may be used to control weeds or remove undesired aquatic organisms by using at least two PPO-inhibiting herbicides sequentially or simultaneously.

One embodiment provides a method of controlling weeds in a cropland, comprising providing the cropland with a plant comprising the herbicide-tolerant PPO protein, its variant, or a gene encoding the same as described above, and applying an effective dosage of protoporphyrinogen IX oxidase-inhibiting herbicide to the cropland and/or the plant.

Another embodiment provides a method of removing an undesired aquatic organism from a culture medium, comprising:

providing a culture medium with algae comprising the herbicide-tolerant PPO protein, its variant, or a gene encoding the same described above, and applying an effective dosage of protoporphyrinogen IX oxidase-inhibiting herbicide to the culture medium.

In addition, the herbicide-tolerant PPO protein, its variant, or a gene encoding the same provided herein may be used in combination of a second herbicide-tolerant polypeptide or a gene encoding the same.

Therefore, the plant or algae introduced with the herbicide-tolerant PPO provided herein may exhibit tolerance against two or more of herbicides which are different from each other in mechanism of action. In the present invention, two or more of different herbicides including the PPO-inhibiting herbicide, which are different from each other in mechanism of action, may be used sequentially or simultaneously, thereby controlling weeds and/or removing undesired aquatic organisms. Hereinafter, the herbicide which is different from the PPO-inhibiting herbicide in the mechanism of action is called "second herbicide".

One embodiment provides a composition for conferring or enhancing herbicide tolerance of plants or algae, comprising the above-described herbicide-tolerant PPO protein, its variant, or a gene encoding the same; and a second herbicide-tolerant polypeptide or a gene encoding the same.

Another embodiment provides a transformant of plants or algae having herbicide tolerance, or a clone or progeny thereof, comprising the above-described herbicide-tolerant PPO protein, its variant, or a gene encoding the same; and a second herbicide-tolerant polypeptide or a gene encoding the same.

Another embodiment provides a method of preparing plants or algae having herbicide tolerance, comprising a step of introducing the above-described herbicide-tolerant PPO protein, its variant, or a gene encoding the same and a second herbicide-tolerant polypeptide or a gene encoding the same, into an alga, or a cell, protoplast, callus, hypocotyl, seed, cotyledon, shoot, or whole body of a plant.

Another embodiment provides a method of controlling weeds in a cropland, comprising providing the cropland with a plant comprising the above-described herbicide-tolerant PPO protein, its variant, or a gene encoding the same, and a second herbicide-tolerant polypeptide or a gene encoding the same, and applying effective dosages of protoporphyrinogen IX oxidase-inhibiting herbicide and the second herbicide to the cropland simultaneously or sequently in any order.

Another embodiment provides a method of removing an undesired aquatic organism from a culture medium, comprising providing a culture medium with algae comprising the herbicide-tolerant PPO protein, its variant, or a gene encoding the same and a second herbicide-tolerant polypeptide or a gene encoding the same, and applying effective dosages of protoporphyrinogen IX oxidase-inhibiting herbicide and the second herbicide to the culture medium simultaneously or sequently in any order.

For example, the plant or algae may further comprise the second herbicide-tolerance polypeptide or a gene encoding the same, thereby having acquired and/or enhanced tolerance against the second herbicide.

For example, the plant or alga further includes the second herbicide-tolerance polypeptide or a gene encoding thereof, thereby having novel and/or enhanced tolerance against the second herbicide.

For example, the second herbicide may include cell division-inhibiting herbicides, photosynthesis-inhibiting herbicides, amino acid synthesis-inhibiting herbicides, plastid-inhibiting herbicides, cell membrane-inhibiting herbicides, and/or any combinations thereof, but is not limited thereto. The second herbicide may be exemplified by glyphosate, glufosinate, dicamba, 2,4-D (2,4-dichlorophenoxyacetic acid), ALS (acetolactate synthase)-inhibiting herbicides (for example, imidazolidinone, sulfonylurea, triazole pyrimidine, sulphonanilide, pyrimidine thiobenzoate, etc.), photosystem II-inhibiting herbicides, phenylurea-based herbicides, plastid-inhibiting herbicides, bromoxynil-based herbicides, and/or any combinations thereof, but is not limited thereto.

For example, the second herbicide-tolerant polypeptide may be exemplified as one or more kinds selected from the group consisting of glyphosate herbicide-tolerant EPSPS (glyphosate tolerant 5-enolpyruvylshikimate-3-phosphate synthase), GOX (glyphosate oxidase), GAT (glyphosate-N-acetyltransferase) or glyphosate decarboxylase; glufosinate herbicide-tolerant PAT (phosphinothricin-N-acetyltransferase); dicamba herbicide-tolerant DMO (dicamba monooxygenase); 2,4-D herbicide-tolerant 2,4-D monooxygenase or AAD (aryloxyalkanoate dioxygenase); ALS-inhibiting sulfonylurea-based herbicide-tolerant ALS (acetolactate synthase), AHAS (acetohydroxyacid synthase), or AtAHASL (*Arabidopsis thaliana* acetohydroxyacid synthase large subunit); photosystem II-inhibiting herbicide-tolerant photosystem II protein Dl; phenylurea-based herbicide-tolerant cytochrome P450; plastid-inhibiting herbicide-tolerant HPPD (hydroxyphenylpyruvate dioxygenase); bromoxynil herbicide-tolerant nitrilase; and any combinations thereof, but is not limited thereto.

Further, the gene encoding the second herbicide-tolerant polypeptide may be exemplified as one or more kinds selected from the group consisting of glyphosate herbicide-tolerant cp4 epsps, epsps (AG), mepsps, 2mepsps, goxv247, gat4601 or gat4621 gene; glufosinate herbicide-tolerant bar, pat or pat (SYN) gene; dicamba herbicide-tolerant dmo gene; 2,4-D herbicide-tolerant AAD-1 or AAD-12 gene; ALS-inhibiting sulfonylurea-based herbicide-tolerant ALS, GM-HRA, S4-HRA, ZM-HRA, Csr1, Csr1-1, Csr1-2, SurA or SurB; photosystem II-inhibiting herbicide-tolerant psba gene; phenylurea herbicide-tolerant CYP76B1 gene; isoxaflutole herbicide-tolerant HPPDPF W336 gene; bromoxynil herbicide-tolerant bxn gene; and any combinations thereof, but is not limited thereto.

Advantageous Effects

A variant of herbicide-tolerant PPO protein or a gene encoding the same provided herein may be applied to a plant or algae, thereby conferring excellent herbicide tolerance traits to the plant or algae and/or enhancing the herbicide tolerance traits of the plant or algae. In addition, a selective control can be performed using herbicides, thereby economically controlling weeds or removing aquatic organisms.

DESCRIPTION OF DRAWINGS

FIG. 1 is a map of pET303-CT-His vector.

FIG. 2 is a photograph showing cell growth level of PPO-deficient BT3 *E. coli* (BT3(ΔPPO)) transformant transformed with CyPPO16 wild type gene (indicated by CyPPO16WT), or various CyPPO16 mutant genes leading to a mutation of one amino acid, when treated with tiafenacil at a concentration of 0 μM(control), 10 μM, and 25 μM, respectively (upper), and saflufenacil at a concentration of 0 μM(control), 25 μM, and 50 μM, respectively (lower).

FIG. 3 is a photograph showing cell growth level of BT3(ΔPPO) transformant transformed with CyPPO16WT, or various CyPPO16 mutant genes leading to a mutation of one amino acid, when treated with flumioxazin at a concentration of 0 μM(control), 10 μM, and 25 μM, respectively (upper), and sulfentrazone at a concentration of 0 μM(control), 50 μM, and 100 μM, respectively (lower).

FIG. 4 is a photograph showing cell growth level of BT3(ΔPPO) transformant transformed with CyPPO16WT, or various CyPPO16 mutant genes leading to a mutation of one amino acid, when treated with fomesafen at a concentration of 0 μM(control), 50 μM, and 100 μM, respectively (upper), and acifluorfen at a concentration of 0 μM(control), 5 μM, and 10 μM, respectively (lower).

FIG. 5 is a photograph showing cell growth level of BT3(ΔPPO) transformant transformed with CyPPO16WT, or various CyPPO16 mutant genes leading to a mutation of one amino acid, when treated with pentoxazone at a concentration of 0 μM(control), 5 μM, and 25 μM, respectively (upper), and pyraflufen-ethyl at a concentration of 0 μM(control), 5 μM, and 25 μM, respectively (lower).

FIG. 6 is a photograph showing cell growth level of BT3(ΔPPO) transformant transformed with CyPPO16WT, or various CyPPO16 mutant genes leading to a mutation of one amino acid, when treated with pyraclonil at a concentration of 0 μM(control), 50 μM, and 100 μM, respectively.

FIGS. 7 to 17 are photographs showing cell growth level of BT3(ΔPPO) transformants transformed with CyPPO16 wild type gene (indicated by CyPPO16WT), or various CyPPO16 mutant genes leading to mutations of two or more amino acids as shown in Table 8, when treated with tiafenacil at a concentration of 0 μM(control), 50 μM, and 200 μM, sulfentrazone at a concentration of 0 μM(control), 2000 μM, and 4000 μM, and flumioxazin at a concentration of 0 μM(control), 25 μM, and 50 μM, respectively.

FIG. 18 is a photograph showing cell growth level of PPO-deficient BT3 *E. coli* (BT3(ΔPPO)) transformant transformed with CyPPO17 wild type gene (indicated by CyPPO17WT), or various CyPPO17 mutant genes leading to a mutation of one amino acid, when treated with tiafenacil at a concentration of 0 μM(control), 50 μM, and 100 μM, respectively (upper), and saflufenacil at a concentration of 0 μM(control), 50 μM, and 200 μM, respectively (lower).

FIG. 19 is a photograph showing cell growth level of BT3(ΔPPO) transformant transformed with CyPPO17WT, or various CyPPO17 mutant leading to a mutation of one amino acid, when treated with flumioxazin at a concentration of 0 μM(control), 50 μM, and 100 μM, respectively (upper), and sulfentrazone at a concentration of 0 μM(control), 5 μM, and 25 μM, respectively (lower).

FIG. 20 is a photograph showing cell growth level of BT3(ΔPPO) transformant transformed with CyPPO17WT, or various CyPPO17 mutant genes leading to a mutation of one amino acid, when treated with fomesafen at a concentration of 0 μM(control), 5 μM, and 25 μM, respectively (upper), and acifluorfen at a concentration of 0 μM(control), 5 μM, and 25 μM, respectively (lower).

FIG. 21 is a photograph showing cell growth level of BT3(ΔPPO) transformant transformed with CyPPO17WT, or various CyPPO17 mutant genes leading to a mutation of one amino acid, when treated with pyraclonil at a concentration of 0 μM(control), 5 μM, and 25 μM, respectively (upper), and pentoxazone at a concentration of 0 μM(control), 5 μM, and 25 μM, respectively (lower).

FIG. 22 is a photograph showing cell growth level of BT3(ΔPPO) transformant transformed with CyPPO17WT, or various CyPPO17 mutant genes leading to a mutation of one amino acid, when treated with pyraflufen-ethyl at a concentration of 0 μM(control), 5 μM, and 10 μM, respectively.

FIGS. 23 to 33 are photographs showing cell growth level of BT3(ΔPPO) transformants transformed with CyPPO17 wild type gene (indicated by CyPPO17WT), or various CyPPO17 mutant genes leading to mutations of two or more amino acids as shown in Table 10, when treated with tiafenacil at a concentration of 0 μM(control), 50 μM, and 200 μM, sulfentrazone at a concentration of 0 μM(control), 200 μM, and 400 μM, and flumioxazin at a concentration of 0 μM(control), 100 μM, and 200 μM, respectively.

FIG. 34 is a map of pMAL-c2X vector.

FIG. 35 is a photograph showing results observed at the $3^{rd}$ day after spraying luM of tiafenacil to *A. thaliana* ($T_2$) transformed with wild type CyPPO16 gene or with wild type CyPPO17 gene.

FIG. 36 is a photograph showing results observed at the $3^{rd}$ day after spraying 5 μM of tiafenacil to *A. thaliana* ($T_2$) transformed with wild type CyPPO16 gene, wild type CyPPO17 gene, or mutant genes thereof.

MODE FOR INVENTION

Hereinafter, the present invention will be described in detail with reference to Examples. However, these Examples are for illustrative purposes only, and the invention is not intended to be limited by these Examples.

Example 1. Verification of Herbicide Tolerance of CyPPO16 and CyPPO17 Isolated from Prokaryotes PPO gene sequences were obtained from Genebank database of two strains, *Spirulina subsalsa* and *Thermosynechococcus* sp. NK55a, respectively. For encoding the PPO protein (CyPPO16; SEQ ID NO: 1) from *Spirulina subsalsa*, the PPO gene designated as CyPPO16 was isolated from *Spirulina subsalsa*, and optimized to have the nucleic acid sequence of SEQ ID NO: 7. For encoding the PPO protein (CyPPO17; SEQ ID NO: 3) from *Thermosynechococcus* sp. NK55a, the PPO gene designated as CyPPO17 was isolated from *Thermosynechococcus* sp. NK55a and optimized to have the nucleic acid sequence of SEQ ID NO: 8. In order to obtain the herbicide-binding structure of PPO protein, the herbicides including tiafenacil, saflufenacil, flumioxazin, and sulfentrazone and the PPO proteins including CyPPO16 and CyPPO17 were used. Homology models of CyPPO16 and CyPPO17 were constructed from CyPPO10 (the PPO protein originated from *Thermosynechococcus elongatus* BP-1; SEQ ID NO: 5) structure using SWISS-MODEL protein structure modelling server (https://swissmodel.expasy.org/).

Herbicide-interacting structural information of each PPO protein was obtained after modelled structures of CyPPO16 and CyPPO17 were superimposed with CyPPO10 bound with herbicides (tiafenacil, saflufenacil, flumioxazin, and sulfentrazone).

Herbicide-binding information of CyPPO10 was obtained by following procedures: CyPPO10 protein (SEQ ID NO: 5) and tiafenacil, saflufenacil, flumioxazin, and sulfentrazone were examined as the representative protein and herbicides, respectively. The gene encoding the CyPPO10 protein (SEQ ID NO: 6) was cloned to pET29b vector (Catalog Number: 69872-3; EMD Biosciences), and CyPPO10 protein was expressed in E. coli. The expressed CyPPO10 protein was purified through nickel affinity chromatography, to which tiafenacil, saflufenacil, flumioxazin or sulfentrazone was added respectively and herbicide-bound PPO crystals were obtained. Then, the crystals were used for X-ray diffraction by synchrotron radiation accelerator. X-ray diffraction data of the 2.4 Å resolution of CyPPO10-herbicide complex crystals was obtained, and the three-dimensional structure was determined. Binding information was obtained through analyzing the amino acid residues of CyPPO10 interacting with herbicides.

Using the information of herbicide-interacting amino acids derived from the structure of CyPPO10-herbicide complexes, information of CyPPO16 and CyPPO17 amino acid residues which possibly lower the binding affinity of herbicides through mutations were determined.

As results, amino acid residues including R85, F156, V160, A162, G163, V305, C307, F324, L327, L337, I340 and F360 of CyPPO16 protein (SEQ ID NO: 1) were involved to interact with PPO-inhibiting herbicides, and those including R88, F160, V164, A166, G167, V304, C306, F323, L326, L336, I339 and F359 of CyPPO17 protein (SEQ ID NO: 3) were involved to interact with PPO-inhibiting herbicides.

Example 2. Construction of PPO Variants

In order to enhance PPO-inhibiting herbicide tolerance of CyPPO16 and CyPPO17, a mutation(s) at the position interacting with herbicide obtained in the Example 1 was introduced, respectively. Each PPO gene was codon-optimized and synthesized (Cosmogenetech Co., Ltd.) for efficient herbicide tolerance test using BT3, a PPO-deficient E. coli stain.

Detailed experimental procedure was as follows:

Using primers listed in Table 2, PCR was carried out to amplify PPO genes under following condition.
PCR reaction mixture
Template (synthetic DNA of CyPPO16 or CyPPO17) 1 µl
10× buffer 5 µl
dNTP mixture (10 mM each) 1 µl
Forward primer (10 µM) 1 µl
Reverse primer (10 µM) 1 µl
DDW 40 µl
Pfu-X (Solgent, 2.5 units/µl) 1 µl
Total 50 µl

TABLE 1

| PCR reaction condition | | |
|---|---|---|
| 94° C. | 4 min. | 1 cycle |
| 94° C. | 30 sec. | 25 cycles |
| 56° C. | 30 sec. | |
| 72° C. | 1.5 min. | |
| 72° C. | 5 min. | 1 cycle |
| 4° C. | 5 min. | 1 cycle |

TABLE 2

Primer list for cloning of CyPPO16 and CyPPO17 in pET303-CT His vector

| Strain | Primer | Sequence | SEQ ID NO. |
|---|---|---|---|
| Spirulina subsalsa | CyPPO16_XbaI F | CCCCTCTAGAATGCTAGA CTCCCTGATTGT | 9 |
| | CyPPO16_XhoI R | CCCCCTCGAGCTCCCTGC TTCTAATTTTTTG | 10 |
| Thermo- synechococcus sp. NK55a | CyPPO17_XbaI F | CCCCTCTAGAATGGAGGT CGATGTTGCAAT | 11 |
| | CyPPO17_XhoI R | CCCCCTCGAGGGATTGCC CCCCACTCAGGT | 12 |

Amplified PCR products above and pET303-CT His vector (VT0163; Novagen; FIG. 1) were digested with XbaI and XhoI restriction enzymes, and ligated to construct pET303-CyPPO16 and pET303-CyPPO17 plasmids using T4 DNA ligase (RBC, 3 units/µl).

CyPPO16 and CyPPO17 genes cloned in pET303-CT His vector were mutated through site-directed mutagenesis using primers listed in Tables 4 and 5, respectively.
PCR reaction mixture
Template 1 µl
10× buffer 5 µl
dNTP mixture (10 mM each) 1 µl
Forward primer (10 µM) 1 µl
Reverse primer (10 µM) 1 µl
DDW 40 µl
Pfu-X (Solgent, 2.5 units/µl) 1 µl
Total 50 µl

TABLE 3

| PCR reaction condition | | |
|---|---|---|
| 94° C. | 2 min. | 1 cycle |
| 94° C. | 30 sec. | 17-25 cycles |
| 65° C. | 40 sec. | |
| 72° C. | 3.5 min. | |
| 72° C. | 5 min. | 1 cycle |
| 4° C. | 5 min. | 1 cycle |

TABLE 4

Primer list for mutagenesis of CyPPO16 gene

| CyPPO16 mutation | | Primer sequence (5'->3') | SEQ ID NO |
|---|---|---|---|
| F360M | F | CATCTGCTGACCAATATGATCGGCGGCGCAACG | 13 |
| | R | CGTTGCGCCGCCGATCATATTGGTCAGCAGATG | 14 |
| F360L | F | GACCAATTTGATCGGCGGCGCAACGGACCCTG | 15 |
| | R | CGCCGATCAAATTGGTCAGCAGATGCTCACCC | 16 |
| F360I | F | CATCTGCTGACCAATATCATCGGCGGCGCAACG | 17 |
| | R | CGTTGCGCCGCCGATGATATTGGTCAGCAGATG | 18 |
| F360C | F | TGACCAATTGCATCGGCGGCGCAACGGACCCTG | 19 |
| | R | CGCCGATGCAATTGGTCAGCAGATGCTCACCC | 20 |
| F360V | F | CTGACCAATGTCATCGGCGGCGCAACGGACCC | 21 |
| | R | GCCGATGACATTGGTCAGCAGATGCTCACCCTC | 22 |
| F360T | F | CATCTGCTGACCAATACCATCGGCGGCGCAACG | 23 |
| | R | CGTTGCGCCGCCGATGGTATTGGTCAGCAGATG | 24 |

TABLE 4-continued

Primer list for mutagenesis of CyPPO16 gene

| CyPPO16 mutation | | Primer sequence (5'->3') | SEQ ID NO |
|---|---|---|---|
| V305L | F | TATCCTCCGCTAGCCTGCGTAGTCCTAGCATAC | 25 |
| | R | CGCAGGCTAGCGGAGGATAGTAAATTTCCTTG | 26 |
| A162L | F | GTCTCCGGTGTGTATCTTGGCGACGTTGATCAA | 27 |
| | R | TTGATCAACGTCGCCAAGATACACACCGGAGAC | 28 |
| A162C | F | GTCTCCGGTGTGTATTGTGGCGACGTTGATCAA | 29 |
| | R | TTGATCAACGTCGCCACAATACACACCGGAGAC | 30 |
| V305M | F | ATTTACTATCCTCCGATGGCCTGCGTAGTCCTA | 31 |
| | R | TAGGACTACGCAGGCCATCGGAGGATAGTAAAT | 32 |
| R85A | F | GACAGACGTCTACCGGCGTTTGTGTATTGGAAC | 33 |
| | R | GTTCCAATACACAAACGCCGGTAGACGTCTGTC | 34 |
| F156A | F | CGTTTAGTCGCACCAGCGGTCTCCGGTGTGTATG | 35 |
| | R | CATACACACCGGAGACCGCTGGTGCGACTAAACG | 36 |
| V160C | F | CCATTTGTCTCCGGTTGCTATGCTGGCGACGTTG | 37 |
| | R | CAACGTCGCCAGCATAGCAACCGGAGACAAATGG | 38 |
| F324V | F | CGTCCATTGGAAGGTGTGGGTCATCTTATACCC | 39 |
| | R | GGGTATAAGATGACCCACACCTTCCAATGGACG | 40 |
| L327T | F | GAAGGTTTTGGTCATACCATACCCAGGAATCAG | 41 |
| | R | CTGATTCCTGGGTATGGTATGACCAAAACCTTC | 42 |
| I340T | F | AGGACTCTTGGTACAACCTGGTCCTCCTGTCTC | 43 |
| | R | GAGACAGGAGGACCAGGTTGTACCAAGAGTCCT | 44 |
| V160C + A162C | F | TGTCTCCGGTTGCTATTGTGGCGACGTTGATCAAC | 45 |
| | R | GTTGATCAACGTCGCCACAATAGCAACCGGAGACA | 46 |
| V160C + A162L | F | CGCACCATTTGTCTCCGGTTGCTATCTTGGCGACGTTGATCAACTATC | 47 |
| | R | GATAGTTGATCAACGTCGCCAAGATAGCAACCGGAGACAAATGGTGCG | 48 |

TABLE 5

Primer list for mutagenesis of CyPPO17 gene

| CyPPO17 mutation | | Primer sequence (5'->3') | SEQ ID NO |
|---|---|---|---|
| F359M | F | CAAGTTTTTACTTCAATGATCGGTGGAGCAACA | 49 |
| | R | TGTTGCTCCACCGATCATTGAAGTAAAAACTTG | 50 |
| F359C | F | CCACCGATGCATGAAGTAAAAACTTGCCACCC | 51 |
| | R | TTTACTTCATGCATCGGTGGAGCAACAGATCCG | 52 |
| F359L | F | TCCACCGATCAATGAAGTAAAAACTTGCCACCC | 53 |
| | R | TTACTTCATTGATCGGTGGAGCAACAGATCCGG | 54 |
| F359I | F | CAAGTTTTTACTTCAATCATCGGTGGAGCAACA | 55 |
| | R | TGTTGCTCCACCGATGATTGAAGTAAAAACTTG | 56 |
| F359V | F | CAAGTTTTTACTTCAGTCATCGGTGGAGCAACA | 57 |
| | R | TGTTGCTCCACCGATGACTGAAGTAAAAACTTG | 58 |
| F359T | F | CAAGTTTTTACTTCAACCATCGGTGGAGCAACAG | 59 |
| | R | CTGTTGCTCCACCGATGGTTGAAGTAAAAACTTG | 60 |

TABLE 5-continued

Primer list for mutagenesis of CyPPO17 gene

| CyPPO17 mutation | | Primer sequence (5'->3') | SEQ ID NO |
|---|---|---|---|
| V304L | F | TATCCAACACTGGCCTGTGTAGTACTCGCC | 61 |
| | R | CACAGGCCAGTGTTGGATACGGAATGGCCGC | 62 |
| A166L | F | GTCTCTGGCGTGTATCTGGGAGATCCCCAGCAA | 63 |
| | R | TTGCTGGGGATCTCCCAGATACACGCCAGAGAC | 64 |
| A166C | F | GTCTCTGGCGTGTATTGCGGAGATCCCCAGCAA | 65 |
| | R | TTGCTGGGGATCTCCGCAATACACGCCAGAGAC | 66 |
| V304M | F | ATTCCGTATCCAACAATGGCCTGTGTAGTACTC | 67 |
| | R | GAGTACTACACAGGCCATTGTTGGATACGGAAT | 68 |
| F160A | F | CGTCTGGTGGCACCTGCGGTCTCTGGCGTGTATG | 71 |
| | R | CATACACGCCAGAGACCGCAGGTGCCACCAGACG | 72 |
| V164C | F | CCTTTCGTCTCTGGCTGCTATGCGGGAGATCCC | 73 |
| | R | GGGATCTCCCGCATAGCAGCCAGAGACGAAAGG | 74 |
| F323V | F | GTCAGTACGACCAGGCGTGGGCGTCCTTATACCC | 75 |
| | R | GGGTATAAGGACGCCCACGCCTGGTCGTACTGAC | 76 |
| L326T | F | GGCTTTGGCGTCACTATACCCCGTGGCCAAGGTATCCGTACA | 77 |
| | R | GCCACGGGGTATAGTGACGCCAAAGCCTGGTCGTACTGACCT | 78 |
| I339T | F | CGTACACTCGGCACTACCTGGTCTAGCTGCTTA | 79 |
| | R | TAAGCAGCTAGACCAGGTAGTGCCGAGTGTACG | 80 |
| V164C + A166L | F | CCTTTCGTCTCTGGCTGCTATCTGGGAGATCCCCAGCAA | 81 |
| | R | TTGCTGGGGATCTCCCAGATAGCAGCCAGAGACGGAAAG | 82 |
| V164C + A166C | F | TTCGTCTCTGGCTGCTATTGCGGAGATCCCCAG | 83 |
| | R | CTGGGGATCTCCGCAATAGCAGCCAGAGACGAA | 84 |

One μl of DpnI (NEB) was treated to each 10 μl of PCR products, and incubated at 37° C. for 30 minutes. DH5alpha competent cell (Biofact Co., Ltd.) was transformed with reaction solution through heat shock method, and was cultured in LB agar media containing carbenicillin (Gold Biotechnology Co., Ltd.). After plasmids were prepared from transformed E. coli, they were sequenced (Cosmogenetech, Co., Ltd.) and confirmed to have correct mutations.

Example 3. Verification of PPO-Inhibiting Herbicide Tolerance of PPO Variants (Test in E. coli)

The mutated CyPPO gene obtained from the Example 2 was transformed to BT3 (ΔPPO) strain which is deficient of PPO activity and cultured in LB media with PPO-inhibiting herbicide, thereby examining whether growth of transformed BT3 was not inhibited.

BT3 (ΔPPO) strain was provided by Hokkaido University (Japan) and it is an E. coli strain which is deficient in hemG-type PPO and has kanamycin resistance (refer to "Watanabe N, Che F S, Iwano M, Takayama S, Yoshida S, Isogai A. Dual targeting of spinach protoporphyrinogen IX oxidase II to mitochondria and chloroplasts by alternative use of two in-frame initiation codons, J. Biol. Chem. 276 (23):20474-20481, 2001; Che F S, Watanabe N, Iwano M, Inokuchi H, Takayama S, Yoshida S, Isogai A. Molecular Characterization and Subcellular Localization of Protoporphyrinogen IX oxidase in Spinach Chloroplasts, Plant Physiol. 124(1):59-70, 2000").

Detailed experimental procedure was as follows:

BT3 competent cells were transformed with the pET303-CyPPO16 and pET303-CyPPO17 plasmids and those with a mutation(s) constructed in Example 2 respectively, and were cultured in LB agar media containing carbenicillin (Gold Biotechnology, Co., Ltd.).

Single colony of E. coli transformed with each CyPPO gene was cultured in 3 ml of LB broth containing carbenicillin overnight, and then was subcultured until absorbance (0D600) reached 0.5 to 1. Then, it was diluted with LB broth to $OD_{600}=0.5$. Again, the diluted solution was serially diluted 4 times by a factor of one tenth.

The LB agar media (LB 25 g/l, Bacto agar 15 g/l) containing carbenicillin (100 μg/ml) and 0 to 4,000 μM of various herbicides dissolved in DMSO was prepared. Next, 10 μl of each diluted solution was dropped on the plate and cultured at 37° C. under light (Tables 7 and 9, FIGS. 2 to 6, and 18 to 22) or dark (Tables 8 and 10, FIGS. 7 to 17, and 23 to 33) for 16 to 20 hours. Then, extent of tolerance was evaluated. PPO-inhibiting herbicides used in the experiments were listed in Table 6:

TABLE 6

| PPO-inhibiting herbicides used in the experiments | |
|---|---|
| Family | Herbicide |
| Pyrimidinedione | tiafenacil |
|  | saflufenacil |
| Diphenyl ether | fomesafen |
|  | acifluorfen |
| N-phenylphthalimides | flumioxazin |
| Triazolinones | sulfentrazone |
| Oxazolidinediones | pentoxazone |
| Phenylpyrazoles | pyraflufen-ethyl |
| Others | pyraclonil |

The extent of herbicide tolerance of the mutated genes was evaluated by comparing that of mutated genes with that of wild type. The relative tolerance was represented with "+" as a factor of 10 times. Evaluation result was listed in Tables 7 to10 and FIGS. 2 to 33:

TABLE 7

| Herbicide tolerance evaluation of mutated CyPPO16 | | | | | | |
|---|---|---|---|---|---|---|
| No. | Mutation site | tiafenacil | saflufenacil | flumioxazin | sulfentrazone | fomesafen |
| 1 | A162C (AC) | + | +++ | ++ | + | ++ |
| 2 | A162L (AL) | + | +++ | +++ | + | ++ |
| 3 | V305M (VM) | + | +++ | + | N.T | ++ |
| 4 | F360V (FV) | +++ | +++ | +++ | + | + |
| 5 | F360C (FC) | ++ | +++ | + | ++ | ++ |
| 6 | F360L (FL) | +++ | +++ | +++ | + | +++ |
| 7 | F360M (FM) | +++ | +++ | +++ | + | +++ |
| 8 | F360I (FI) | +++ | +++ | +++ | ++ | + |
|  | WT | − | − | − | − | − |

| No. | Mutation site | acifluorfen | pentoxazone | pyraflufen-ethyl | pyraclonil |
|---|---|---|---|---|---|
| 1 | A162C (AC) | ++ | ++ | +++ | ++ |
| 2 | A162L (AL) | ++ | ++ | +++ | ++ |
| 3 | V305M (VM) | ++ | + | +++ | + |
| 4 | F360V (FV) | + | + | ++ | + |
| 5 | F360C (FC) | ++ | ++ | +++ | ++ |
| 6 | F360L (FL) | + | + | ++ | + |
| 7 | F360M (FM) | + | + | ++ | + |
| 8 | F360I (FI) | + | + | ++ | + |
|  | WT | − | − | − | − |

N.T (Not tested)

TABLE 8

Herbicide tolerance evaluation of mutated CyPPO16

| No. | Mutation site | tiafenacil | flumioxazin | sulfentrazone |
|---|---|---|---|---|
| 1 | R85A + F360I | +++++ | +++++ | +++ |
| 2 | R85A + F360V | +++ | +++ | +++ |
| 3 | R85A + F360M | +++ | +++ | +++ |
| 4 | V160C + F360I | +++ | ++++ | +++ |
| 5 | V160C + F360V | +++ | +++ | +++ |
| 6 | V160C + F360M | +++ | ++++ | +++ |
| 7 | A162L + F360I | ++++ | ++++ | + |
| 8 | A162L + F360V | ++++ | ++++ | ++++ |
| 9 | A162L + F360M | +++++ | +++++ | +++ |
| 10 | A162C + F360I | ++++ | +++ | +++ |
| 11 | A162C + F360V | ++++ | ++++ | +++ |
| 12 | A162C + F360M | +++++ | +++++ | ++++ |
| 13 | V305M + F360I | +++++ | +++++ | ++ |
| 14 | V305M + F360V | ++++ | ++++ | + |
| 15 | V305M + F360M | +++ | ++++ | + |
| 16 | L327T + F360I | +++++ | +++++ | +++ |
| 17 | L327T + F360V | ++++ | ++++ | +++++ |
| 18 | L327T + F360M | ++++ | ++++ | ++ |
| 19 | R85A + V160C + F360I | +++++ | +++++ | ++++ |
| 20 | R85A + A162L + F360M | +++++ | +++++ | ++++ |
| 21 | R85A + V305M + F360I | +++++ | +++++ | ++++ |
| 22 | R85A + L327T + F360M | +++++ | +++++ | ++++ |
| 23 | V160C + A162L + F360I | ++++ | ++++ | +++ |
| 24 | V160C + V305M + F360M | +++++ | +++++ | +++ |
| 25 | V160C + L327T + F360I | +++++ | +++++ | ++++ |
| 26 | A162L + V305M + F360M | +++++ | +++++ | ++++ |
| 27 | A162C + L327T + F360M | +++++ | +++++ | ++++ |
| 28 | V305M + L327T + F360M | +++++ | +++++ | ++++ |
| 29 | R85A + V160C + A162L + F360I | +++++ | +++++ | +++++ |
| 30 | R85A + V160C + V305M + F360M | +++++ | +++++ | ++++ |
| 31 | R85A + V160C + L327T + F360I | +++++ | +++++ | +++++ |
| 32 | R85A + A162L + V305M + F360M | +++++ | +++++ | ++++ |
| 33 | R85A + V305M + L327T + F360M | +++++ | +++++ | +++++ |
| 34 | V160C + A162L + V305M + F360I | +++++ | +++++ | +++++ |
| 35 | V160C + A162C + L327T + F360M | +++++ | +++++ | +++++ |
| 36 | A162C + V305M + L327T + F360M | +++++ | +++++ | ++++ |
| 37 | R85A + V160C + A162L + V305M + F360M | +++++ | +++++ | +++++ |
| 38 | V160C + A162C + V305M + L327T + F360M | +++++ | +++++ | +++++ |
|  | WT | − | − | − |

TABLE 9

Herbicide tolerance evaluation of mutated CyPPO17

| No. | Mutation site | tiafenacil | saflufenacil | flumioxazin | sulfentrazone | fomesafen |
|---|---|---|---|---|---|---|
| 1 | A166C (AC) | + | +++ | ++ | + | + |
| 2 | A166L (AL) | ++ | +++ | ++ | ++ | ++ |
| 3 | V304M (VM) | ++ | +++ | ++ | N.T | ++ |
| 4 | V304L (VL) | + | + | N.T | N.T | N.T |
| 5 | F359M (FM) | ++ | +++ | ++ | ++ | ++ |
| 6 | F359I (FI) | ++ | +++ | ++ | ++ | + |
| 7 | F359L (FL) | ++ | +++ | ++ | ++ | + |
| 8 | F359C (FC) | ++ | +++ | ++ | + | + |
| 9 | F359V (FV) | ++ | +++ | ++ | ++ | + |
|  | WT | − | − | − | − | − |

| No. | Mutation site | acifluorfen | pyraclonil | pentoxazone | pyraflufen-ethyl |
|---|---|---|---|---|---|
| 1 | A166C (AC) | +++ | N.T | + | ++ |

TABLE 9-continued

Herbicide tolerance evaluation of mutated CyPPO17

| | | | | | |
|---|---|---|---|---|---|
| 2 | A166L (AL) | +++ | + | ++ | ++ |
| 3 | V304M (VM) | +++ | N.T | + | + |
| 4 | V304L (VL) | N.T | N.T | N.T | N.T |
| 5 | F359M (FM) | +++ | + | ++ | ++ |
| 6 | F359I (FI) | + | + | ++ | ++ |
| 7 | F359L (FL) | + | + | + | ++ |
| 8 | F359C (FC) | + | + | + | + |
| 9 | F359V (FV) | + | + | ++ | ++ |
| | WT | − | − | − | − |

N.T (Not tested)

TABLE 10

Herbicide tolerance evaluation of mutated CyPPO17

| No. | Mutation site | tiafenacil | flumioxazin | sulfentrazone |
|---|---|---|---|---|
| 1 | R88A + F359I | ++ | ++ | ++ |
| 2 | R88A + F359V | ++ | ++ | ++ |
| 3 | R88A + F359M | ++++ | ++++ | ++++ |
| 4 | V164C + F359I | ++ | +++ | +++ |
| 5 | V164C + F359V | ++ | +++ | +++ |
| 6 | V164C + F359M | ++ | ++ | ++ |
| 7 | A166L + F359I | ++++ | ++++ | +++ |
| 8 | A166L + F359V | ++++ | +++ | +++ |
| 9 | A166L + F359M | ++++ | ++++ | +++ |
| 10 | A166C + F359I | ++++ | ++++ | ++++ |
| 11 | A166C + F359V | +++ | +++ | ++++ |
| 12 | A166C + F359M | +++ | +++ | +++ |
| 13 | V304M + F359I | +++ | +++ | ++ |
| 14 | V304M + F359V | +++ | +++ | ++ |
| 15 | V304M + F359M | +++ | +++ | ++ |
| 16 | L326T + F359I | ++++ | ++++ | +++ |
| 17 | L326T + F359V | ++++ | ++++ | +++ |
| 18 | L326T + F359M | ++++ | ++++ | +++ |
| 19 | R88A + V164C + F359I | ++++ | ++++ | ++++ |
| 20 | R88A + A166L + F359M | +++++ | +++++ | ++++ |
| 21 | R88A + V304M + F359I | ++++ | ++++ | +++ |
| 22 | R88A + L326T + F359M | +++++ | +++++ | ++++ |
| 23 | V164C + A166L + F359I | +++++ | +++++ | ++++ |
| 24 | V164C + V304M + F359M | ++++ | ++++ | +++ |
| 25 | V164C + L326T + F359I | ++++ | ++++ | +++ |
| 26 | A166L + V304M + F359M | ++++ | ++++ | +++ |
| 27 | A166L + L326T + F359I | +++++ | +++++ | ++++ |
| 28 | V304M + L326T + F359M | ++++ | ++++ | +++ |
| 29 | R88A + V164C + A166L + F359I | +++++ | +++++ | ++++ |
| 30 | R88A + V164C + V304M + F359I | +++++ | +++++ | ++++ |
| 31 | R88A + V164C + L326T + F359M | +++++ | +++++ | ++++ |
| 32 | R88A + A166L + V304M + F359I | +++++ | +++++ | +++ |
| 33 | R88A + A166L + L326T + F359M | +++++ | +++++ | ++++ |
| 34 | R88A + V304M + L326T + F359M | +++++ | +++++ | ++++ |
| 35 | V164C + A166L + V304M + F359I | +++++ | +++++ | ++++ |
| 36 | V164C + A166L + L326T + F359M | +++++ | +++++ | ++++ |
| 37 | A166L + V304M + L326T + F359I | +++++ | +++++ | ++++ |
| 38 | R88A + V164C + A166L + V304M + F359I | +++++ | +++++ | ++++ |
| 39 | R88A + V164C + A166L + L326T + F359M | +++++ | +++++ | ++++ |
| 40 | V164C + A166L + V304M + L326T + F359M | +++++ | +++++ | ++++ |
| 41 | R88A + V164C + A166C + V304M + L326T + F359M | +++++ | +++++ | ++++ |
| | WT | − | − | − |

In Tables 7 to 10, tolerance level was presented as of tolerance of wild type and of variants equivalent to that of wild type, and was done as '+' per each 10 fold resistance until '+++++' as maximal resistance. (Tolerance level was evaluated by relative growth level of variants to that of wild type in the media containing highest concentration of herbicide; '+'=1-9 fold higher tolerance, '++'=10-99 fold higher tolerance, '+++'=100-999 fold higher tolerance, '++++'=1,000-9,999 fold higher tolerance, '+++++'=more than 10,000 fold higher tolerance)

FIGS. 2 to 17 show the tolerance of CyPPO16 wild type and its variants, and FIGS. 18 to 33 show that of CyPPO17 wild type and its variants. The concentrations of herbicides were written above the photographs of tolerance test. A dilution series (OD600=0.5, 0.05, 0.005, 0.0005, 0.00005) was made and spotted on LB agar plates supplemented with herbicides.

As shown in Tables 7 to 10 and FIGS. 2 to 33, all of BT3 strains transformed with variants of CyPPO16 or CyPPO17 showed higher tolerance level than that of wild type against various PPO-inhibiting herbicides.

Example 4: Measurement of PPO Enzyme Activity and IC$_{50}$ Value for Herbicides The enzyme activities of variants wherein amino acids of certain position of PPO protein mutated were measured and inhibition assay with the PPO-inhibiting herbicides was conducted.

Although the solubility of PPO protein is markedly low in aqueous condition, it was greatly increased when maltose binding protein (MBP) was fused to PPO protein. Thus, PPO proteins of wild type and variants were expressed as fused to MBP and were used for experiments.

In order to express wild type and variant proteins of CyPPO16 and CyPPO17, those genes were introduced into pMAL-c2x vector (refer to FIG. 34), respectively.

Detailed experimental procedure was as follows:

Using primers listed in Table 12, PCR was carried out to amplify PPO genes under following condition.

PCR reaction mixture
Template (synthetic DNA of CyPPO16 or CyPPO17) 1 μl
10× buffer 5 μl
dNTP mixture (10 mM each) 1 μl
Forward primer (10 μM) 1 μl
Reverse primer (10 μM) 1 μl
DDW 40 μl
Pfu-X (Solgent, 2.5 units/μl) 1 μl
Total 50 μl

TABLE 11

| PCR reaction condition | | |
|---|---|---|
| 94° C. | 4 min. | 1 cycle |
| 94° C. | 30 sec. | 27 cycles |
| 56° C. | 30 sec. | |
| 72° C. | 5 min. | |
| 72° C. | 5 min. | 1 cycle |
| 4° C. | 5 min. | 1 cycle |

TABLE 12

Primer list for cloning of CyPPO16 and CyPPO17 in pMAL-c2x

| Strain | Primer | Sequence | SEQ ID NO |
|---|---|---|---|
| Spirulina subsalsa | CyPPO16_BamHIF | CCCCGGATCCATGCTAGACTCCCTGATTGT | 85 |
| | CyPPO16_SalIR | CCCCGTCGACTCACTCCTGCTTCTAATTTTTTG | 86 |

TABLE 12-continued

Primer list for cloning of CyPPO16 and CyPPO17 in pMAL-c2x

| Strain | Primer | Sequence | SEQ ID NO |
|---|---|---|---|
| Thermo-synechococcus sp. NK55a | CyPPO17_BamHIF | CCCCGGATCCATGGAGGTCGATGTTGCAAT | 87 |
| | CyPPO17_SalIR | CCCCGTCGACTCAGGATTGCCCCCCACTCAGGT | 88 |

Amplified PCR products and pMAL-c2x vector (NEB, FIG. 34) were digested with BamHI and SalI restriction enzymes, and ligated to construct pMAL-c2x-CyPPO16 and pMAL-c2x-CyPPO17 plasmids using T4 DNA ligase (RBC, 3 units/μl).

CyPPO16 and CyPPO17 genes cloned in pMAL-c2x vector were mutated through site-directed mutagenesis using primers listed in Tables 4 and 5, respectively.

PCR reaction mixture
Template 1 μl
10× buffer 5 μl
dNTP mixture (10 mM each) 1 μl
Forward primer (10 μM) 1 μl
Reverse primer (10 μM) 1 μl
DDW 40 μl
Pfu-X (Solgent, 2.5 units/μl) 1 μl
Total 50 μl Then, BL21 CodonPlus(DE3) E. coli was transformed with constructs.

The transformed E. coli were cultured under the following conditions to express PPO proteins:

Induction: OD$_{600}$=0.2, addition of IPTG to 0.3 mM final concentration;
Culture temperature: 23° C., 200 rpm shaking culture;
Culture time: 16 hrs;
Culture volume: 200 ml/1,000 ml flask.

After harvesting the cells, cell lysis and protein extraction were performed by the following process:

Extraction buffer: Column buffer (50 mM Tris-Cl, pH 8.0, 200 mM NaCl) 5 ml buffer/g cell;
Sonication: SONICS&MATERIALS VCX130 (130 watts);
15 sec ON, 10 sec OFF for 5 min on ice;
Centrifugation at 4° C. for 20 minutes (20,000× g); and the supernatant obtained after the centrifugation was diluted at the ratio of 1:6 with column buffer.

The following process for purification of PPO protein was performed in a 4° C. cold room. Amylose resin (NEB) was packed to 1.5×15 cm column (Bio-Rad, Econo Columns 1.5×15 cm, glass chromatography column, max. vol), and the obtained protein extracts were loaded to the column at a flow rate of 0.2 ml/min. The column was washed with 3 column volumes of buffer and the presence of protein in the washing solution was examined. When the protein was no longer detected, the washing procedure was terminated. Then, the MBP-PPO protein was eluted with approximately 2 column volumes of buffer containing 20 mM maltose. The protein concentration of each eluent was determined and the elution was stopped when the protein was no longer detected. Ten microliter of each fraction was investigated for protein quantification and SDS-PAGE analysis. The highly pure fractions of PPO protein variants were used for the enzyme assay.

Since protoporphyrinogen IX, a substrate of PPO protein, was not commercially available, it was chemically synthesized in the laboratory. Overall process was performed in dark under nitrogen stream. Nine micrograms of protoporphyrin IX was dissolved in 20 ml of 20% (v/v) EtOH, and stirred under dark condition for 30 minutes. The obtained protoporphyrin IX solution was put into a 15 ml screw tube in an amount of 800 µl, and flushed with nitrogen gas for 5 minutes. To this, 1.5 g of sodium amalgam was added and vigorously shaken for 2 minutes. The lid was opened to exhaust hydrogen gas in the tube. Thereafter, the lid was closed and incubated for 3 minutes. The protoporphyrinogen IX solution was filtered using syringe and cellulose membrane filter. To 600 µl of the obtained protoporphyrinogen IX solution, approximately 300 µl of 2M MOPS [3-(N-morpholino) propanesulfonic acid] was added to adjust pH to 8.0. To determine the enzyme activity of PPO protein, a reaction mixture was prepared with the following composition (based on 10 ml): 50 mM Tris-Cl (pH 8.0); 50 mM NaCl; 0.04% (v/v) Tween 20; 40 mM glucose (0.072 g); 5 units glucose oxidase (16.6 mg); and 10 units catalase (1 µl).

Hundred and eighty microliters of a reaction mixture containing the purified PPO protein were placed in 96 well plates and 20 µl of purified PPO proteins were added. After 50 µl of the mineral oil was layered, the reaction was initiated by adding the substrate, protoporphyrinogen IX solution, to a final concentration of 50 µM. The reaction proceeded at room temperature for 30 min and the fluorescence of protoporphyrin IX was measured using Microplate reader (Sense, Hidex) (excitation: 405 nm; emission: 633 nm). To calculate the PPO enzyme activity, the protoporphyrinogen IX solution was kept open in the air overnight to oxidize the solution. To this, 2.7 N HCl was added, and the absorbance at 408 nm was measured. A standard curve was generated using standard protoporphyrin IX, and PPO activity was measured by calibration of protoporphyrin IX using the standard curve of protoporphyrin IX.

The enzyme activities of the obtained PPO wild type and variants were shown in Tables 14 to 15. Activities of variants were presented relatively compared to that of wild type.

Meanwhile, the maximal velocity (Vmax) values of each enzyme were determined in order to evaluate the kinetic characteristics of CyPPO16 and CyPPO17. The initial reaction velocity was measured where the reaction velocity was proportional to concentration by varying the substrate concentration. The amount of produced protoporphyrin IX, the enzyme reaction product, was measured by time course at room temperature for 20 minutes. Vmax values were calculated with the enzyme kinetics analysis program by Michaelis-Menten equation. The wild type AtPPO1 was used as a control. The result was shown in Table 13:

TABLE 13

| Vmax values of CyPPO16 and CyPPO17 | | | |
|---|---|---|---|
| | CyPPO16 | CyPPO17 | AtPPO1 |
| Vmax (nmole mg protein$^{-1}$ min$^{-1}$) | 336 | 378 | 135 |

From the above results, Vmax values of CyPPO16 and CyPPO17 were more than two times higher than that of AtPPO1. This indicates that CyPPO16 and CyPPO17 proteins possess better ability as PPO enzyme than the plant-derived AtPPO1.

In addition, the concentration of the PPO-inhibiting herbicides that inhibits the PPO enzyme activity of each PPO wild type and variants by 50% (IC$_{50}$) was measured for each herbicide. The final concentrations of each herbicide were as follows:

tiafenacil, flumioxazin and sulfentrazone: 0, 10, 50, 100, 250, 500, 1000, 2500, 5000, 10000 nM The IC$_{50}$ value, the concentration of the herbicide inhibiting the PPO enzyme activity to 50%, was calculated by adding the herbicide of the above concentrations.

The IC$_{50}$ value for each herbicide was shown in the following Tables 14 and 15.

TABLE 14

Determination of IC$_{50}$ of CyPPO16 wild type and mutants against various herbicides

| No. | Mutation site | Activity (%) | tiafenacil (nM) | flumioxazin (nM) | sulfentrazone (nM) |
|---|---|---|---|---|---|
| 1 | WT | 100 | 26 | 14 | 245 |
| 2 | R85A | 94 | 119 | 59 | 1,036 |
| 3 | F156A | 57 | 60 | N.T | N.T |
| 4 | V160C | 96 | 45 | 57 | 584 |
| 5 | A162C | 80 | 79 | N.T | N.T |
| 6 | A162L | 69 | 193 | 578 | 1,096 |
| 7 | V305M | 72 | 43 | 38 | 305 |
| 8 | F324V | 23 | 103 | N.T | N.T |
| 9 | L327T | 68 | 40 | 780 | 1,827 |
| 10 | I340T | 22 | 230 | N.T | N.T |
| 11 | F360M | 83 | 168 | 472 | 1,203 |
| 12 | F360I | 74 | 1,738 | 835 | 1,363 |
| 13 | F360V | 69 | 939 | 667 | 1,962 |
| 14 | F360T | 25 | 2,500 | N.T | N.T |
| 15 | R85A + F360M | 63 | 1,022 | 567 | >10,000 |
| 16 | F156A + F360M | 18 | 237 | N.T | N.T |
| 17 | V160C + F360M | 67 | 405 | 1,002 | 4,371 |
| 18 | A162C + F360M | 56 | 2,162 | N.T | N.T |
| 19 | A162L + F360M | 45 | >5,000 | 4,058 | >10,000 |
| 20 | V305M + F360M | 35 | 476 | 1,182 | 3,631 |
| 21 | F324V + F360M | 13 | 4,056 | N.T | N.T |
| 22 | L327T + F360M | 21 | 3,763 | 5,000 | >10,000 |
| 23 | I340T + F360M | 16 | >5,000 | N.T | N.T |
| 24 | A162C + L327T + F360M | 17 | 3,915 | >5,000 | >10,000 |
| 25 | R85A + A162C + L327T + F360M | 15 | 4,683 | >5,000 | >10,000 |

TABLE 14-continued

Determination of IC$_{50}$ of CyPPO16 wild type and mutants against various herbicides

| No. | Mutation site | Activity (%) | tiafenacil (nM) | flumioxazin (nM) | sulfentrazone (nM) |
|---|---|---|---|---|---|
| 26 | R85A + V160C + A162C + L327T + F360M | 15 | >5,000 | >5,000 | >10,000 |
| 27 | R85A + V160C + A162C + V305M + L327T + F360M | 13 | >5,000 | >5,000 | >10,000 |

N.T (Not tested)

TABLE 15

Determination of IC$_{50}$ of CyPPO17 wild type and mutants against various herbicides

| No. | Mutation site | Activity (%) | tiafenacil (nM) | flumioxazin (nM) | sulfentrazone (nM) |
|---|---|---|---|---|---|
| 1 | WT | 100 | 44 | 26 | 326 |
| 2 | R88A | 70 | 152 | 95 | 4,426 |
| 3 | F160A | 63 | 115 | N.T | N.T |
| 4 | V164C | 73 | 87 | 58 | 920 |
| 5 | A166C | 77 | 219 | N.T | N.T |
| 6 | A166L | 70 | 1,129 | 2,828 | >10,000 |
| 7 | V304M | 82 | 102 | 63 | 1,089 |
| 8 | F323V | 16 | 152 | N.T | N.T |
| 9 | L326T | 96 | 194 | 139 | >10,000 |
| 10 | I339T | 48 | 122 | N.T | N.T |
| 11 | F359M | 90 | 1,189 | 379 | 696 |
| 12 | F359I | 92 | 1,531 | 825 | >10,000 |
| 13 | F359V | 84 | 932 | 2,052 | >10,000 |
| 14 | F359T | 56 | >5,000 | N.T | N.T |
| 15 | R88A + F359M | 53 | 1,284 | 690 | >10,000 |
| 16 | F160A + F359M | 56 | 3,927 | N.T | N.T |
| 17 | V164C + F359M | 71 | 2,737 | 576 | 1,281 |
| 18 | A166C + F359M | 72 | >5,000 | N.T | N.T |
| 19 | A166L + F359M | 65 | >5,000 | >5,000 | >10,000 |
| 20 | V304M + F359M | 68 | >5,000 | 486 | 4,536 |
| 21 | F323V + F359M | 8 | 4,247 | N.T | N.T |
| 22 | L326T + F359M | 74 | 4,792 | 933 | >10,000 |
| 23 | I339T + F359M | 44 | >5,000 | N.T | N.T |

N.T (Not tested)

As shown in the Tables 14 and 15, it was demonstrated that variants of CyPPO16 and CyPPO17 proteins showed the significantly increased IC$_{50}$ values against each herbicide compared to the wild type. Such results indicate that herbicide tolerance was increased by amino acid substitutions at specified positions of PPO protein. Although the data showed that CyPPO16 and CyPPO17 protein variants possess reduced enzyme activity compared to the wild type, it might be caused by the difference between the chloroplast environment where PPO functions and in vitro assay condition. Thus, when PPO variants are properly assembled and expressed to chloroplasts in plants, the enzyme activity would not be affected drastically.

Example 5. Generation of *Arabidopsis thaliana* Transformants Using CyPPO Variants and PPO-Inhibiting Herbicide Tolerance Test 5-1. Construction of *A. thaliana* Transformation Vectors and Generation of *A. thaliana* Transformants

*A. thaliana* was transformed with a binary vector having ORF of a selectable marker, Bar gene (glufosinate-tolerant gene), and ORF of each mutant gene of CyPPO16 and CyPPO17. The transgenic plant was examined for cross-tolerance towards glufosinate and PPO-inhibiting herbicides. The bar gene was also used to examine whether the transgene was stably inherited during generations. NOS promoter and E9 terminator were used for bar gene expression.

In order to express proteins of CyPPO16, CyPPO16 variants, CyPPO17, and CyPPO17 variants in plants, a CaMV35S promoter and a NOS terminator were used. Encoding genes of CyPPO16, CyPPO16 variants, CyPPO17, and CyPPO17 variants were introduced into binary vector using XhoI and BamHI restriction enzymes. Furthermore, for confirmation of the protein expression, hemagglutinin (HA) tag was fused to the C-terminal region of PPO protein coding gene using BamHI and SacI restriction enzymes. In addition, in order to transit protein to chloroplast, transit peptide (TP) gene (SEQ ID NO: 90) of AtPPO1 gene (SEQ ID NO: 89) was fused to N-terminal region of PPO protein coding gene using XbaI and XhoI restriction enzymes.

Each constructed vector was transformed to *Agrobacterium tumefaciens* GV3101 competent cell by freeze-thaw method. *Agrobacterium* GV3101 competent cells were prepared by following procedures, *Agrobacterium* GV3101 strain was cultured in 5 ml LB media at 30° C., 200 rpm for 12 hrs. The cells were subcultured in 200 ml of LB media at 30° C., 200 rpm for 3 to 4 hrs, and centrifuged at 3,000×g at 4° C. for 20 minutes. The cell pellet was washed with sterile distilled water, and then resuspended in 20 ml of LB media. Snap frozen 200 μl aliquots with liquid nitrogen were stored in a deep freezer.

Each transformed *Agrobacterium* was screened in spectinomycin-containing LB media. The screened colony was cultured in LB broth. After *Agrobacterium* cell was harvested from the culture media, it was resuspended in the solution containing 5% sucrose (w/v) and 0.05% Silwet L-77 (v/v) (Momentive Performance Materials Co., Ltd.) at an absorbance ($OD_{600}$) of 0.8. By floral dipping method, *A. thaliana* wild type (Col-0 ecotype) was transformed, and then the $T_1$ seeds were harvested after 1 to 2 months.

Transgenic plants were screened with glufosinate tolerance which was conferred by Bar gene expression in the binary vector. The obtained $T_1$ seeds were sown in 1/2 MS media (2.25 g/l MS salt, 10 g/l sucrose, 7 g/l Agar) supplemented with 50 μM glufosinate, and the surviving plants were selected 7 days after sowing. They were, then, transplanted into soil and grown to obtain $T_1$ plants.

In order to examine PPO-inhibiting herbicide tolerance of the transgenic plants, 4-week-old plants were evenly sprayed with herbicide (100 ml of 1 μM tiafenacil and 0.05% Silwet L-77 (v/v)) in 40×60 cm area (0.24 $m^2$). While wild type *A. thaliana* (Col-0 ecotype) completely died within 7 days after treatment, each transgenic plant showed no damage to PPO-inhibiting herbicide treatment.

The $T_2$ seeds were harvested from $T_1$ transgenic plant and were sown to 1/2 MS media (2.25 g/l MS salt, 10 g/l sucrose, 7 g/l Agar) supplemented with 50 μM glufosinate. One week later, surviving plants were transplanted to soil.

5-2. Verification of Herbicide Tolerance of Transformed *Arabidopsis* Plants ($T_2$)

*Arabidopsis* plants ($T_2$) transformed with genes including CyPPO16, CyPPO16 variants (F360I, F360M, F360V, A162C+F360M), CyPPO17, or CyPPO17 variants (F359I, F359M, F359V, V304M+F359I) were tested for their tolerance against herbicides.

In order to examine PPO-inhibiting herbicide tolerance of the transgenic plants, transgenic plants of CyPPO16 wild type or CyPPO17 wild type were evenly sprayed with herbicide (100 ml of 1 μM tiafenacil and 0.05% Silwet L-77 (v/v)) in 40×60 cm area (0.24 $m^2$). Herbicide tolerance was evaluated 3 days after treatment. Wild type *Arabidopsis* plant (Col-0 ecotype) was used as a control.

The evaluated transgenic *Arabidopsis* ($T_2$) plants after 1 μM tiafenacil treatment were shown in FIG. 35.

In order to examine PPO-inhibiting herbicide tolerance of the transgenic plants, transgenic plants of CyPPO16 variants or CyPPO17 variants were evenly sprayed with herbicide (100 ml of 5 μM tiafenacil and 0.05% Silwet L-77 (v/v)) in 40×60 cm area (0.24 $m^2$). Herbicide tolerance was evaluated 3 days after treatment. Wild type *Arabidopsis* plant (Col-0 ecotype) and transgenic plants of CyPPO16 wild type or CyPPO17 wild type were used as controls.

The transgenic *Arabidopsis* ($T_2$) plants after 5 μM tiafenacil treatment were shown in FIG. 36.

Based on the results above (FIGS. 35 and 36), herbicide tolerance of transgenic plants was evaluated with Injury index defined in Table 16.

TABLE 16

Injury index definition

| Injury index | Symptom |
| --- | --- |
| 0 | No damage |
| 1 | Dried leaf tip |
| 2 | Over 20% and less than 30% of the plant was scorched |
| 2.5 | Over 30% and less than 50% of the plant was scorched |
| 3 | Over 50% and less than 70% of the plant was scorched |
| 4 | Over 70% of the plant was scorched |
| 5 | The whole plant was dried and died |

The tolerance levels of transgenic plants were evaluated according to the injury index definition and were shown in Tables 17 to 19.

TABLE 17

Injury index of transgenic plants of CyPPO16 wild type and CyPPO17 wild type after 1 μM tiafenacil treatment

|  | Col-0 | CyPPO16 wild type | CyPPO17 wild type |
| --- | --- | --- | --- |
| Injury index | 5 | 2 | 2 |

TABLE 18

Injury index of transgenic plants of CyPPO16 variants after 5 μM tiafenacil treatment

|  | Col-0 | CyPPO16 Wild type | F360I | F360M | F360V | A162C + F360M |
| --- | --- | --- | --- | --- | --- | --- |
| Injury index | 5 | 4 | 2 | 2 | 2 | 2 |

TABLE 19

Injury index of transgenic plants of CyPPO17 variants after 5 μM tiafenacil treatment

|  | Col-0 | CyPPO17 Wild type | F359I | F359M | F359V | V304M + F359I |
| --- | --- | --- | --- | --- | --- | --- |
| Injury index | 5 | 4 | 1 | 2 | 1 | 1 |

The invention claimed is:

1. A polypeptide selected from the group consisting of:
(a) a polypeptide comprising an amino acid sequence of modified SEQ ID NO: 1, wherein one or more amino acid residues selected from the group consisting of R85, F156, V160, A162, G163, V305, C307, F324, L327, L337, I340, and F360 of the amino acid sequence of SEQ ID NO: 1 are respectively and independently deleted or substituted with an amino acid selected from the group consisting of M(Met), V(Val), I(Ile), T(Thr), L(Leu), C(Cys), A(Ala), S(Ser), F(Phe), P(Pro), W(Trp), N(Asn), Q(Gln), G(Gly), Y(Tyr), D(Asp), E(Glu), R(Arg), H(His), and K(Lys), which is different from the amino acid at the corresponding position of SEQ ID NO: 1;
(b) a polypeptide comprising an amino acid sequence of modified SEQ ID NO: 3, wherein one or more amino acid residues selected from the group consisting of R88, F160, V164, A166, G167, V304, C306, F323, L326, L336, I339, and F359 of the amino acid sequence of SEQ ID NO: 3 are respectively and independently deleted or substituted with an amino acid selected from the group consisting of M(Met), V(Val), I(Ile), T(Thr), L(Leu), C(Cys), A(Ala), S(Ser), F(Phe), P(Pro), W(Trp), N(Asn), Q(Gln), G(Gly), Y(Tyr), D(Asp), E(Glu), R(Arg), H(His), and K(Lys), which is different from the amino acid at the corresponding position of SEQ ID NO: 3; and
(c) a polypeptide obtained by a chemical synthesis or recombination method and comprising an amino acid sequence with at least 95% identity with the amino acid sequence of the polypeptide (a) or (b), wherein the polypeptide (c) does not include the amino acid sequence of SEQ ID NO: 1 or 3.

2. The polypeptide of claim 1, which is selected from the group consisting of:
(a) a polypeptide comprising an amino acid sequence of modified SEQ ID NO: 1, wherein one or more amino acid residues selected from the group consisting of R85, F156, V160, A162, G163, V305, C307, F324, L327, L337, I340, and F360 of the amino acid sequence of SEQ ID NO: 1 are respectively and independently deleted or substituted with an amino acid selected from the group consisting of M(Met), V(Val), I(Ile), T(Thr), L(Leu), C(Cys), S(Ser), and A(Ala), which is different from the amino acid at the corresponding position of SEQ ID NO: 1;
(b) a polypeptide comprising an amino acid sequence of modified SEQ ID NO: 3, wherein one or more amino acid residues selected from the group consisting of R88, F160, V164, A166, G167, V304, C306, F323, L326, L336, I339, and F359 of the amino acid sequence of SEQ ID NO: 3 are respectively and independently deleted or substituted with an amino acid selected from the group consisting of M(Met), V(Val), I(Ile), T(Thr), L(Leu), C(Cys), S(Ser), and A(Ala), which is different from the amino acid at the corresponding position of SEQ ID NO: 3; and
(c) a polypeptide obtained by a chemical synthesis or recombination method and comprising an amino acid sequence with at least 95% identity with the amino acid sequence of the polypeptide (a) or (b), wherein the polypeptide (c) does not include the amino acid sequence of SEQ ID NO: 1 or 3.

3. The polypeptide of claim 1, which is selected from the group consisting of:
(a) a polypeptide comprising an amino acid sequence having modification to SEQ ID NO: 1, wherein the modification comprises at least one amino acid mutation selected from the group consisting of F360M, F360L, F360I, F360C, F360V, F360T, V305I, V305L, A162L, A162C, A162I, V305M, R85A, F156A, V160C, V160S, F324V, L327T, and I340T, in the amino acid sequence of SEQ ID NO: 1;
(b) a polypeptide comprising an amino acid sequence of having modification to SEQ ID NO: 3, wherein the modification comprises at least one amino acid mutation selected from the group consisting of F359M, F359C, F359L, F359I, F359V, F359T, V304I, V304L, A166L, A166C, A166I, V304M, R88A, F160A, V164C, V164S, F323V, L326T, and I339T, in the amino acid sequence of SEQ ID NO: 3;
(c) a polypeptide obtained by a chemical synthesis or recombination method and comprising an amino acid sequence with at least 95% identity with the amino acid sequence of the polypeptide (a) or (b), wherein the polypeptide (c) does not include the amino acid sequence of SEQ ID NO: 1 or 3.

4. The polypeptide of claim 3, which is selected from the group consisting of:
(a) a polypeptide comprising an amino acid sequence having modification to SEQ ID NO: 1, wherein the modification is selected from the group consisting of amino acid mutations of F360M, F360L, F360I, F360C, F360V, F360T, V305I, V305L, A162L, A162C, A162I, V305M, R85A, F156A, V160C, V160S, F324V, L327T, I340T, R85A+F360M, R85A+F360V, R85A+F360I, F156A+F360M, V160C+F360M, V160C+F360I, V160C+F360V, A162C+F360M, A162C+F360I, A162C+F360V, A162L+F360M, A162L+F360I, A162L+F360V, V305M+F360M, V305M+F360I, V305M+F360V, F324V+F360M, L327T+F360M, L327T+F360I, L327T+F360V, I340T+F360M, R85A+V160C+F360I, R85A+A162L+F360M, R85A+V305M+F360I, R85A+L327T+F360M, V160C+A162L+F360I, V160C+V305M+F360M, V160C+L327T+F360I, A162L+V305M+F360M, A162C+L327T+F360M, V305M+L327T+F360M, A162C+V305M+F360M, A162I+V305M+F360M, V160C+A162C+F360M, V160C+A162L+F360M, R85A+V160C+A162L+F360I, R85A+V160C+V305M+F360M, R85A+V160C+L327T+F360I, R85A+A162C+L327T+F360M, R85A+A162L+V305M+F360M, R85A+V305M+L327T+F360M, V160C+A162L+V305M+F360I, V160C+A162C+L327T+F360M, A162C+V305M+L327T+F360M, R85A+V160C+A162C+L327T+F360M, R85A+V160C+A162L+V305M+F360M, V160C+A162C+V305M+L327T+F360M, and R85A+V160C+A162C+V305M+L327T+F360M, in the amino acid sequence of SEQ ID NO: 1;
(b) a polypeptide comprising an amino acid sequence having modification to SEQ ID NO: 3, wherein the modification is selected from the group consisting of amino acid mutations of F359M, F359C, F359L, F359I, F359V, F359T, V304I, V304L, A166L, A166C, A166I, V304M, R88A, F160A, V164C, V164S, F323V, L326T, I339T, R88A+F359I, R88A+F359V, R88A+F359M, V164C+F359I, V164C+F359V, V164C+F359M, A166L+F359I, A166L+F359V, V164C+F359M, A166C+F359I, A166C+F359V, A166L+F359M, A166C+F359M, F160A+F359M, V304M+F359I, V304M+F359V, V304M+F359M, F323V+F359M, L326T+F359I, L326T+F359V, L326T+F359M, I339T+F359M, R88A+V164C+F359I, R88A+A166L+F359M, R88A+V304M+F359I, R88A+L326T+F359M, V164C+A166L+F359I, V164C+V304M+F359M, V164C+L326T+F359I, A166L+V304M+F359M, A166L+L326T+F359I, V304M+L326T+F359M, A166C+V304M+F359M, A166I+V304M+F359M, V164C+A166C+F359M, V164C+A166L+F359M, R88A+V164C+A166L+F359M, R88A+V164C+V304M+F359I, R88A+V164C+L326T+F359M, R88A+A166L+V304M+F359M, R88A+A166L+L326T+F359M, R88A+V304M+L326T+F359M, V164C+A166L+V304M+F359I, V164C+A166L+L326T+F359M, A166L+V304M+L326T+F359I, R88A+V164C+A166L+V304M+F359I, R88A+V164C+A166L+L326T+F359M, V164C+A166L+V304M+L326T+F359M, and R88A+V164C+A166C+V304M+L326T+F359M, in the amino acid sequence of SEQ ID NO: 3;
a polypeptide obtained by a chemical synthesis or recombination method and comprising an amino acid sequence with at least 95% identity with the amino acid sequence of the polypeptide (a) or (b), wherein the polypeptide (c) does not include the amino acid sequence of SEQ ID NO: 1 or 3.

5. A polynucleotide encoding the polypeptide of claim 1.
6. A recombinant vector comprising the polynucleotide of claim 5.
7. A recombinant cell comprising the recombinant vector of claim 6.
8. A composition for conferring or enhancing herbicide tolerance of a plant or algae, comprising one or more selected from the group consisting of:
the polypeptide of claim 1;
a polynucleotide encoding the polypeptide;
a recombinant vector comprising the polynucleotide; and
a recombinant cell comprising the recombinant vector.
9. The composition of claim 8, wherein the herbicide is an herbicide inhibiting protoporphyrinogen IX oxidase.
10. The composition of claim 8, wherein the herbicide is at least one selected from the group consisting of pyrimidinediones, diphenyl-ethers, phenylpyrazoles, N-phenylphthalimides, phenylesters, thiadiazoles, oxadiazoles, triazolinones, oxazolidinediones, pyraclonil, flufenpyr-ethyl, and profluazol.
11. The composition of claim 10, wherein the herbicide is at least one selected from the group consisting of butafenacil, saflufenacil, benzfendizone, tiafenacil, fomesafen, oxyfluorfen, aclonifen, acifluorfen, bifenox, ethoxyfen, lactofen, chlomethoxyfen, chlorintrofen, fluoroglycofen-ethyl, halosafen, pyraflufen-ethyl, fluazolate, flumioxazin, cinidon-ethyl, flumiclorac-pentyl, fluthiacet, thidiazimin, oxadiargyl, oxadiazon, carfentrazone, sulfentrazone, azafenidin, pentoxazone, pyraclonil, flufenpyr-ethyl, profluazol, phenopylate, carbamate analogues of phenopylate, and agriculturally acceptable salt thereof.
12. A method of preparing a transgenic plant or algae having herbicide tolerance, the method comprising introducing the polypeptide of claim 1 or a polynucleotide encoding the same into an alga, or a cell, protoplast, callus, hypocotyl, seed, cotyledon, shoot, or whole body of a plant.

13. A method of conferring or enhancing herbicide tolerance of a plant or algae, the method comprising introducing the polypeptide of claim 1 or a polynucleotide encoding the same into an alga, or a cell, protoplast, callus, hypocotyl, seed, cotyledon, shoot, or whole body of a plant.

14. A method of controlling weeds in a cropland, the method comprising:
   providing the cropland with a plant comprising the polypeptide of claim 1 or a polynucleotide encoding the same, and
   applying an effective dosage of protoporphyrinogen IX oxidase-inhibiting herbicide to the cropland or the plant.

15. The method of claim 14, wherein the step of applying an effective dosage of protoporphyrinogen IX oxidase-inhibiting herbicide to the cropland is performed by applying an effective dosage of two or more kinds of protoporphyrinogen IX oxidase-inhibiting herbicides sequentially or simultaneously.

16. The method of claim 14, wherein the plant further comprises a second herbicide-tolerant polypeptide or a gene encoding the same, and
   the step of applying an effective dosage of protoporphyrinogen IX oxidase-inhibiting herbicide to the cropland is performed by applying effective dosages of the protoporphyrinogen IX oxidase-inhibiting herbicide and a second herbicide are applied sequentially or simultaneously.

17. A method of removing an undesired aquatic organism from a culture media, the method comprising:
   providing a culture media with algae comprising the polypeptide of claim 1 or a polynucleotide encoding the same, and
   applying an effective dosage of protoporphyrinogen IX oxidase-inhibiting herbicide to the culture media.

18. A transformant of a plant or algae having herbicide tolerance, or a clone or progeny thereof, comprising the polypeptide of claim 1 or a polynucleotide encoding the same.

19. The transformant, clone, or progeny thereof of claim 18, wherein the transformant is an alga, or a cell, protoplast, callus, hypocotyl, seed, cotyledon, shoot, or whole body of a plant.

20. The transformant of claim 18, wherein the plant or algae further comprise a second herbicide-tolerant polypeptide or a gene encoding the same, and its tolerance to the second herbicide is conferred or enhanced.

21. The transformant of claim 20, wherein the second herbicide is selected from the group consisting of glyphosate, glufosinate, dicamba, 2,4-D (2,4-Dichlorophenoxyacetic acid), isoxaflutole, ALS (acetolactate synthase)-inhibiting herbicide, photosystem II-inhibiting herbicide, phenylurea-based herbicide, bromoxynil-based herbicide, and combinations thereof.

22. The transformant of claim 20, wherein the second herbicide-tolerant polypeptide is one or more selected from the group consisting of:
   glyphosate herbicide-tolerant EPSPS (glyphosate resistant 5-enolpyruvylshikimate-3-phosphate synthase), GOX (glyphosate oxidase), GAT (glyphosate-N-acetyltransferase) or glyphosate decarboxylase;
   glufosinate herbicide-tolerant PAT (phosphinothricin-N-acetyltransferase);
   dicamba herbicide-tolerant DMO (dicamba monooxygenase);
   2,4-D (2,4-dichlorophenoxyacetic acid) herbicide-tolerant 2,4-D monooxygenase or AAD (aryloxyalkanoate dioxygenase);
   ALS (acetolactate synthase)-inhibiting sulfonylurea-based herbicide-tolerant ALS (acetolactate synthase), AHAS (acetohydroxyacid synthase) or AtAHASL (*Arabidopsis thaliana* acetohydroxyacid synthase large subunit);
   photosystem II-inhibiting herbicide-tolerant photosystem II protein D1;
   phenylurea herbicide-tolerant Cytochrome P450;
   plastid-inhibiting herbicide-tolerant HPPD (hydroxyphenylpyruvate dioxygenase);
   bromoxynil herbicide-tolerant nitrilase; and
   combinations thereof.

23. The transformant of claim 20, wherein the gene encoding the second herbicide-tolerant polypeptide is one or more selected from the group consisting of:
   glyphosate herbicide-tolerant cp4 epsps, mepsps, 2mepsps, goxv247, gat4601 or gat4621 gene;
   glufosinate herbicide-tolerant BAR or PAT gene;
   dicamba herbicide-tolerant dmo gene;
   2,4-D(2,4-dichlorophenoxyacetic acid) herbicide-tolerant AAD-1 or AAD-12 gene;
   isoxaflutole herbicide-tolerant HPPDPF W336 gene;
   sulfonylurea herbicide-tolerant ALS, Csr1, Csr1-1, Csr1-2, GM-HRA, S4-HRA, Zm-HRA, SurA or SurB gene;
   photosystem II-inhibiting herbicide-tolerant psbA gene;
   phenylurea herbicide-tolerant CYP76B1 gene;
   bromoxynil herbicide-tolerant bxn gene; and
   combinations thereof.

* * * * *